US006653292B1

(12) United States Patent
Krieg et al.

(10) Patent No.: US 6,653,292 B1
(45) Date of Patent: Nov. 25, 2003

(54) METHOD OF TREATING CANCER USING IMMUNOSTIMULATORY OLIGONUCLEOTIDES

(75) Inventors: Arthur M. Krieg, Iowa City, IA (US); George Weiher, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/337,619

(22) Filed: Jun. 21, 1999

Related U.S. Application Data

(60) Division of application No. 08/960,774, filed on Oct. 30, 1997, now Pat. No. 6,239,116, which is a continuation-in-part of application No. 08/738,652, filed on Oct. 30, 1996, now Pat. No. 6,207,646, which is a continuation-in-part of application No. 08/386,063, filed on Feb. 7, 1995, now Pat. No. 6,194,388, which is a continuation-in-part of application No. 08/276,358, filed on Jul. 15, 1994, now abandoned.

(51) Int. Cl.⁷ .............................................. A61P 37/04
(52) U.S. Cl. ...................................... 514/44; 536/23.1
(58) Field of Search ........................... 514/44; 536/23.1

(56) References Cited

U.S. PATENT DOCUMENTS

| | | | |
|---|---|---|---|
| 3,906,092 A | 9/1975 | Hilleman et al. | 424/89 |
| 5,248,670 A | 9/1993 | Draper et al. | 514/44 |
| 5,417,972 A | 5/1995 | Bhat et al. | 424/137.1 |
| 5,445,938 A | 8/1995 | Hanai et al. | 435/7.23 |
| 5,491,088 A | 2/1996 | Hellstrom et al. | 435/240.24 |
| 5,585,479 A | 12/1996 | Hoke et al. | 536/24.5 |
| 5,663,153 A | 9/1997 | Hutcherson et al. | 514/44 |
| 5,679,647 A | 10/1997 | Carson et al. | 514/44 |
| 5,723,335 A | 3/1998 | Hutcherson et al. | 435/375 |
| 5,756,097 A | 5/1998 | Landucci et al. | 424/155.1 |
| 5,780,448 A | 7/1998 | Davis | 514/44 |
| 5,786,189 A | 7/1998 | Locht et al. | 435/172.3 |
| 5,837,243 A | 11/1998 | Deo et al. | 424/136.1 |
| 5,849,719 A | 12/1998 | Carson et al. | 514/44 |
| 6,426,334 B1 | 7/2002 | Agrawal et al. | 514/44 |

FOREIGN PATENT DOCUMENTS

| | | |
|---|---|---|
| EP | 0468520 A3 | 1/1992 |
| EP | 0302758 B1 | 3/1994 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 94/19945 | 9/1994 |
| WO | WO 95/05853 | 3/1995 |
| WO | WO 95/26204 | 10/1995 |
| WO | WO 96/02555 | 2/1996 |
| WO | WO 96/02560 A1 | 2/1996 |
| WO | WO 96/35782 | 11/1996 |
| WO | WO 97/28259 | 8/1997 |
| WO | WO 98/14210 | 4/1998 |
| WO | WO 98/32462 A1 | 7/1998 |
| WO | WO 98/55495 A2 | 12/1998 |

OTHER PUBLICATIONS

Adya N et al., Expansion of CREB's DNA recognition specificity by Tax results from interaction with Ala–Ala–Arg at positions 282–284 near the conserved DNA–binding domain of CREB. *Proc Natl Acad Sci USA* 91(12):5642–6, Jun. 7, 1994.

Angier, N., Microbe DNA Seen as Alien By Immune System, *New York Times*, Apr. 11, 1995.

Azad RF et al., Antiviral Activity of a Phosphorotioate Oligonucleotide Complementary to RNA of the Human Cytomegalovirus Major Immediate–Early Region. *Antimicrobial Agents and Chemotherapy*, 37:1945–1954, Sep., 1993.

Azuma, Biochemical and Immunological Studies on Cellular Components of *Tubercle bacilli*, *Kekkaku*, vol. 69, 9:45–55, 1992.

Ballas ZK et al., Induction of NK activity in murine and human cells by CpG motifs in oligodeoxynucleotides and bacterial DNA. *J. Immunol* 157(5):1840–5, 1996.

Bayever, E., Systemic Administration of a Phosphorotioate Oligonucleotide with a Sequence Complementary to p53 for Acute Myelogenous leukemia and Myelodysplastic Syndrome: Initial Results of a Phase I Trial, *Antisense Res. & Dev.* (1993), 3:383–390.

Bennett RM et al., DNA binding to human leukocytes. Evidence for a receptor–mediated association, internalization, and degradation of DNA. *J. Clin Invest* 76(6):2182–90, 1985.

Bernhard, M., et al., Monocyte Macrophage Mediated Antibody Dependent and Independent Cell Mediated Cytotoxicity in Normals and Cancer Patients, ABSTRACT, *Proceedings of AACR and ASCO*, 22:372, c–159.

Blaxter et al., Genes expressed in *Brugia malayi* infective third stage larvae. *Molecular and Biochemical Parasitology*, 77:77–93.

Boggs RT et al., Characterization and modulation of immune stimulation by modified oligonucleotides. *Antisense Nucleic Acid Drug Dev* 7(5):461–71, Oct. 1997.

Branda RF et al., Amplification of antibody production by phosphorothioate oligodeoxynucleotides. *J. Lab Clin Med* 128(3):329–38, Sep. 1996.

Branda et al., Immune Stimulation by an Antisense Oligomer Complementary to the rev gene of HIV–1. *Biochemical Pharmacology*, vol. 5, 10:2037–2043, 1993.

Briskin M et al., Lipopolysaccharide–unresponsive mutant pre–B–cell lines blocked in NF–kappa B activation. *Mol Cell Biol* 10(1):422–5, Jan. 1990.

(List continued on next page.)

Primary Examiner—James Martinell
(74) Attorney, Agent, or Firm—Wolf, Greenfield & Sacks, P.C.

(57) ABSTRACT

Nucleic acid sequences containing unmethylated CpG dinucleotides that modulate an immune response including stimulating a Th1 pattern of immune activation, cytokine production, NK lytic activity, and B cell proliferation are disclosed. The sequences are also useful a synthetic adjuvant.

57 Claims, 19 Drawing Sheets

OTHER PUBLICATIONS

Chace, J. et al., Regulation of Differentiation in CD5+ and Conventional B Cells, *Clinical Immunology and Immunopathology*, (1993), 68:3:327–332.

Chang YN et al., The palindromic series I repeats in the simian cytomegalovirus major immediate–early promoter behave as both strong basal enhancers and cyclic AMP response elements. *J Virol* 64(1):264–77, Jan. 1990.

Chu RS et al., CpG oligodeoxynucleotides act as adjuvants that switch on T helper 1 (Th1) immunity. *J Exp Med* 186(10):1623–31, Nov. 17, 1997.

Cohen, J., et al., "IL–12 Deaths: Explanation and a Puzzle", *Science*, 10:270:5238:908.

Cossum, P., et al., "Pharmacokinetics of a $^{14}$C–Labeled Phosphorothioate Oligonucleotide, ISIS 2105, after Intradermal Administration to Rats", The Journal of Pharmacology and Experimental Therapeutics, 269:1:89–94, (1993).

Cowdery JS et al., Bacterial DNA induces NK cells to produce IFN–gamma in vivo and increases the toxicity of lipopolysaccharides. *J Immunol* 156(12):4570–5, Jun. 15, 1996.

Crosby et al., The Early Responses Gene FGFI–C Encodes a Zinc Finger Transcriptional Activator and is a Member of the GCGGGGGCG (GSG) Element–Binding Protein Family. *Mol. Cell. Biol.*, 2:3835–3841, 1991.

Crystal, Transfer of Genes to Humans: Early Lessons and Obstacles to Success. *Science*, vol. 270, pp. 404–410, 1995.

Doe, B., et al., "Induction of cytotoxic T lymphocytes by intramuscular immunization with plasmid DNA is facilitated by bone marrow–derived cells", *Proc. Natl. Acad. Sci.*, 93:8578–8583, (1996).

Englisch et al., Chemically Modified Oligonucleotides as Probes and Inhibitors, *Angew. Chem. Int. Ed. Engl.*, 30:613–629, 1991.

Erb KJ et al., Infection of mice with Mycobacterium bovis-Bacillus Calmette–Guerin (BCG) suppressess allergen–induced airway eosinophilia. *J Exp Med* 187(4):561–9, Feb. 16, 1998.

Etlinjer, Carrier sequence selection—one key to successful vaccines, *Immunology Today*, vol. 13, 2:52–55, 1992.

Fox RI, Mechanism of action of hydroxychloroquine as an antirheumatic drug. *Chemical Abstracts*, 120:15, Abstract No. 182630 (Apr. 29, 1994).

Gately, M., et al., "Interleukin–12: A Recently Discovered Cytokine with potential for Enhancing Cell–Mediated Immune Responses to Tumors", *Cancer Investigation*, 11:4:500–506, (1993).

Gura, T., Antisense Has Growing Pains. *Science* (1995), 270:575–576.

Hadden J et al., Immunostimulants. *TIPS*, (1993), 141:169–174.

Hadden J et al., Immunopharmacology, *JAMA*, (1992) 268:20:2964–2969.

Halpern MD et al., Bacterial DNA induces murine interferon–gamma production by stimulation of interleukin–12 and tumor necrosis factor–alpha. *Cell Immunol* 167(1):72–8, 1996.

Hartmann, G., et al., "CpG DNA: A potent signal for growth, activation, and maturation of human dendritic cells", *Proc. Natl. Acad. Sci.*, 96:9305–9310, (1999).

Hatzfeld J., Release of Early Human Hematopoietic Progenitors from Quiescence by Antisense Transforming Growth Factor β1 or Rb Oligonucleotides, *J. Exp. Med.*, (1991) 174:925–929.

Highfield PE, Sepsis: the More, the Murkier. *Biotechnology*, 12:828, Aug. 12, 1994.

Hoeffler JP et al., Identification of multiple nuclear factors that interact with cyclic adenosine 3',5'–monophosphate response element–binding protein and activating transcription factor–2 by protein–protein interactions. *Mol Endocrinol* 5(2):256–66, Feb. 1991.

Iguchi–Ariga SM and Shaffner W, CpG methylation of the cAMP–responsive enhancer/promoter sequence TGACGTCA abolishes specific factor binding as well as transcriptional activation. *Genes Dev.* 3(5):612–9, May 1989.

Iversen, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43–52.

Ishikawa R et al., IFN induction and associated changes in splenic leukocyte distribution. *J Immunol* 150(9):3713–27, May 1, 1993.

Jakway JP et al., Growth regulation of the B lymphoma cell line WEHI–231 by anti–immunoglobulin, lipopolysaccharide, and other bacterial products. *J Immunol* 137(7):2225–31, Oct. 1, 1986.

Jaroszewski JW and Cohen JS, Cellular uptake of antisense oligonucleotides. *Adv Drug Delivery Rev* 6(3):235–50, 1991.

Kataoka, T., et al. "Immunotherapeutid potential in Guinea–Pig Tumor Model of Deoxyribonucleic Acid From Mycobacterium Bovix BCG Complexed with Poly–L–Lysine and Carboxy–Methylcellulose", *Jpn J. Med. Sci. Biol.* 43:171–182, (1990).

Kimura Y et al., Binding of Oligoguanylate to Scavenger Receptors Is Required for Oligonucleotides to Augment NK Cell Activity and Induce INF, *J. Biochem.*, vol. 116, 5:991–994, 1994.

Kline JN et al., GpG motif oligonucleotides are effective in prevention of eosinophilic inflammation in a murine model of asthma. *J Invest Med* 44(7):380A, 1996.

Kline JN et al., Immune redirection by CpG oligonucleotides. Conversion of a Th2 response to a Th1 response in a murine model of asthma. *J Invest Med* 45(3):282A, 1997.

Kline JN et al., CpG oligonucleotides can reverse as well as prevent Th2–mediated inflammation in a murine model of asthma. *J Invest Med* 45(7):298A, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879–83, 1996.

Kolitz, J., et al., "The Immunotherapy of Human Cancer with Interleukin 2: Present Status and Future Directions", *Cancer Investigation*, 9:5:529–542, (1991).

Krieg AM et al., Uptake of oligodeoxyribonucleotides by lymphoid cells is heterogeneous and inducible. *Antisense Res Dev* 1(2):161–71, Summer 1991.

Krieg AM et al., Oligodeoxynucleotide modifications determine the magnitude of B cell stimulation by CpG motifs. *Antisense Nucleic Acid Drug Dev* 6(2):133–9, Summer 1996.

Krieg AM et al., "Modification of antisense phosphodiester oligodeoxynucleotides by a 5' cholesteryl moiety increases cellular association and improves efficacy", *Proc. Natl. Acad. Sci.*, (1993), 90:1048–1052.

Krieg AM et al., "CpG DNA: A Pathogenic Factor in Systemic Lupus Erythematosus?", *Journal of Clinical Immunology*, (1995) 15:6:284–292.

Krieg AM et al, Phosphorothioate Oligodeoxynucleotides: Antisense or Anti–Protein?, *Antisense Research and Development*, (1995), 5:241.

Krieg AM et al., "Leukocyte Stimulation by Oligodeoxynucleotides", *Applied Antisense Oligonucleotide Technology*, (1998), 431–448.

Krieg AM et al., CpG motifs in bacterial DNA trigger direct B–cell activation. *Nature* 374:546–9, 1995.

Krieg AM et al, "The role of CpG dinuleotides in DNA vaccines", Trends in Microbiology, vol. 6, pp. 23–27, Jan. 1998.

Krieg AM el al, A Role for Endogenous Retroviral Sequences in the Regulation of Lymphocyte Activation, the Journal of Immunology, vol. 143, 2448–2451.

Kuramoto et al., Oligonucleotide Sequences Required for Natural Killer Cell Activation, *Jpn. J. Cancer Res.*, 83:1128–1131, Nov. 1992.

Kuramoto et al., "In Situ Infiltration of Natural Killer–Like Cell sInduced by Intradermal Injection of the Nucleic Injection of the Nucleic Acid Fraction from BCG", *Microbiol. Immunol.*, 33:11:929–940, (1989).

Kuramoto, E., et al., "Changes of host cell infiltration into meth a fibrosarcoma tumor during the course of regression induced by injections of a BCG nucleic acid fraction", Int. I. Immunopharmacol. 14:5:773–782, (1992).

Lacour, J., et al., Clinical Trials Using Polyadenylic–Polyuridylic Acid as an Adjuvant to Surgery in Treating Different Human Tumors, *J of Biological Response Modifiers*, 4:538–543, (1985).

Leonard et al., Conformation of Guanine 8–Oxoadenine Base Pairs in the Crystal Structure of d(CGCGAATT(O8A)GCG). *Biochemsitry*, 31(36):8415–8420, 1992.

Macfarlane, DE and Manzel L, Antagonism of immunostimulatory CpG–oligodeoxynucleotides by quinacrine, chloroquine, and structurally related compounds. *J Immunol* 160(3):1122–31, Feb. 1, 1998.

Mastrangello et al. *Seminars in Oncology.* vol. 23, 1:4–21, 1996.

Mashiba, H., et al., "In Vitro Augmentation of Natural Killer Activity of Peripheral Blood Cells From Cancer Patients by a DNA Fraction From Mycobacterium Bovis BCG", *Jpn J. Med. Sci. Biol.*, 41:197–202, (1988).

Matson S and Krieg AM, Nonspecific suppression of [3H] thymidine incorporation by "control" oligonucleotides. *Antisense Res Dev* 2(4):325–30, Winter 1992.

McIntyre KW et al., A sense phosphorothioate oligonucleotide directed to the initiation codon of transcription factor NF–kappa B p65 causes sequence–specific immune stimulation. *Antisense Res Dev* 3(4):309–22, Winter 1993.

Messina et al., The Influence of DNA Structure on the in vitro Stimulation of Murine Lymphocytes by Natural and Synthetic Polynucleotide Antigens. *Cellular Immunology*, 147:148–157, 1993.

Messina et al., Stimulation of in vitro Murine Lymphocyte Proliferation by Bacterial DNA. *J. Immunol.*, vol. 147, 6:1759–1764, Sep. 15, 1991.

Mojcik, C., et al., "Administration of a Phosphorothioate Oligonucleotide Antisense Murine Endogenous Retroviral MCF env Causes Immune Effect in vivo in a Sequence–Specific Manner", *Clinical Immunology and Immunopathology*, (1993), 67:2:130–136.

Morahan, P., et al., "Comparative Analysis of Modulators of Nonspecific Resistance Against Microbial Infections", *Immunopharmacology of Infectious Diseases: Vaccine Adjuvants and Modulators of Non–Specific Resistance*, 313–324, (1987).

Mottram et al., A novel CDC2–related protein kinase from leishmania mexicana LmmCRK1 is post–translationally regulated during the life cycle. *J. Biol. Chem.* 268:28, 21044–21052 (Oct. 1993).

*New England BIOLABS* 1988–1989 Catalog.

Nyce JW and Metzger WJ, DNA antisense therapy for asthma in an animal model. *Nature* 385:721–725, Feb. 20, 1997.

Pisetsky, D., "Stimulation of in vitro proliferation of murine lymphocytes by synthetic oligodeoxynucleotides", *Molecular Biology Repairs*, (1993) 18:217–221.

Pisetsky et al., Stimulation of Murine Lymphocyte Proliferation by a Phosphorothioate Oligonucleotide with Antisense Activity for Herpes Simplex Virus. *Life Science*, vol. 54, pp. 101–107 (1994).

Pisetsky, The Immunological Properties of DNA, *The Journal of Immunology*, pp. 421–423 (1996).

Pisetsky, Immunological Consequences of Nucleic Acid Therapy, *Antisense Research and Development*, 5:219–225 (1995).

Raz E et al., Preferential induction of a Th1 immune response and inhibition of specific IgE antibody formation by plasmid DNA immunization. *Proc Natl Acad Sci USA* 91:9519–9523 (1994).

Reisfeld, R., et al., "Monoclonal Antibodies in Cancer Therapy", Clinics in Laboratory Medicine, 12:2:201–216, (1992).

Rosenberg, S., et al., "Immunotherapy of Cancer by Systemic Administration of Lymphoid Cells Plus Interleukin–2", *Journal of Biological Response Modifiers*, 3:501–511, (1984).

Rosenberg, S., et al., "Observations on the systemic administration of autologous lymphokine–activated killer cells and recombinant interleukin–2 to patients with metastatic cancer", The New England Journal of Medicine, 113:23:1485–1492, (1985).

Roman M et al., Immunostimulatory DNA sequences function as T helper–1–promoting adjuvants. *Nat Med* 3(8):849–54, Aug. 1997.

Sato et al., Immunostimulatory DNA Sequences Necessary for Effective Intradermal Gene Immunization, *Science*, vol. 273, pp. 352–354, 1996.

Schnell et al., Identification and characterization of a *Saccharomyces cerevisiae* gene (PAR1) conferring resistance to iron chelators. *Eur. J. Biochem.*, 200:487–493.

Schwartz DA et al., CpG motifs in bacterial DNA cause inflammation in the lower respiratory tract. *J Clin Invest* 100(1):68–73, Jul. 1, 1997.

Shimada, S., et al., "In Vivo Augmentatio of Natural Killer Cell Activity With A Deoxyribonucleic Acid Fraction of BCG", *Jpn J. Cancer Res.*, 77:808–816, (1986).

Shirakawa T et al., The inverse association between tuberculin responses and atopic disorder. *Science* 275(5296):77–9, Jan. 3, 1997.

Sparwasser T et al., Macrophages sense pathogens via DNA motifs: induction of tumor necrosis factor–alpha–mediated shock. *Eur J Immunol* 27(7):1671–9, Jul. 1997.

Stein CA et al., Oligonucleotides as inhibitors of gene expression: a review. *Cancer Research*, 48:2659–2668, 1988.

Stevenson, H., et al., "The Treatment of Cancer with Activated Cytotoxic Leukocyte Subsets", *Artif Organs*, 12:2:128136, 1988.

Stull et al., Antigene, Ribozyme, and Aptamer Nucleic Acid Drugs: Progress and Prospects, *Pharmaceutical Res.*, vol. 12, 4:465–483, 1995.

Subramanian et al., Theoretical Considerations on the "Spine of Hydration" in the Minor Groove of d(CGCGAAT-TCGCG) d(GCGCTTAAGCGC): Monte Carlo Computer Simulation. *Proc. Nat'l. Acad. Sci. USA*, 85:1836–1840, 1988.

Tanaka T et al., An antisense Oligonucleotide complementary to a sequence in IG2b increases G2b germline transcripts stimulates B cell DNA synthesis and inhibits immunoglobulin secretion. *J. Exp. Med.*, 175:597–607, 1992.

Tokunaga T et al., Synthetic Oligonucleotides with Particular Base Sequences from the cDNA Encoding Proteins of *Myobacterium bovis* BCG Induce Interferons and Activate Natural Killer Cells, *Microbiol. Immunol.*, vol. 36, 1:55–66, 1992.

Tokunaga et al., A Synthetic Single–Stranded DNA, Ply (dG, dC), Induces Interferon α/β and –γ, Augments Natural Killer Activity and Suppresses Tumor Growth. *Jpn. J. Cancer Res.*, 79:682–686, Jun. 1988.

Topalian, S., et al., "Expansion of human tumor infiltrating lymphocytes for use in immunotherapy trials", *J. of Immunological Methods*, 102:127–141, (1987).

Torpey III, D., et al., Effects of Adoptive Immunotherapy with Autologous CD8+ t Lymphocytes on Immunologic Parameters: Lymphocyte Subsets and Cytotoxic Activity, *Clinical Immunology and Immunopathology*, 68:3:263–272, (1993).

Uhlmann et al., Antisense Oligonucleotides: A New Therapeutic Principle. *Chemical Reviews*, 90:543–584, 1990.

Vogels, M., et al., "Use of Immune Modulators in nonspecific Therapy of Bacterial Infections", *Antimicrobial Agents and Chemotherapy*, 36:1:1–5, (1992).

Wagner RW, Gene inhibition using antisense oligodeoxynucleotides. *Nature*, 372:L333–335, 1994.

Wallace et al., Oligonucleotide probes for the screening of recombinant DNA libraries. *Methods in Enzymology*, 152:432–442 (1987).

Weiss R., Upping the Antisense Ante: Scientists bet on profits from reverse genetics. *Science*, 139:108–109, 1991.

Whalen R, DNA Vaccines for Emerging Infection Diseases: What If?, *Emerging Infectious Disease*, vol. 2, 3:168–175, 1996.

Wooldridge, J., et al., "Immunostimulatory Oligodeoxynucleotides Containing CpG Motifs Enhance the Efficacy of Monoclonal Antibody Therapy of Lymhoma", *Blood*, 89:8:2994–2998, (1997).

Wu GY et al., Receptor–mediated gene delivery and expression in vivo. *J. Biol. Chem.*, 263:14621–14624, 1988.

Wu–Pong S., Oligonucleotides: Opportunities for Drug Therapy and Research. *Pharmaceutical Technology*, 18:102–114, 1994.

Yamamoto S et al., In vitro augmentation of natural killer activity and production of interferon–alpha/beta and gamma with deoxyribonucleic acid fraction from *Mycobacterium bovis* BCG. *Jpn J Cancer Res* 79:866–73, Jul. 1988.

Yamamoto S., Mode of Action of Oligonucleotide Fraction Extracted from Mycobacterium bovis BCG, *Kekkaku*, vol. 69, 9:29–32, 1994.

Yamamoto S et al., Unique Palindromic Sequences in Synthetic Oligonucleotides are Required to Induce INF and Augment INF–Mediated Natural Killer Activity. *J. Immunol.*, vol. 148, 12:4072–4076, Jun. 15, 1992.

Yamamoto T et al., Ability of Oligonucleotides with Certain Palindromes to Induce Interferon Production and Augment Natural Killer Cell Activity is Associated with Their Base Length. *Antisense Res. and Devel.*, 4:119–123, 1994.

Yamamoto et al., Lipofection of Synthetic Oligodeoxyribonucleotide Having a Palindromic Sequence AACGTT to Murine Splenocytes Enhance Interferon Production and Natural Killer Activity. *Microbiol. Immunol.*, vol. 38, 10:831–836, 1994.

Yamamoto T et al., Synthetic Oligonucleotides with Certain Palindromes Stimulate Interferon Production of Human Peripheral Blood Lymphocytes in vitro. *Jpn. J. Cancer Res.*, 85:775–779, 1994.

Yi, Ae–Kyung et al., IFN–γ Promotes IL–6 and IgM Secretion in Response to CpG Motifs in Bacterial DNA and Oligonucleotides, *The Journal of Immunology*, pp. 558–564 (1996).

Yi, Ae–Kyung et al., Rapid Immune Activation by CpG Motifs in Bacterial DNA, *The Journal of Immunology*, pp. 5394–5402 (1996).

Zhao Q et al., Stage–specific oligonucleotide uptake in murine bone marrow B–cell precursors. *Blood* 84(11):3660–6, Dec. 1, 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53–66, Spring 1993.

Hamblin, T., et al., "Ex Vivo Activation and Retransfusion of White Blood Cells", *Curr Stud Hematol Blood Transf.*, 57:249–266, (1990).

Shimada, S., et al., "Antitumor Activity of the DNA Fraction from Mycobacterium bovis BCG. II> Effects on Various Syngeneic Mouse Tumors", *JNCI*, 74:681–688, (1985).

Aggarwal, S.K. et al., "Cell–Surface–Associated Nucleic Acid in Tumorigenic Cells Made Visible with Platinum-–Complexes by Electron Microscopy", *Proc. Nat. Acad. Sci. USA*, Mar. 1975, pp. 928–932, vol. 72, No. 3.

Kataoka, T. et al., "Antitumor Activity of Synthetic Oligonucleotides with Sequences from cDNA Encoding Proteins of *Mycobacterium bovis* BCG", *Jpn. J. Cancer Res.*, Mar. 1992, pp. 244–247, vol. 83.

Klinman, D.M. et al., "Contribution of CpG Motifs to the Immunogenicity of DNA Vaccines", *J. of Immunol.*, 1997, pp. 3635–3639, vol. 158, No. 8, The American Association of Immunologists.

Lipford, G.B. et al., "CpG–containing synthetic oligonucleotides promote B and cytotoxic T cell responses to protein antigen: a new class of vaccine adjuvants", Eur. J. Immunol., 1997, pp. 2340–2344, vol. 27.

Lipford, G.B. et al, "Bacterial DNA as immune cell activator", *Inst. of Med. Mcirob., Immunol. and Hygiene*, 1998, pp. 496–500, Elsevier Science.

Stull, R.A. et al., "Antigene, Ribozyme and Aptamer Nucleic Acid Drugs: Progress and Prospects", *Pharmaceutical Research*, 1995, pp. 465–483, vol. 12, No. 4, Plenum Publishing Corp.

Sun, S. et al., "Mitogenicity of DNA from Different Organisms for Murine B Cells", *The Journal of Immunology*, 1997, pp. 3119–3125, The American Association of Immunologists.

Threadgill, D.S. et al., "Mitogenic synthetic polynucleotides suppress the antibody response to a bacterial polysaccharide", *Vaccine*, 1998, pp. 76–82, vol. 16, No. 1, Elsevier Science Ltd.

Wiltrout, R.H., et al., "Immunomodulation of Natural Killer Activity by Polyribonucleotides", *Journal of Biological Response Modifiers*, 1985, pp. 512–517, vol. 4, No. 5, New Raven Press, NY.

Wooldridge, J.E. et al., "Select Unmethylated CpG Oligodeoxynucleotides Improve Antibody Dependent Cellular Cytotoxicity in Vitro of Both Murine and Human B Cell Lymphomas", *Blood*, Dec. 1995, p. 2877, Abstract, vol. 86.

Wooldridge, J.E. et al., "Select unmethylated CpG oligodeoxynucleotide improve antibody dependent cellular cytotoxicity in vitro and in vivo", Proceedings of the American Association for Cancer Research #3253, Mar. 1996, p. 477, Abstract, vol. 37.

SEQUENCE LISTING

<160> NUMBER OF SEQ ID NOS: 123

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
atggaaggtc cagcgttctc                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
atcgacctac gtgcgttctc                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
tccataacgt tcctgatgct                                          20

<210> SEQ ID NO 4
<211> LENGTH: 15
<212> TYPE: DNA
<213> ORGANISM: Artificial Sequence

```
<220> FEATURE:
<223> OTHER INFORMATION: Synthetic Oligonucleotide

<400> SEQUENCE: 4
gctagatgtt agcgt                                                    15

<210> SEQ ID NO 5
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 5
gagaacgtcg accttcgat                                                19

<210> SEQ ID NO 6
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 6
gcatgacgtt gagct                                                    15

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
tccatgacgt tcctgatgct                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
tccatgagct tcctgagtct                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tccaagacgt tcctgatgct                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
tccatgacgt tcctgacgtt                                               20
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 11
tccatgagct tcctgagtgc t                                         21

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
ggggtcaacg ttgagggggg                                           20

<210> SEQ ID NO 13
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (7)...(7)
<223> OTHER INFORMATION: m5c

<400> SEQUENCE: 13
gctagangtt agcgt                                                15

<210> SEQ ID NO 14
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (13)...(13)
<223> OTHER INFORMATION: m5c

<400> SEQUENCE: 14
gctagacgtt agngt                                                15

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
atcgactctc gagcgttctc                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (3)...(3)
<223> OTHER INFORMATION: m5c
```

```
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 16
atngactctn gagngttctc                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (3)...(3)
<223> OTHER INFORMATION: m5c

<400> SEQUENCE: 17
atngactctc gagcgttctc                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (18)...(18)
<223> OTHER INFORMATION: m5c

<400> SEQUENCE: 18
atcgactctc gagcgttntc                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
atggaaggtc caacgttctc                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gagaacgctg gaccttccat                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
```

```
gagaacgctc gaccttccat                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
gagaacgctc gaccttcgat                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
gagcaagctg gaccttccat                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (6)...(6)
<223> OTHER INFORMATION: m5c

<400> SEQUENCE: 24
gagaangctg gaccttccat                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (14)...(14)
<223> OTHER INFORMATION: m5c

<400> SEQUENCE: 25
gagaacgctg gacnttccat                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
gagaacgatg gaccttccat                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
```
gagaacgctc cagcactgat          20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tccatgtcgg tcctgatgct          20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
tccatgctgg tcctgatgct          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c

<400> SEQUENCE: 30
tccatgtngg tcctgatgct          20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (12)...(12)
<223> OTHER INFORMATION: m5c

<400> SEQUENCE: 31
tccatgtcgg tnctgatgct          20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
tccatgtcgg tcctgctgat          20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 33
tccatgccgg tcctgatgct                                                    20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
tccatggcgg tcctgatgct                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
tccatgacgg tcctgatgct                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tccatgtcga tcctgatgct                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
tccatgtcgc tcctgatgct                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tccatgtcgt tcctgatgct                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
tccatgacgt ccctgatgct                                                    20

<210> SEQ ID NO 40
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 40
tccatcacgt gcctgatgct                                              20

<210> SEQ ID NO 41
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 41
ggggtcagtc ttgacgggg                                               19

<210> SEQ ID NO 42
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 42
gctagacgtt agtgt                                                   15

<210> SEQ ID NO 43
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c

<400> SEQUENCE: 43
gctagacntt agtgt                                                   15

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c

<400> SEQUENCE: 44
tccatgtngt tcctgatgct                                              20

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 45
tctcccagcg tgcgccat                                                18

<210> SEQ ID NO 46
```

-continued

<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 46
tcgtcgtttt gtcgttttgt cgtt                                    24

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
tcgtcgttgt cgttgtcgtt                                         20

<210> SEQ ID NO 48
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 48
tgtcgtttgt cgtttgtcgt t                                       21

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 49
tcgtcgttgt cgttttgtcg tt                                      22

<210> SEQ ID NO 50
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 50
tgtcgttgtc gttgtcgtt                                          19

<210> SEQ ID NO 51
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 51
tcgtcgtcgt cgtt                                               14

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52

```
tcctgtcgtt ccttgtcgtt                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
tcctgtcgtt ttttgtcgtt                                          20

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 54
tcgtcgctgt ctgcccttct t                                        21

<210> SEQ ID NO 55
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 55
tcgtcgctgt tgtcgtttct t                                        21

<210> SEQ ID NO 56
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 56
gcgtgcgttg tcgttgtcgt t                                        21

<210> SEQ ID NO 57
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 57 gtcgtt                                                          6

<210> SEQ ID NO 58
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 58 gtcgct                                                          6

<210> SEQ ID NO 59
<211> LENGTH: 24
<212> TYPE: DNA
```

```
<213> ORGANISM: Artificial Sequence
<220> FEATURE:
<223> OTHER INFORMATION: Synthetic Oligonucleotide

<400> SEQUENCE: 59
accatggacg atctgtttcc cctc                                              24

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 60
taccgcgtgc gaccctct                                                     18

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 61
accatggacg aactgtttcc cctc                                              24

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 62
accatggacg agctgtttcc cctc                                              24

<210> SEQ ID NO 63
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 63
accatggacg acctgtttcc cctc                                              24

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 64
accatggacg tactgtttcc cctc                                              24

<210> SEQ ID NO 65
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 65
accatggacg gtctgtttcc cctc                                              24
```

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 66
accatggacg ttctgtttcc cctc                                    24

<210> SEQ ID NO 67
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 67
cacgttgagg ggcat                                              15

<210> SEQ ID NO 68
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 68
ctgctgagac tggag                                              15

<210> SEQ ID NO 69
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 69
tcagcgtgcg cc                                                 12

<210> SEQ ID NO 70
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 70
atgacgttcc tgacgtt                                            17

<210> SEQ ID NO 71
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 71
tctcccagcg ggcgcat                                            17

<210> SEQ ID NO 72
<211> LENGTH: 18
<212> TYPE: DNA
<213> ORGANISM: Artificial Sequence
<220> FEATURE:

<223> OTHER INFORMATION: Synthetic Oligonucleotide

<400> SEQUENCE: 72
tctcccagcg cgcgccat                                            18

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
tccatgtcgt tcctgtcgtt                                          20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
tccatagcgt tcctagcgtt                                          20

<210> SEQ ID NO 75
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 75
tcgtcgctgt ctccgcttct t                                        21

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 76
tcctgacgtt cctgacgtt                                           19

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 77
tcctgtcgtt cctgtcgtt                                           19

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
tccatgtcgt ttttgtcgtt                                          20

```
<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
tccaggactt ctctcaggtt                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
tccatgcgtg cgtgcgtttt                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
tccatgcgtt gcgttgcgtt                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
tccacgacgt tttcgacgtt                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gcggcgggcg gcgcgcgccc                                              20

<210> SEQ ID NO 84
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 84
tgtcgttgtc gttgtcgttg tcgtt                                        25

<210> SEQ ID NO 85
<211> LENGTH: 13
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 85
tgtcgttgtc gtt                                                        13

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
tccacgacgt tttcgacgtt                                                 20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
tccatgacga tcctgatgct                                                 20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
tccatgacgc tcctgatgct                                                 20

<210> SEQ ID NO 89
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 89
gctagacgtt agcgt                                                      15

<210> SEQ ID NO 90
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 90 tcaacgtt                                                               8

<210> SEQ ID NO 91
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 91 tcaagctt                                                               8

<210> SEQ ID NO 92
<211> LENGTH: 8
```

```
<212> TYPE: DNA
<213> ORGANISM: Artificial Sequence
<220> FEATURE:
<223> OTHER INFORMATION: Synthetic Oligonucleotide

<400> SEQUENCE: 92 tcagcgct                                                              8

<210> SEQ ID NO 93
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 93 tcatcgat                                                              8

<210> SEQ ID NO 94
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 94 tcttcgaa                                                              8

<210> SEQ ID NO 95
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 95 ccaacgtt                                                              8

<210> SEQ ID NO 96
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 96 tcaacgtc                                                              8

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
tccaggactt tcctcaggtt                                                20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
```
ttcaggactt tcctcaggtt                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
ggcgttattc ctgactcgcc                                               20

<210> SEQ ID NO 100
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 100
cctacgttgt atgcgcccag ct                                            22

<210> SEQ ID NO 101
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 101 tgtcgct                                                              7

<210> SEQ ID NO 102
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 102 tgtcgtt                                                              7

<210> SEQ ID NO 103
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 103 tgacgtc                                                              7

<210> SEQ ID NO 104
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 104 tgacgtca                                                             8

<210> SEQ ID NO 105
<211> LENGTH: 6
<212> TYPE: DNA
<213> ORGANISM: Artificial Sequence

```
<220> FEATURE:
<223> OTHER INFORMATION: Synthetic Oligonucleotide

<400> SEQUENCE: 105 aacgtt                                                                    6

<210> SEQ ID NO 106
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 106 caacgtt                                                                   7

<210> SEQ ID NO 107
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 107 aacgttct                                                                  8

<210> SEQ ID NO 108
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 108 tgacgtt                                                                   7

<210> SEQ ID NO 109
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 109 gccggt                                                                    6

<210> SEQ ID NO 110
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 110 gacggt                                                                    6

<210> SEQ ID NO 111
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 111 gacgtc                                                                    6
```

<210> SEQ ID NO 112
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 112 cacgtg                                                                      6

<210> SEQ ID NO 113
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 113 cgacgtt                                                                     7

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
atggaaggtc cagtgttctc                                                      20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
atggactctc cagcgttctc                                                      20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (14)...(14)
<223> OTHER INFORMATION: m5c

<400> SEQUENCE: 116
atcgactctc gagngttctc                                                      20

<210> SEQ ID NO 117
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (7)...(7)
<223> OTHER INFORMATION: m5c

<400> SEQUENCE: 117
gctagangtt agtgt                                                           15

<210> SEQ ID NO 118
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 118
catttccacg atttccca                                                    18

<210> SEQ ID NO 119
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 119
tcgtcgctgt ctgcccttct t                                                21

<210> SEQ ID NO 120
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 120
tcgtcgctgt tgtcgtttct t                                                21

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
tccttgtcgt tcctgtcgtt                                                  20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c
<220> FEATURE:
<221> NAME/KEY: modified_base
<222> LOCATION: (17)...(17)
<223> OTHER INFORMATION: m5c

<400> SEQUENCE: 122
tccatgtngt tcctgtngtt                                                  20

<210> SEQ ID NO 123
<211> LENGTH: 23
<212> TYPE: DNA
<213> ORGANISM: Artificial Sequence -continued

```
<220> FEATURE:
<223> OTHER INFORMATION: Synthetic Oligonucleotide

<400> SEQUENCE: 123
tcgtcgtttt gtcgttttgt cgt                                              23
```

METHOD OF TREATING CANCER USING IMMUNOSTIMULATORY OLIGONUCLEOTIDES

RELATED APPLICATION

This application is a divisional of U.S. Ser. No. 08/960,774, filed Oct. 30, 1997, now issued as U.S. Pat. No. 6,239,116B1 on May 29, 2001, which is a continuation-in-part of U.S. Ser. No. 08/738,652, filed Oct. 30, 1996, which is now issued as U.S. Pat. No. 6,207,646B1 on Mar. 27, 2001, which is a continuation-in-part of U.S. patent application Ser. No. 08/386,063, filed Feb. 7, 1995 now issued as U.S. Pat. No. 6,194,388B1 on Feb. 27, 2001, which is a continuation-in-part of U.S. patent application Ser. No. 08/276,358, filed Jul. 15, 1994 which is now abandoned, each of which are incorporated herein by reference in their entirety.

GOVERNMENT

The work resulting in this invention was supported in part by National Institute of Health Grant No. R29-AR42556-01. The U.S. Government may have rights in the invention.

FIELD OF THE INVENTION

The present invention relates generally to oligonucleotides and more specifically to oligonucleotides which have a sequence including at least one unmethylated CpG dinucleotide which are immunostimulatory.

BACKGROUND OF THE INVENTION

In the 1970s, several investigators reported the binding of high molecular weight DNA to cell membranes (Lerner, R. A., et al. 1971. "Membrane-associated DNA in the cytoplasm of diploid human lymphocytes." *Proc. Natl. Acad. Sci. USA* 68:1212; Agrawal, S. K., R. W. Wagner, P. K. McAllister, and B. Rosenberg. 1975. "Cell-surface-associated nucleic acid in tumorigenic cells made visible with platinum-pyrimidine complexes by electron microscopy." *Proc. Natl. Acad. Sci. USA* 72:928). In 1985, Bennett et al. presented the first evidence that DNA binding to lymphocytes is similar to a ligand receptor interaction: binding is saturable, competitive, and leads to DNA endocytosis and degradation into oligonucleotides (Bennett, R. M., G. T. Gabor, and M. M. Merritt, 1985. "*J. Clin. Invest.* 76:2182). Like DNA, oligodeoxyribonucleotides (ODNs) are able to enter cells in a saturable, sequence independent, and temperature and energy dependent fashion (reviewed in Jaroszewski, J. W., and J. S. Cohen. 1991. "Cellular uptake of antisense oligodeoxynucleotides." *Advanced Drug Deliver Reviews* 6:235; Akhtar, S., Y. Shoji, and R. L. Juliano. 1992. "Pharmaceutical aspects of the biological stability and membrane transport characteristics of antisense oligonucleotides." In: *Gene Regulation: Biology of Antisense RNA and DNA*. R. P. Erickson, and J. G. Izant, eds. Raven Press, Ltd. New York, pp. 133; and Zhao, Q., T. Waldschmidt, E. Fisher, C. J. Herrera, and A. M. Krieg. 1994. "Stage specific oligonucleotide uptake in murine bone marrow B cell precursors." *Blood* 84:3660). No receptor for DNA or ODN uptake has yet been cloned, and it is not yet clear whether ODN binding and cell uptake occurs through the same or a different mechanism from that of high molecular weight DNA.

Lymphocyte ODN uptake has been shown to be regulated by cell activation. Spleen cells stimulated with the B cell mitogen LPS had dramatically enhanced ODN uptake in the B cell population, while spleen cells treated with the T cell mitogen Con A showed enhanced ODN uptake by T but not B cells (Krieg, A. M., F. Gmelig-Meyling, M. F. Gourley, W. J. Kisch, L. A. Chrisey, and A. D. Steinberg. 1991. "Uptake of oligodeoxyribonucleotides by lymphoid cells is heterogeneous and inducible." *Antisense Research and Development* 1:161).

Several polynucleotides have been extensively evaluated as biological response modifiers. Perhaps the best example is poly (I,C) which is a potent inducer of IFN production as well as macrophage activator and inducer of NK activity (Talmadge, J. E., J. Adams, H. Phillips, M. Collins, B. Lenz, M. Schneider, E. Schlick, R. Ruffmann, R. H. Wiltrout, and M. A. Chirigos. 1985. "Immunomodulatory effects in mice of polyinosinic-polycytidylic acid complexed with poly-L-lysine and carboxymethylcellulose." *Cancer Res.* 45:1058; Wiltrout, R. H., R. R. Salup, T. A. Twilley, and J. E. Talmadge. 1985. "Immunomodulation of natural killer activity by polyribonucleotides." *J. Biol. Respn. Mod.* 4:512; Krown, S. E. 1986. "Interferons and interferon inducers in cancer treatment." *Sem. Oncol.* 13:207; and Ewel, C. H., S. J. Urba, W. C. Kopp, J. W. Smith II, R. G. Steis, J. L. Rossio, D. L. Longo, M. J. Jones, W. G. Alvord, C. M. Pinsky, J. M. Beveridge, K. L. McNitt, and S. P. Creekmore. 1992. "Polyinosinic-polycytidylic acid complexed with poly-L-lysine and carboxymethylcellulose in combination with interleukin-2 in patients with cancer: clinical and immunological effects." *Canc. Res.* 52:3005). It appears that this murine NK activation may be due solely to induction of IFN-p secretion (Ishikawa, R., and C. A. Biron. 1993. "IFN induction and associated changes in splenic leukocyte distribution". *J. Immunol.* 150:3713). This activation was specific for the robose sugar since deoxyribose was ineffective. Its potent in vitro antitumor activity led to several clinical trials using poly (I,C) complexed with poly-L-lysine and carboxymethylcellulose (to reduce degradation by RNAse) Talmadge, J. E., et al., 1985. cited supra; Wiltrout, R. H., et al, 1985. cited supra); Krown, S. E., 1986. cited supra); and Ewel, C. H., et al., 1992. cited supra). Unfortunately, toxic side effects have thus far prevented poly (I,C) from becoming a useful therapeutic agent.

Guanine ribonucleotides substituted at the C8 position with either a bromine or a thiol group are B cell mitogens and may replace "B cell differentiation factors" (Feldbush, T. L., and Z. K., Ballas. 1985. "Lymphokine-like activity of 8-mercaptoguanosine: induction of T and B cell differentiation." *J. Immunol.* 134:3204; and Goodman, M. G. 1986. "Mechanism of synergy between T cell signals and C8-substituted guanine nucleosides in humoral immunity: B lymphotropic cytokines induce responsiveness to 8-mercaptoguanosine." *J. Immunol.* 136:3335). 8-mercaptoguanosine and 8-bromoguanosine also can substitute for the cytokine requirement for the generation of MHC restricted CTL (Feldbush, T. L., 1985. cited supra), augment murine NK activity (Koo, G. C., M. E. Jewell, C. L. Manyak, N. H. Sigal, and L. S. Wicker. 1988. "Activation of murine natural killer cells and macrophages by 8-bromoguanosine." *J. Immunol.* 140:3249), and synergize with IL-2 in inducing murine LAK generation (Thompson, R. A., and Z. K. Ballas. 1990. "Lymphokine-activated killer (LAK) cells. V. 8-Mercaptoguanosine as an IL-2-sparing agent in LAK generation." *J. Immunol.* 145:3524). The NK and LAK augmenting activities of these C8-substituted guanosines appear to be due to their induction of IFN (Thompson, R. A., et al. 1990. cited supra0. Recently, a 5' triphosphorylated thymidine produced by a mycobacterium was found to be mitogenic for a subset of human γδ T cells (Constant, P., F. Davodeau, M.-A. Peyrat, Y. Poquet, G. Puzo, M. Bonneville, and J.-J. Fournie. 1994. "Stimulation of human γδ T cells by nonpeptidic mycobacterial ligands." *Science* 264:267). This report indicated the possibility that the immune system may have evolved ways to preferentially respond to microbial nucleic acids.

Several observations suggest that certain DNA structures may also have the potential to activate lymphocytes. For example, Bell et al. reported that nucleosomal protein-DNA complexes (but not naked DNA) in spleen cell supernatants caused B cell proliferation and immunoglobulin secretion (Bell, D. A., B. Morrison, and P. VandenBygaart. 1990. "Immunogenic DNA-related factors." *J. Clin. Invest.* 85:1487). In other cases, naked DNA has been reported to have immune effects. For example, Messina et al. have recently reported that 260 to 800 bp fragments of poly (dG).(dC) and poly (dG.dC) were mitogenic for B cells (Messina, J. P., G. S. Gilkeson, and D. S. Piesetsky. 1993. "The influence of DNA structure on the in vitro stimulation of murine lymphocytes by natural and synthetic polynucleotide antigens." *Cell. Immunol.* 147:148). Tokunaga, et al. have reported that dGdC induces γ-IFN and NK activity (Tokunaga, S. Yamamoto, and K. Nama. 1988. "A synthetic single-stranded DNA, poly(dG, dC), induces interferon-α/b and -g, augments natural killer activity, and suppresses tumor growth." *Jpn. J. Cancer Res.* 79:682). Aside from such artificial homopolymer sequences, Pisetsky et al. reported that pure mammalian DNA has no detectable immune effects, but that DNA from certain bacteria induces B cell activation and immunoglobulin secretion (Messina, J. P., G. S. Gilkeson, and D. S. Pisetsky. 1991. "Stimulation of in vitro murine lymphocyte proliferation by bacterial DNA." *J. Immunol.* 147:1759). Assuming that these data did not result from some unusual contaminant, these studies suggested that a particular structure or other characteristic of bacterial DNA renders it capable of triggering B cell activation. Investigations of mycobacterial DNA sequences have demonstrated that ODN which contain certain palindrome sequences can activate NK cells (Yamamoto, S., T. Yamamoto, T. Kataoka, E. Kuramoto, O. Yano, and T. Tokunaga. 1992. "Unique palindromic sequences in synthetic oligonucleotides are required to induce INF and augment INF-mediated natural killer activity." *J. Immunol.* 148:4072Kuramoto, E., O. Yano, Y. Kimura, M. Baba, T.Makino, S. Yamamoto, T. Yamamoto, T. Kataoka, and T. Tokunaga. 1992. "Oligonucleotide sequences required for natural killer cell activation." *Jpn. J. Cancer Res.* 83:1128).

Several phosphorothioate modified ODN have been reported to induce in vitro or in vivo B cell stimulation (Tanaka, T., C. C. Chu, and W. E. Paul. 1992. "An antisense oligonucleotide complementary to a sequence in Ig2b increases g2b germline transcripts, stimulates B cell DNA synthesis, and inhibits immunoglobulin secretion." *J. Exp. Med.* 175:597; McIntyre, K. W., K. Lombard-Gillooly, J. R. Perez, C. Kunsch, U. M. Sarmiento, J. D. Larigan, K. T. Landreth, and R. Narayanan. 1993. "A sense phosphorothioate oligonucleotide directed to the initiation codon of transcription factor NF-κB T65 causes sequence-specific immune stimulation." *Antisense Res. Develop.* 3:309; and Pisetsky, D. S., and C. F. Reich. 1993. "Stimulation of murine lymphocyte proliferation by a phosphorothioate oligonucleotide with antisense activity for herpes simplex virus." *Life Sciences* 54:101). These reports do not suggest a common structural motif or sequence element in these ODN that might explain their effects.

The cAMP response element binding protein (CREB) and activating transcription factor (ATF) or CREB/ATF family of transcription factors is a ubiquitously expressed class of transcription factors of which 11 members have so far been cloned (reviewed on de Groot, R. P., and P. Sassone-Corsi: "Hormonal control of gene expression: Multiplicity and versatility of cyclic adenosine 3',5'-monophosphate-responsive nuclear regulators." *Mol. Endocrin.* 7:145, 1993; Lee, K. A. W., and N. Masson: "Transcriptional regulation by CREB and its relatives." *Biochim. Biophys. Acta* 1174:221, 1993). They all belong to the basic region/leucine zipper (bZip) class of proteins. All cells appear to express one or more CREB/ATF proteins, but the members expressed and the regulation of mRNA splicing appear to be tissue-specific. Differential splicing of activation domains can determine whether a particular CREB/ATF protein will be a transcriptional inhibitor or activator. Many CREB/ATF proteins activate viral transcription, but some splicing variants which lack the activation domain are inhibitory. CREB/ATF proteins can bind DNA as homo- or hetero-dimers through the cAMP response element, the CRE, the consensus form of which is the unmethylated sequence TGACGTC (SEQ. ID. No. 103) (binding is abolished if the CpG is methylated) (Iguchi-Ariga, S. M. M., and W. Schaffner: "CpG methylation of the cAMP-responsive enhancer/promoter sequence TGACGTCA (SEQ. ID. No.104) abolishes specific factor binding as well as transcriptional activation." *Genese & Develop.* 3:612, 1989.

The transcriptional activity of the CRE is increased during B cell activation (Xie. H., T. C. Chiles, and T. L. Rothstein: "Induction of CREB activity via the surface Ig receptor of B cells." *J. Immunol.* 151:880, 1993). CREB/ATF proteins appear to regulate the expression of multiple genes through the CRE including immunologically important genes such as fos, jun B, Rb-1, IL-6, IL-1 (Tsukada, J., K. Saito, W. R. Waterman, A. C. Webb, and P. E. Auron: "Transcription factors NF-IL6 and CREB recognize a common essential site in the human prointerleukin 1 gene." *Mol. Cell. Biol.* 14:7285, 1994; Gray, G. D., O. M. Hernandez, D. Hebel, M. Root, J. M. Pow-Sang, and E. Wickstrom: "Antisense DNA inhibition of tumor growth induced by c-Ha-ras oncogene in nude mice." *Cancer Res.* 53:577, 1993), IFN- (Du, W., and T. Maniatis: "An ATF/CREB binding site protein is required for virus induction of the human interferon B gene." *Proc. Natl. Acad. Sci. USA* 89:2150, 1992), TGF-1 (Asiedu, C. K., L. Scott, R. K. Assoian, M. Ehrlich: "Binding of AP-1/CREB proteins and of MDBP to contiguous sites downstream of the human TGF-B1 gene." *Biochim. Biophys. Acta* 1219:55, 1994), TGF-2, class II MHC (Cox, P. M., and C. R. Goding: "An ATF/CREB binding motif is required for aberrant constitutive expression of the MHC class II Dra promoter and activation by SV40 T-antigen." *Nuc. Acids Res.* 20:4881, 1992), E-selectin, GM-CSF, CD-8, the germline Ig constant region gene, the TCR V gene, and the proliferating cell nuclear antigen (Huang, D., P. M. Shipman-Appasamy, D. J. Orten, S. H. Hinrichs, and M. B. Prystowsky: "Promoter activity of the proliferating-cell nuclear antigen gene is associated with inducible CRE-binding proteins in interleukin 2-stimulated T lymphocytes." *Mol. Cell. Biol.* 14:4233, 1994). In addition to activation through the cAMP pathway, CREB can also mediate transcriptional responses to changes in intracellular $Ca^{++}$ concentration (Sheng, M., G. McFadden, and M. E. Greenberg: "Membrane depolarization and calcium induce c-fos transcription via phosphorylation of transcription factor CREB." *Neuron* 4:571, 1990).

The role of protein-protein interactions in transcriptional activation by CREB/ATF proteins appears to be extremely important. There are several published studies reporting direct or indirect interactions between NFKB proteins and CREB/ATF proteins (Whitley, et al., (1994) *Mol. & Cell. Biol.* 14:6464; Cogswell, et al., (1994) *J. Immun.* 153:712; Hines, et al, (1993) *Oncogene* 8:3189; and Du, et al., (1993) *Cell* 74:887. Activation of CREB through the cyclic AMP pathway requires protein kinase A (PKA), which phosphorylates $CREB^{341}$ on $ser^{133}$ and allows it to bind to a recently cloned protein, CBP (Kwok, R. P. S., J. R. Lundblad, J. C. Chrivia, J. P. Richards, H. P. Bachinger, R. G. Brennan, S. G. E. Roberts, M. R. Green, and R. H. Goodman: "Nuclear protein CBP is a coactivator for the transcription factor CREB." *Nature* 370:223, 1994; Arias, J., A. S. Alberts, P. Brindle, F. X. Claret, T. Smea, M. Karin, J. Feramisco, and M. Montminy: "Activation of cAMP and mitogen responsive genes relies on a common nuclear factor." *Nature* 370:226, 1994). CBP in turn interacts with the basal transcription factor TFIIB causing increased transcription. CREB also has been reported to interact with dTAFII 110, a TATA binding protein-associated factor whose binding may regulate transcription (Ferreri, K., G. Gill, and M. Montminy: "The cAMP-regulated transcription factor CREB interacts with a component of the TFIID complex." *Proc. Natl. Acad. Sci. USA* 91:1210, 1994). In addition to these interactions, CREB/ATF proteins can specifically bind multiple other nuclear factors (Hoeffler, J. P., J. W. Lustbadfer, and C.-Y. Chen: "Identification of multiple nuclear factors that interact with cyclic adenosine 3',5'-monophosphate response element-binding protein and activating transcription factor-2 by protein-protein interactions." *Mol. Endocrinol.* 5:256, 1991) but the biologic significance of most of these interactions is unknown. CREB is normally thought to bind DNA either as a homodimer or as a heterodimer with several other proteins. Surprisingly, CREB monomers constitutively activate transcription (Krajewski, W., and K. A. W. Lee: "A monomeric derivative of the cellular transcription factor CREB functions as a constitutive activator." *Mol. Cell. Biol.* 14:7204, 1994).

Aside from their critical role in regulating cellular transcription, it has recently been shown that CREB/ATF proteins are subverted by some infectious viruses and retroviruses, which require them for viral replication. For example, the cytomegalovirus immediate early promoter, one of the strongest known mammalian promoters, contains eleven copies of the CRE which are essential for promoter function (Chang, Y.-N., S. Crawford, J. Stall, D. R. Rawlins, K.-T. Jeang, and G. S. Hayward: "The palindromic series I repeats in the simian cytomegalovirus major immediate-early promoter behave as both strong basal enhancers and cyclic AMP response elements." *J. Virol.* 64:264, 1990). At least some of the transcriptional activating effects of the adenovirus E1A protein, which induces many promoters, are due to its binding to the DNA binding domain of the CREB/ATF protein, ATF-2, which mediates E1A inducible transcription activation (Liu, F., and M. R. Green: "Promoter targeting by adenovirus E1A through interaction with different cellular DNA-binding domains." *Nature* 368:520, 1994). It has also been suggested that E1A binds to the CREB-binding protein, CBP (Arany, Z., W. R. Sellers, D. M. Livingston, and R. Eckner: "E1A-associated p300 and CREB-associated CBP belong to a conserved family of coactivators." *Cell* 77:799, 1994). Human T lymphotropic virus-I (HTLV-1), the retrovirus which causes human T cell leukemia and tropical spastic paresis, also requires CREB/ATF proteins for replication. In this case, the retrovirus produces a protein, Tax, which binds to CREB/ATF proteins and redirects them from their normal cellular binding sites to different DNA sequences (flanked by G- and G-rich sequences) present within the HTLV transcriptional enhancer (Paca-Uccaralertkun, S., L.-J. Zhao, N. Adya, J. V. Cross, B. R. Cullen, I. M. Boros, and C.-Z. Giam: "In vitro selection of DNA elements highly responsive to the human T-cell lymphotropic virus type I transcriptional activator, Tax." *Mol. Cell. Biol.* 14:456, 1994; Adya, N., L.-J. Zhao, W. Huang, I. Boros, and C.-Z. Giam: "Expansion of CREB's DNA recognition specificity by Tax results from interaction with Ala-Ala-Arg at positions 282–284 near the conserved DNA-binding domain of CREB." *Proc. Natl. Acad. Sci. USA* 91:5642, 1994).

SUMMARY OF THE INVENTION

The present invention is based on the finding that certain nucleic acids containing unmethylated cytosine-guanine (CpG) dinucleotides activate lymphocytes in a subject and redirect a subject's immune response from a Th2 to a Th1 (e.g., by inducing monocytic cells and other cells to produce Th1 cytokines, including IL-12, IFN-γ and GM-CSF). Based on this finding, the invention features, in one aspect, novel immunostimulatory nucleic acid compositions.

In one embodiment, the invention provides an isolated immunostimulatory nucleic acid sequence containing a CpG motif represented by the formula:

$$5'N_1X_1CGX_2N_23'$$

wherein at least one nucleotide separates consecutive CpGs; $X_1$ is adenine, guanine, or thymine; $X_2$ is cytosine or thymine; N is any nucleotide and $N_1+N_2$ is from about 0–26 bases with the proviso that $N_1$ and $N_2$ do not contain a CCGG quadmer or more than one CCG or CGG trimer; and the nucleic acid sequence is from about 8–30 bases in length.

In another embodiment, the invention provides an isolated immunostimulatory nucleic acid sequence contains a CpG motif represented by the formula:

$$5'N_1X_1X_2CGX_3X_4N_2C'$$

wherein at least one nucleotide separates consecutive CpGs; $X_1X_2$ is selected from the group consisting of GpT, GpG, GpA, ApT and ApA; $X_3$ $X_4$ is selected from the group consisting of TpT or CpT; N is any nucleotide and $N_1+N_2$ is from about 0–26 bases with the proviso that $N_1$ and $N_2$ do not contain a CCGG quadmer or more than one CCG or CGG trimer; and the nucleic acid sequence is from about 8–30 bases in length.

In another embodiment, the invention provides a method of stimulating immune activation by administering the nucleic acid sequences of the invention to a subject, preferably a human. In a preferred embodiment, the immune activation effects predominantly a Th1 pattern of immune activation.

In another embodiment, the nucleic acid sequences of the invention stimulate cytokine production. In particular, cytokines such as IL-6, IL-12, IFN-γ, TNF-α and GM-CSF are produced via stimulation of the immune system using the nucleic acid sequences described herein. In another aspect, the nucleic acid sequences of the invention stimulate the lytic activity of natural killer cells (NK) and the proliferation of B cells.

In another embodiment, the nucleic acid sequences of the invention are useful as an artificial adjuvant for use during antibody generation in a mammal such as a mouse or a human.

In another embodiment, autoimmune disorders are treated by inhibiting a subject's response to CpG mediated leukocyte activation. The invention provides administration of inhibitors of endosomal acidification such as bafilomycin a, chloroquine, and monensin to ameliorate autoimmune disorders. In particular, systemic lupus erythematosus is treated in this manner.

The nucleic acid sequences of the invention can also be used to treat, prevent or ameliorate other disorders (e.g., a tumor or cancer or a viral, fungal, bacterial or parasitic infection). In addition, the nucleic acid sequences can be administered to stimulate a subject's response to a vaccine. Furthermore, by redirecting a subject's immune response from Th2 to Th1, the claimed nucleic acid sequences can be used to treat or prevent an asthmatic disorder. In addition, the claimed nucleic acid molecules can be administered to a subject in conjunction with a particular allergen as a type of desensitization therapy to treat or prevent the occurrence of an allergic reaction associated with an asthmatic disorder.

Further, the ability of the nucleic acid sequences of the invention described herein to induce leukemic cells to enter the cell cycle supports their use in treating leukemia by increasing the sensitivity of chronic leukemia cells followed by conventional ablative chemotherapy, or by combining the nucleic acid sequences with other immunotherapies.

Other features and advantages of the invention will become more apparent from the following detailed description and claims.

BRIEF DESCRIPTION OF THE FIGURES

FIG. 1A. *E. coli* (●) and calf thymus DNA (■) sequences and LPS (at 10× the concentration of *E. coli* and calf thymus DNA) (♦).

FIG. 1B. Control phosphodiester oligodeoxynucleotide (ODN) 5' ATGGAAGGTCCAGTGTTCTC 3' (SEQ ID NO:1 14) (■) and two phosphodiester CpG ODN 5' ATCGACCTACGTGCGTTCTC 3' (SEQ ID NO:2) (♦) and 5' TCCATAACGTTCCTGATGCT 3' (SEQ ID NO:3) (●).

FIG. 1C. Control phosphorothioate ODN 5' GCTAGATGTTAGCGT 3' (SEQ ID NO:4) (■) and two phosphorothioate CpG ODN 5' GAGAACGTCGACCTTCGAT 3' (SEQ ID NO: 5) (■) and 5' GCATGACGTTGAGCT 3' (SEQ ID NO:6) (●). Data present the mean±standard deviation of triplicates.

*mansoni* egg antigen "SEA" (open circle), many inflammatory cells are present in the lungs. However, when the mice are initially given CpG oligo (SEQ ID NO: 10) along with egg, the inflammatory cells in the lung are not increased by subsequent inhalation of SEA (open triangles).

Figure 10:
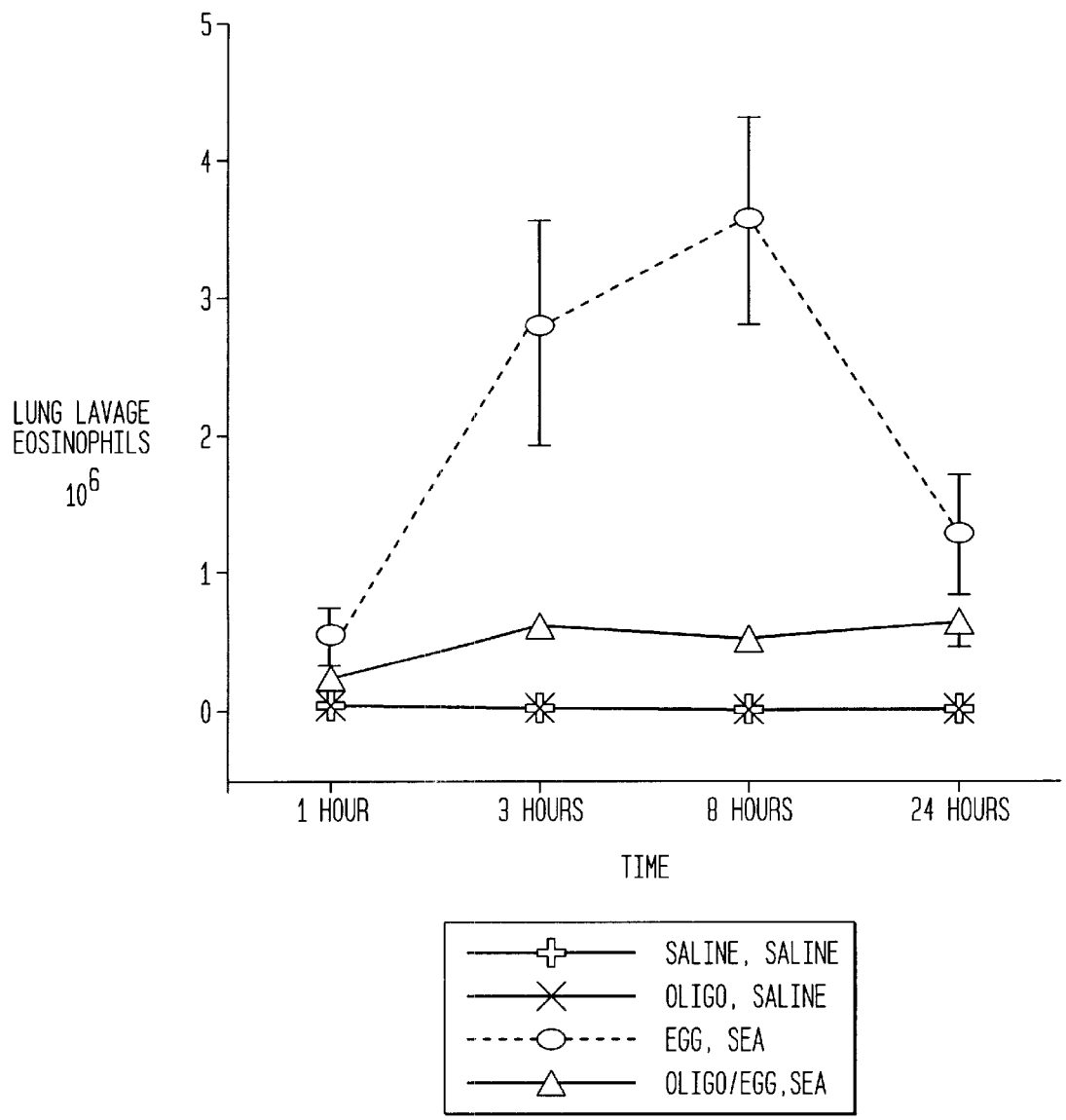

FIG. 10 is a graph plotting lung lavage eosinophil count over time. Again, the graph shows that when the mice are initially injected with egg and subsequently inhale SEA (open circle), many eosinophils are present in the lungs. However, when the mice are initially given CpG oligo (SEQ ID NO: 10) along with egg, the inflammatory cells in the lung are not increased by subsequent inhalation of the SEA (open triangles).

Figure 11:
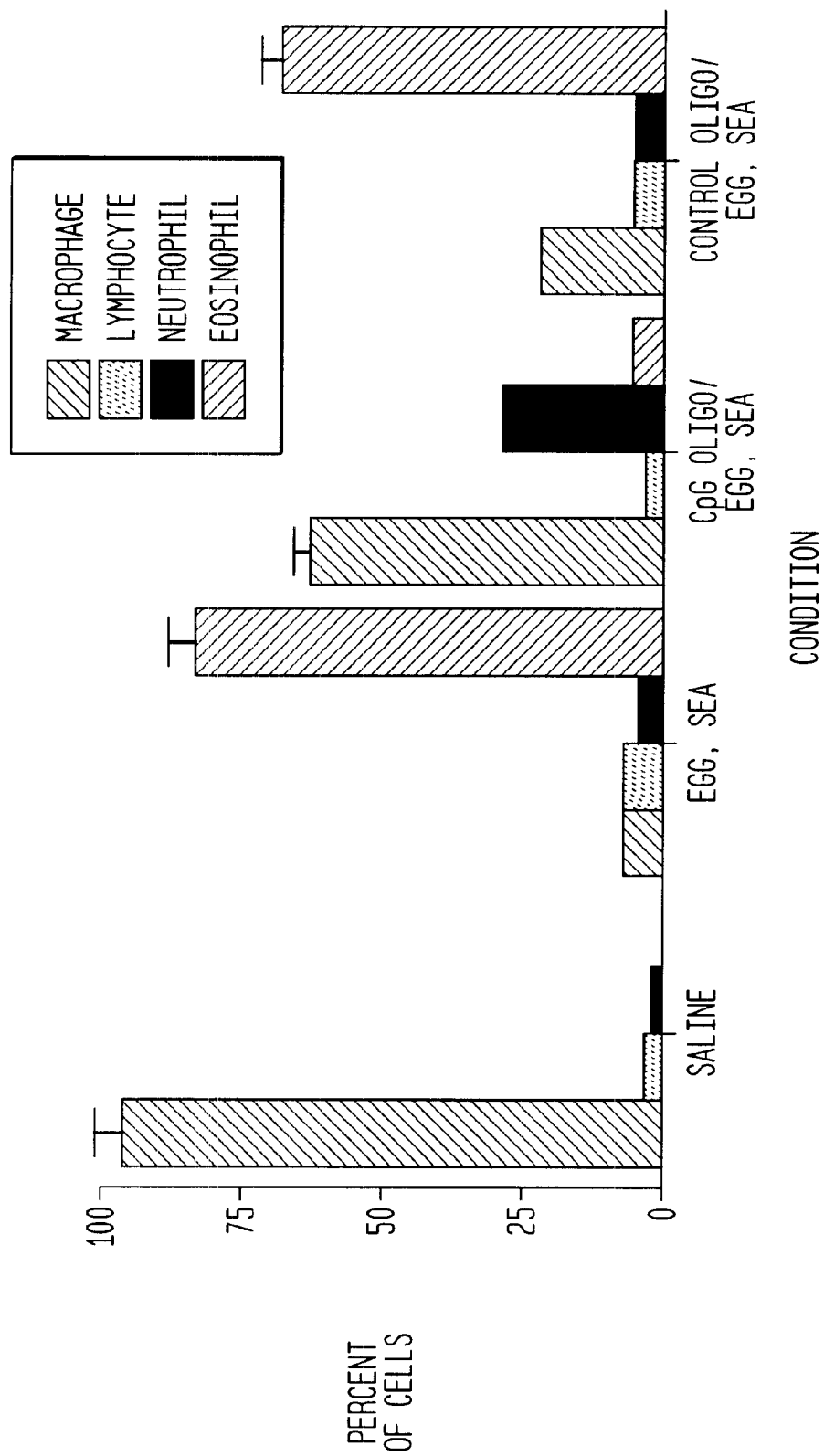

FIG. 11 is a bar graph plotting the effect on the percentage of macrophage, lymphocyte, neutrophil and eosinophil cells induced by exposure to saline alone; egg, then SEA; egg and SEQ ID NO: 11, then SEA; and egg and control oligo (SEQ ID NO: 11), then SEA. When the mice are treated with the control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

Figure 12:
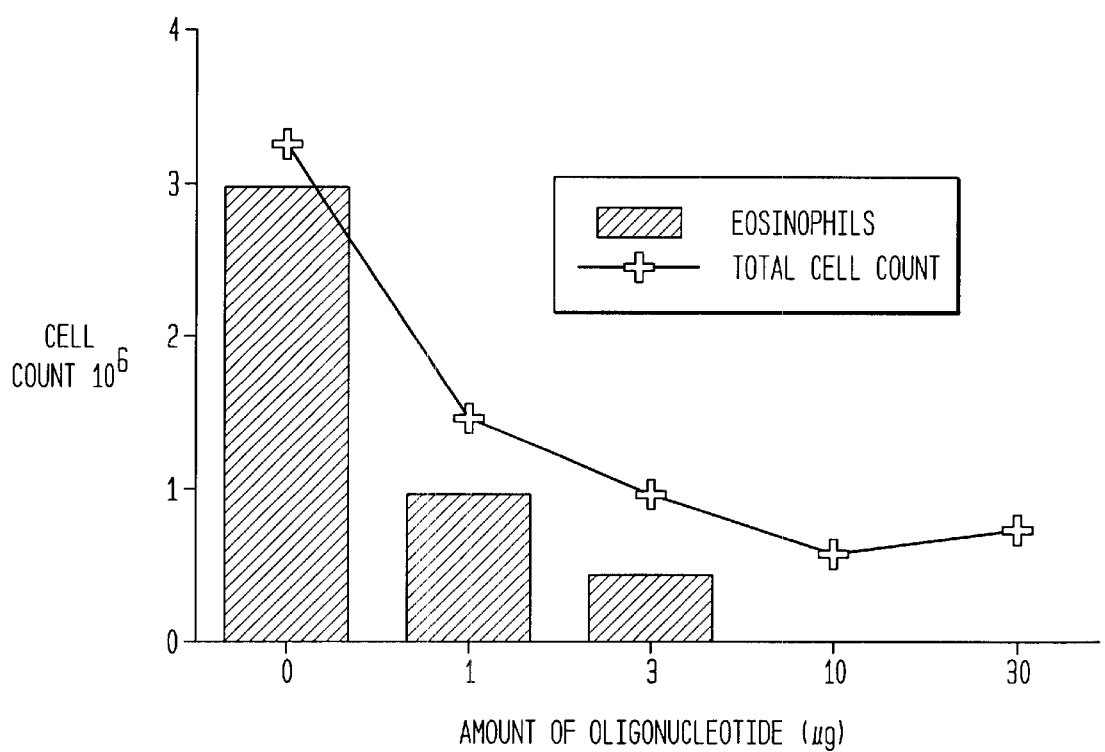

FIG. 12 is a bar graph plotting eosinophil count in response to injection of various amounts of the protective oligo SEQ ID NO: 10.

Figure 13:
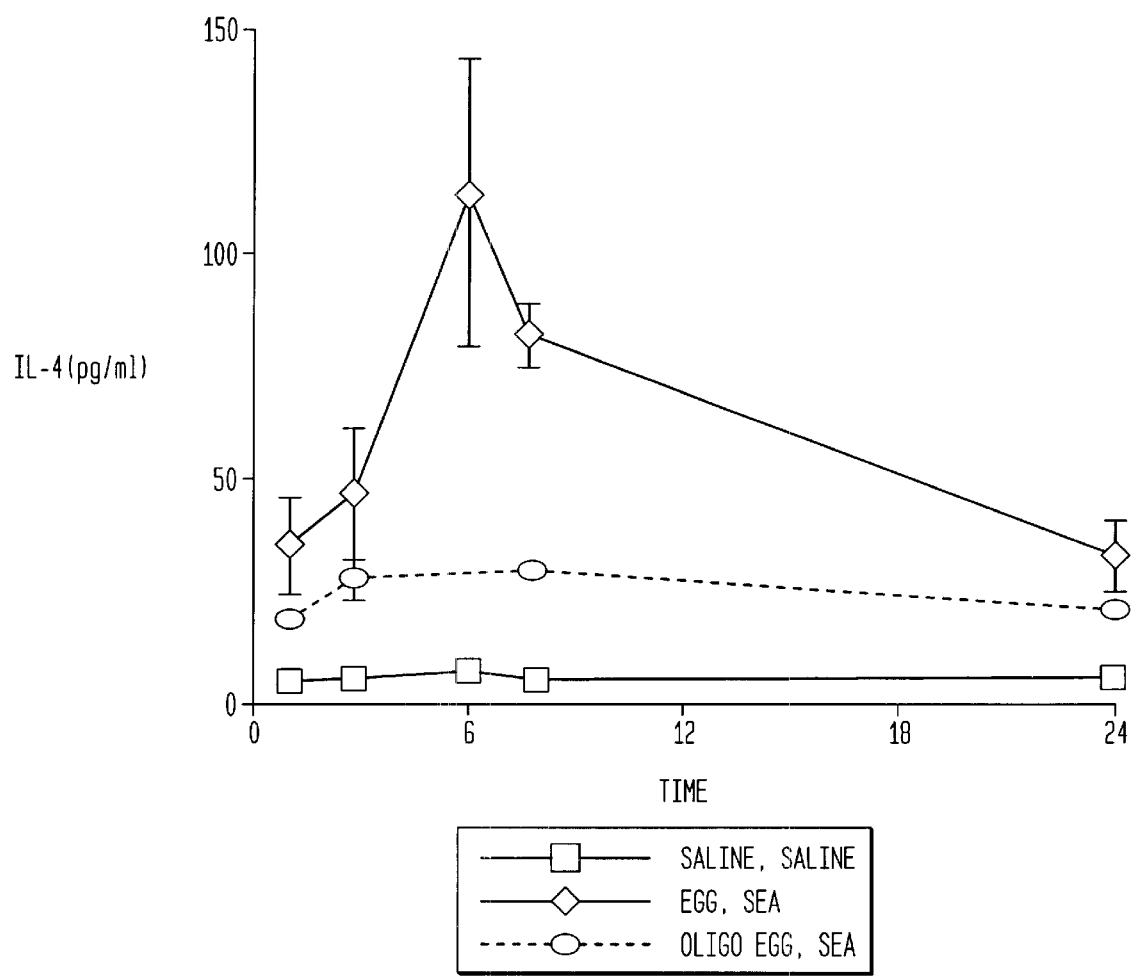

FIG. 13 is a graph plotting interleukin 4 (IL-4) production (pg/ml) in mice over time in response to injection of egg, then SEA (open diamond); egg and SEQ ID NO: 10, then SEA (open circle); or saline, then saline (open square). The graph shows that the resultant inflammatory response correlates with the levels of the Th2 cytokine IL-4 in the lung.

Figure 14:
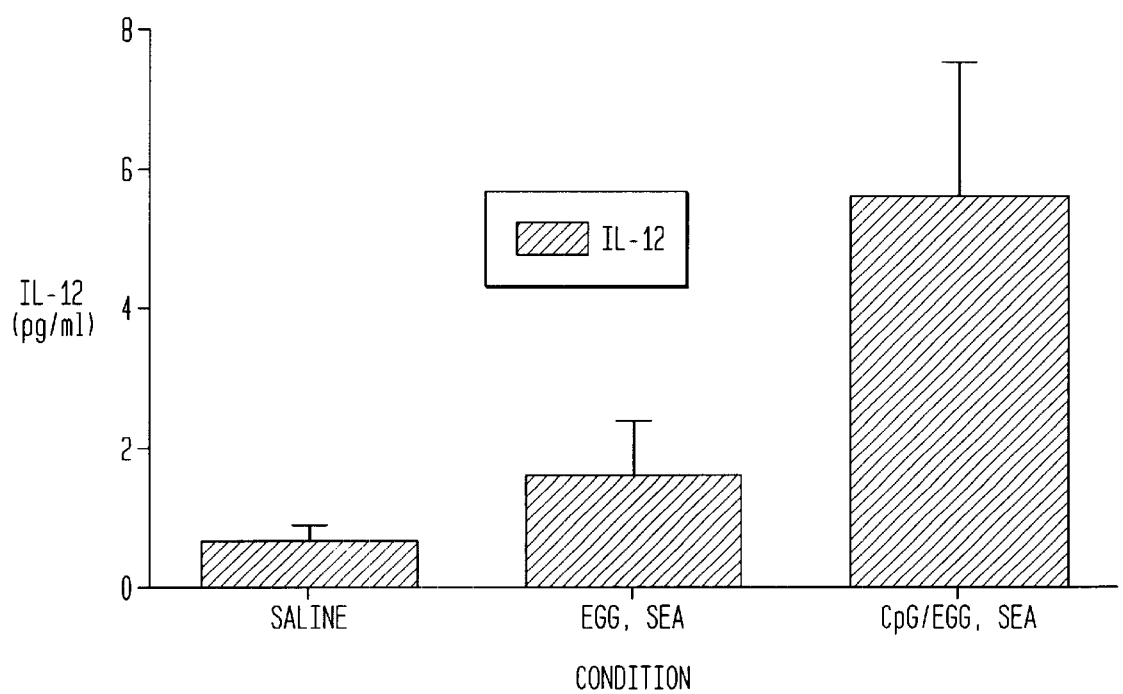

FIG. 14 is a bar graph plotting interleukin 12 (IL-12) production (pg/ml) in mice over time in response to injection of saline; egg, then SEA; or SEQ ID NO. 10 and egg, then SEA. The graph shows that administration of an oligonucleotide containing an unmethylated CpG motif can actually redirect the cytokine response of the lung to production of IL-12, indicating a Th1 type of immune response.

Figure 15:
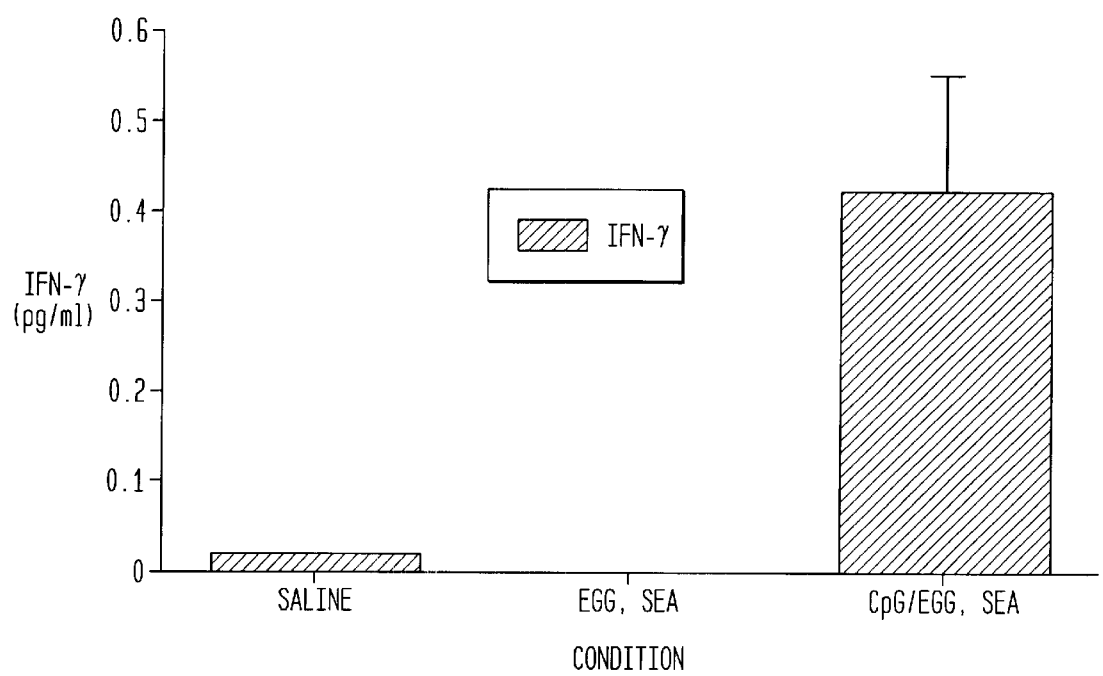

FIG. 15 is a bar graph plotting interferon gamma (IFN-γ) production (pg/ml) in mice over time in response to injection of saline; egg, then saline; or SEQ ID NO: 10 and egg, then SEA. The graph shows that administration of an oligonucleotide containing an unmethylated CpG motif can also redirect the cytokine response of the lung to production of IFN-g, indicating a Th1 type of immune response.

DETAILED DESCRIPTION OF THE INVENTION

Definitions

As used herein, the following terms and phrases shall have the meanings set forth below:

An "allergen" refers to a substance that can induce an allergic asthmatic response in a susceptible subject. The list of allergens is enormous and can include pollens, insect venoms, animal dander dust, fungal spores and drugs (e.g., penicillin). Examples of natural, animal and plant allergens include proteins specific to the following genuses: Canine (*Canis familiaris*); Dermatophagoides (e.g, *Dermatophagoides farinae*); Felis (*Felis domesticus*); Ambrosia (*Ambrosia artemiisfolia;* Lolium (e.g., *Lolium perenne* or *Lolium multiflorum*), Cryptomeria (*Cryptomeria japonica*); Alternaria (*Alternaria alternata*); Alder; Alnus (*Alnus gultinosa*); Betula (*Betula verrucosa*); Quercus (*quercus alba*); Olea (*Olea europa*); Artemisia (*Artemisia vulgaris*); Plantago (e.g., *Plantago lanceolata*); Parietaria (e.g., *Parietaria officinalis* or *Parietaria judaica*); Blattella (e.g., *Blattella germanica*); Apis (e.g., *Apis multiflorum*); Cupressus (e.g., *Cupressus sempervirens, Cupressus arizonica* and *Cupressus macrocarpa*); Juniperus (e.g, *Juniperus sabinoides, Juniperus virginiana, Juniperus communis* and *Juniperus ashei*); Thuya (e.g., *Thuya orientalis*), Chamaecyparis (e.g., *Chamaecyparis obtusa*); Periplaneta (e.g., *Periplaneta americana*); Agropyron (e.g, *Agropyron repens*); Secale (e.g., *Secale cereale*); Triticum (e.g., *Triticum aestivum*); Dactylis (e.g., *Dactylis glomerata*); Festuca (e.g., *Festuca elatior*); Poa (e.g., *Poa pratensis* or *Poa compressa*); Avena (e.g., *Avena sativa*); Holcus (e.g., *Holcus lanatus*); Anthoxanthum (e.g., *Anthoxanthum odoratum*); Arrhenatherum (e.g., *Arrhenatherum elatius*), Agrostis (e.g., *Agrostis alba*); Phleum (e.g, *Phleum pratense*); Phalaris (e.g, *Phalaris arundinacea*); Paspalum (e.g, *Paspalum notatum*); Sorghum (e.g., *Sorghum halepensis*) and Bromus (e.g, *Bromus inermis*).

An "allergy" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

An "immune system deficiency" shall mean a disease or disorder in which the subject's immune system is not functioning in normal capacity or in which it would be useful to boost a subject's immune response for example to eliminate a tumor or cancer (e.g., tumors of the brain, lung (e.g., small cell and non-small cells), ovary, breast, prostate, colon, as well as other carcinomas and sarcomas) or an infection in a subject.

Examples of infectious virus include: Retroviridae (e.g., human immunodeficiency viruses, such as HIV-1, also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g, ebola viruses); Paramyxoviridae (e.g., parainfluenza viruses, mumps virus, measles virus, respiratory syncytial virus); Orthomyxoviridae (e.g., influenza viruses); Bungaviridae (e.g, Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccinia viruses, pox viruses); and Iridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1—internally transmitted; class 2—parenterally transmitted (i.e., Hepatitis C); Norwalk and related viruses, and astroviruses).

Examples of infectious bacteria include: *Helicobacter pyloris, Borelia burgdorferi, Legionella pneumophilia,* Mycobacteria sps (e.g., *M. tuberculosis, M. avium, M. Intracellulare, M. kansaii, M. gordonae*), *Staphylococcus aureus, Neisseria gonorrhoeae, Neisseria meningitidis,* Listeria monocytogenes, Streptococcus pyogenes (Group A Streptococcus), *Streptococcus agalactiae* (Group B Streptococcus), Streptococcus (viridans group), *Streptococcus faecalis, Streptococcus bovis,* Streptococcus (anaerobic sps.), *Streptococcus pneumoniae,* pathogenic Campylobacter sp., Enterococcus sp., *Haemophilus influenzae, Bacillus antracis, corynebacterium diphtheriae,* corynebacterium sp., *Erysipelothrix rhusiopathiae, Clostridium perfringers, Clostridium tetani,* Enterobacter erogenes, *Klebsielia pneuomiae,* Pasturella multicoda, Bacteroides sp., *Fusobacterium nucleatum, Sreptobacillus monitiformis, Treponema pallidium, Treponema pertenue,* Leptospira, and *Actinomeyces israelli*.

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) include: *Plasmodium falciparum* and *Toxoplasma gondii.*

An "immunostimulatory nucleic acid molecule" refers to a nucleic acid molecule, which contains an unmethylated cytosine, guanine dinucleotide sequence (i.e., "CpG DNA" or DNA containing a cytosine followed by guanosine and linked by a phosphate bond) and stimulates (e.g., has a motogenic effect on, or induces or increases cytokine expression by) a vertebrate lymphocyte. An immunostimulatory nucleic acid molecule can be double-stranded or single-stranded. Generally, double-stranded molecules are more stable in vivo, while single-stranded molecules have increased immune activity.

In one preferred embodiment, the invention provides an isolated immunostimulatory nucleic acid sequence containing a CpG motif represented by the formula:

wherein at least one nucleotide separates consecutive CpGs; $X_1$ is adenine, guanine, or thymine; $X_2$ is cytosine or thymine; N is any nucleotide and $N_1+N_2$ is from about 0–26 bases with the proviso that $N_1$ and $N_2$ do not contain a CCGG quadmer or more than one CCG or CGG trimer; and the nucleic acid sequence is from about 8–30 bases in length.

In another embodiment the invention provides an isolated immunostimulatory nucleic acid sequence contains a CpG motif represented by the formula:

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0–26 bases with the proviso that $N_1$ and $N_2$ do not contain a CCGG quadmer or more than one CCG or CGG trimer; and the nucleic acid sequence is from about 8–30 bases in length.

Preferably, the immunostimulatory nucleic acid sequences of the invention include $X_1X_2$ selected from the group consisting of GpT, GpG, GpA and ApA and $X_3X_4$ is selected from the group consisting of TpT, CpT and GpT (see for example, Table 5). For facilitating uptake into cells, CpG containing immunostimulatory nucleic acid molecules are preferably in the range of 8 to 30 bases in length. However, nucleic acids of any size (even many kb long) are immunostimulatory if sufficient immunostimulatory motifs are present, since such larger nucleic acids are degraded into oligonucleotides inside of cells. Preferred synthetic oligonucleotides do not include a CGG quadmer or more than one CCG or CGG trimer at or near the 5' and/or 3' terminals and/or the consensus mitogenic CpG motif is not a palindrome. Prolonged immunostimulation can be obtained using stabilized oligonucleotides, where the oligonucleotide incorporates a phosphate backbone modification. For example, the modification is a phosphorothioate or phosphorodithioate modification. More particularly, the phosphate backbone modification occurs at the 5' end of the nucleic acid for example, at the first two nucleotides of the 5' end of the nucleic acid. Further, the phosphate backbone modification may occur at the 3' end of the nucleic acid for example, at the last five nucleotides of the 3' end of the nucleic acid.

Preferably the immunostimulatory CpG DNA is in the range of between 8 to 30 bases in size when it is an oligonucleotide. Alternatively, CpG dinucleotides can be produced on a large scale in plasmids, which after being administered to a subject are degraded into oligonucleotides. Preferred immunostimulatory nucleic acid molecules (e.g., for use in increasing the effectiveness of a vaccine or to treat an immune system deficiency by stimulating an antibody (i.e., humoral) response in a subject) have a relatively high stimulation index with regard to B cell, monocyte and/or natural killer cell responses (e.g., cytokine, proliferative, lytic or other responses).

The nucleic acid sequences of the invention stimulate cytokine production in a subject for example. Cytokines include but are not limited to IL-6, IL-12, IFN-γ, TNF-α and GM-CSF. Exemplary sequences include: TCCATGTCGCTCCTGATGCT (SEQ ID NO: 37), TCCATGTCGTTCCTGATGCT (SEQ ID NO: 38), and TCGTCGTTTTGTCGTTTTGTCGTT (SEQ ID NO: 46).

The nucleic acid sequences of the invention are also useful for stimulating natural killer cell (NK) lytic activity in a subject such as a human. Specific, but non-limiting examples of such sequences include: TCGTCGTTGTCGTTGTCGTT (SEQ ID NO: 47), TCGTCGTTTTGTCGTTTTGTCGTT (SEQ ID NO: 46), TCGTCGTTGTCGTTTTGTCGTT (SEQ ID NO: 49), GCGTGCGTTGTCGTTGTCGTT (SEQ ID NO: 56), TGTCGTTTGTCGTTTGTCGTT (SEQ ID NO: 48), TGTCGTTGTCGTTGTCGTT (SEQ ID NO: 50) and TCGTCGTCGTCGTT (SEQ ID NO: 51).

The nucleic acid sequences of the invention are useful for stimulating B cell proliferation in a subject such as a human. Specific, but non-limiting examples of such sequences include: TCCTGTCGTTCCTTGTCGTT (SEQ ID NO: 52), TCCTGTCGTTTTTTGTCGTT (SEQ ID NO: 53), TCGTCGCTGTCTGCCCTTCTT (SEQ ID NO: 54), TCGTCGCTGTTGTCGTTTCTT (SEQ ID NO: 55), TCGTCGTTTTGTCGTTTTGTCGTT (SEQ ID NO: 46), TCGTCGTTGTCGTTTTGTCGTT (SEQ ID NO: 49) and TGTCGTTGTCGTTGTCGTT (SEQ ID NO: 50).

In another aspect, the nucleic acid sequences of the invention are useful as an adjuvant for use during antibody production in a mammal. Specific, but non-limiting examples of such sequences include: TCCATGACGTTCCTGACGTT (SEQ ID NO: 10), GTCGTT (SEQ. ID. NO: 57), GTCGCT (SEQ. ID. NO.58), TGTCGCT (SEQ. ID. NO: 101) and TGTCGTT (SEQ. ID. NO: 102). Furthermore, the claimed nucleic acid sequences can be administered to treat or prevent the symptoms of an asthmatic disorder by redirecting a subject's immune response from Th2 to Th 1. An exemplary sequence includes TCCATGACGTTCCT-GACGTT (SEQ ID NO: 10).

The stimulation index of a particular immunostimulatory CpG DNA can be tested in various immune cell assays. Preferably, the stimulation index of the immunostimulatory CpG DNA with regard to B-cell proliferation is at least about 5, preferably at least about 10, more preferably at least about 15 and most preferably at least about 20 as determined by incorporation of $^3$H uridine in a murine B cell culture, which has been contacted with a 20 $\mu$M of ODN for 20 h at 37° C. and has peen pulsed with 1 $\mu$Ci of $^3$H uridine; and harvested and counted 4 h later as described in detail in Example 1. For use in vivo, for example to treat an immune system deficiency by stimulating a cell-mediated (local) immune response in a subject, it is important that the immunostimulatory CpG DNA be capable of effectively inducing cytokine secretion by monocytic cells and/or Natural Killer (NK) cell lytic activity.

Preferred immunostimulatory CpG nucleic acids should effect at least about 500 pg/ml of TNF-$\alpha$, 15 pg/ml IFN-$\gamma$, 70 pg/ml of GM-CSF 275 pg/ml of IL-6, 200 pg/ml IL-12, depending on the therapeutic indication, as determined by the assays described in Example 12. Other preferred immunostimulatory CpG DNAs should effect at least about 10%, more preferably at least about 15% and most preferably at least about 20% YAC-1 cell specific lysis or at least about 30, more preferably at least about 35 and most preferably at least about 40% 2C11 cell specific lysis as determined by the assay described in detail in Example 4.

A "nucleic acid" or "DNA" means multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the term refers to ribonucleotides as well as oligodeoxyribonucleotides. The term shall also include polynucleotides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by oligonucleotide synthesis).

A "nucleic acid delivery complex" shall mean a nucleic acid molecule associated with (e.g., ionically or covalently bound to; or encapsulated within) a targeting means (e.g., a molecule that results in higher affinity binding to target cell (e.g., B-cell and natural killer (NK) cell) surfaces and/or increased cellular uptake by target cells). Examples of nucleic acid delivery complexes include nucleic acids associated with: a sterol (e.g., a ligand recognized by target cell specific receptor). Preferred complexes must be sufficiently stable in vivo to prevent significant uncoupling prior to internalization by the target cell. However, the complex should be cleavable under appropriate conditions within the cell so that the nucleic acid is released in a functional form.

"Palindromic sequences" shall mean an inverted repeat (i.e., a sequence such as ABCDEE'D'C'B'A' in which A and A' are bases capable of forming the usual Watson-Crick base pairs. In vivo, such sequences may form double stranded structures.

A "stabilized nucleic acid molecule" shall mean a nucleic acid molecule that is relatively resistant to in vivo degradation (e.g., via an exo- or endo-nuclease). Stabilization can be a function of length or secondary structure. Unmethylated CpG containing nucleic acid molecules that are tens to hundreds of kbs long are relatively resistant to in vivo degradation. For shorter immunostimulatory nucleic acid molecules, secondary structure can stabilize and increase their effect. For example, if the 3' end of a nucleic acid molecule has self-complementarily to an upstream region, so that it can fold back and form a sort of stem loop structure, then the nucleic acid molecule becomes stabilized and therefore exhibits more activity.

Preferred stabilized nucleic acid molecules of the instant invention have a modified backbone. For use in immune stimulation, especially preferred stabilized nucleic acid molecules are phosphorothioate (i.e., at least one of the phosphate oxygens of the nucleic acid molecules is replaced by sulfur) or phosphorodithioate modified nucleic acid molecules. More particularly, the phosphate backbone modification occurs at the 5' end of the nucleic acid for example, at the first two nucleotides of the 5' end of the nucleic acid. Further, the phosphate backbone modification may occur at the 3' end of the nucleic acid for example, at the last five nucleotides of the 3' end of the nucleic acid. In addition to stabilizing nucleic acid molecules, as reported further herein, phosphorothioate-modified nucleic acid molecules (including phosphorodithioate-modified) can increase the extent of immune stimulation of the nucleic acid molecule, which contains an unmethylated CpG dinucleotide as shown herein. International Patent Application Publication Number WO 95/26204 entitled "Immune Stimulation By Phosphorothioate Oligonucleotide Analogs" also reports on the nonsequence specific immunostimulatory effect of phosphorothioate modified oligonucleotides. As reported herein, unmethylated CpG containing nucleic acid molecules having a phosphorothioate backbone have been found to preferentially activate B-cell activity, while unmethylated CpG containing nucleic acid molecules having a phosphodiester backbone have been found to preferentially activate monocytic (macrophages, dendritic cells and monocytes) and NK cells. Phosphorothioate CpG oligonucleotides with preferred human motifs are also strong activators of monocytic and NK cells.

Other stabilized nucleic acid molecules include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Nucleic acid molecules which contain a diol, such as tetraethylenglycol or hexaethyleneglycol, at either or both termini have also been shown to be substantially resistant to nuclease degradation.

A "subject" shall mean a human or vertebrate animal including a dog, cat, horse, cow, pig, sheep, goat, chicken, monkey, rat, and mouse.

As used herein, the term "vector" refers to a nucleic acid molecule capable of transporting another nucleic acid to which it has been linked. Preferred vectors are those capable of autonomous replication and expression of nucleic acids to which they are linked (e.g., an episome). Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Certain Unmethylated CpG Containing Nucleic Acids Have B Cell Stimulatory Activity as Shown in vitro and in vivo In the course of investigating the lymphocyte stimulatory effects of two antisense oligonucleotides specific for endogenous retroviral sequences, using protocols described in the attached Examples 1 and 2, it was surprisingly found that two out of twenty-four "controls" (including various scrambled, sense, and mismatch controls for a panel of "antisense" ODN) also mediated B cell activation and IgM secretion, while the other "controls" had no effect.

Two observations suggested that the mechanism of this B cell activation by the "control" ODN may not involve antisense effects 1) comparison of vertebrate DNA sequences listed in GenBank showed no greater homology than that seen with non-stimulatory ODN and 2) the two controls showed no hybridization to Northern blots with 10 μg of spleen poly A+ RNA. Resynthesis of these ODN on a different synthesizer or extensive purification by polyacrylamide gel electrophoresis or high pressure liquid chromatography gave identical stimulation, eliminating the possibility of an impurity. Similar stimulation was seen using B cells from C3H/HeJ mice, eliminating the possibility that lipopolysaccharide (LPS) contamination could account for the results.

The fact that two "control" ODN caused B cell activation similar to that of the two "antisense" ODN raised the possibility that all four ODN were stimulating B cells through some non-antisense mechanism involving a sequence motif that was absent in all of the other nonstimulatory control ODN. In comparing these sequences, it was discovered that all of the four stimulatory ODN contained CpG dinucleotides that were in a different sequence context from the nonstimulatory control.

To determine whether the CpG motif present in the stimulatory ODN was responsible for the observed stimulation, over 300 ODN ranging in length from 5 to 42 bases that contained methylated, unmethylated, or no CpG dinucleotides in various sequence contexts were synthesized. These ODNs, including the two original "controls" (ODN 1 and 2) and two originally synthesized as "antisense" (ODN 3D and 3M; Krieg, A. M. *J. Immunol.* 143:2448 (1989)), were then examined for in vitro effects on spleen cells (representative sequences are listed in Table 1). Several ODN that contained CpG dinucleotides induced B cell activation and IgM secretion; the magnitude of this stimulation typically could be increased by adding more CpG dinucleotides (Table 1; compare ODN 2 to 2a or 3D to 3Da and 3Db). Stimulation did not appear to result from an antisense mechanism or impurity. ODN caused no detectable proliferation of γδ or other T cell populations.

Mitogenic ODN sequences uniformly became nonstimulatory if the CpG dinucleotide was mutated (Table 1; compare ODN 1 to 1a; 3D to 3Dc; 3M to 3Ma; and 4 to 4a) or if the cytosine of the CpG dinucleotide was replaced by 5-methylcytosine (Table 1; ODN 1b, 2b, 3Dd, and 3Mb). Partial methylation of CpG motifs caused a partial loss of stimulatory effect (compare 2a to 2c, Table 1). In contrast, methylation of other cytosines did not reduce ODN activity (ODN 1c, 2d, 3De and 3Mc). These data confirmed that CpG motif is the essential element present in ODN that activate B cells.

In the course of these studies, it became clear that the bases flanking the CpG dinucleotide played an important role in determining the murine B cell activation induced by an ODN. The optimal stimulatory motif was determined to consist of a CpG flanked by two 5' purines (preferably a GpA dinucleotide) and two 3' pyrimidines (preferably a TpT or TpC dinucleotide). Mutations of ODN to bring the CpG motif closer to this ideal improved stimulation (e.g., Table 1, compare ODN 2 to 2e; 3M to 3Md) while mutations that disturbed the motif reduced stimulation (e.g., Table 1, compare ODN 3D to 3Df; 4 to 4b, 4c and 4d). On the other hand, mutations outside the CpG motif did not reduce stimulation (e.g., Table 1, compare ODN to 1d; 3D to 3Dg; 3M to 3Me). For activation of human cells, the best flanking bases are slightly different (See Table 5)).

Of those tested, ODNs shorter than 8 bases were non-stimulatory (e.g., Table 1, ODN 4e). Among the forty-eight 8 base ODN tested, a highly stimulatory sequence was identified as TCAACGTT (SEQ. ID. NO: 90) (ODN4) which contains the self complementary "palindrome" AACGTT (SEQ. ID. NO: 105). In further optimizing this motif, it was found that ODN containing Gs at both ends showed increased stimulation, particularly if the ODN were rendered nuclease resistant by phosphorothioate modification of the terminal internucleotide linkages. ODN 1585 (5'GGGGTCAACGTTGAGGGGGG 3' (SEQ ID NO:12)), in which the first two and last five internucleotide linkages are phosphorothioate modified caused an average 25.4 fold increase in mouse spleen cell proliferation compared to an average 3.2 fold increase in proliferation included by ODN 1638, which has the same sequence as ODN 1585 except that the 10 Gs at the two ends are replaced by 10 As. The effect of the G-rich ends is cis; addition of an ODN with poly G ends but no CpG motif to cells along with 1638 gave no increased proliferation. For nucleic acid molecules longer than 8 base pairs, non-palindromic motifs containing an unmethylated CpG were found to be more immunostimulatory.

TABLE 1

| ODN | | Sequence (5' to 3')† | Stimulation Index' | |
|---|---|---|---|---|
| | | | ³H Uridine | IgM Production |
| 1 | (SEQ ID NO:89) | GCTAGACGTTAGCGT | 6.1 ± 0.8 | 17.9 ± 3.6 |
| 1a | (SEQ ID NO:4) | ......T......... | 1.2 ± 0.2 | 1.7 ± 0.5 |
| 1b | (SEQ ID NO:13) | ......Z......... | 1.2 ± 0.1 | 1.8 ± 0.0 |
| 1c | (SEQ ID NO:14) | ..........Z.. | 10.3 ± 4.4 | 9.5 ± 1.8 |
| 1d | (SEQ ID NO:6) | ..AT......GAGC. | 13.0 ± 2.3 | 18.3 ± 7.5 |
| 2 | (SEQ ID NO:1) | ATGGAAGGTCCAGCGTTCTC | 2.9 ± 0.2 | 13.6 ± 2.0 |
| 2a | (SEQ ID NO:15) | ..C..CTC..G......... | 7.7 ± 0.8 | 24.2 ± 3.2 |
| 2b | (SEQ ID NO:16) | ..Z..CTC.ZG...Z...... | 1.6 ± 0.5 | 2.8 ± 2.2 |
| 2c | (SEQ ID NO:17) | ..Z..CTC..G......... | 3.1 ± 0.6 | 7.3 ± 1.4 |
| 2d | (SEQ ID NO:18) | ..C..CTC..G......Z.. | 7.4 ± 1.4 | 27.7 ± 5.4 |
| 2e | (SEQ ID NO:19) | ...........A....... | 5.6 ± 2.0 | ND |

TABLE 1-continued

| ODN | Sequence (5' to 3')† | Stimulation Index' | |
|---|---|---|---|
| | | ³H Uridine | IgM Production |
| 3D (SEQ ID NO:20) | GAGAACGCTGGACCTTCCAT | 4.9 ± 0.5 | 19.9 ± 3.6 |
| 3Da (SEQ ID NO:21) | .......:..C.......... | 6.6 ± 1.5 | 33.9 ± 6.8 |
| 3Db (SEQ ID NO:22) | .......:..C......G.. | 10.1 ± 2.8 | 25.4 ± 0.8 |
| 3Dc (SEQ ID NO:23) | ...C.A.............. | 1.0 ± 0.1 | 1.2 ± 0.5 |
| 3Dd (SEQ ID NO:24) | .....Z.............. | 1.2 ± 0.2 | 1.0 ± 0.4 |
| 3De (SEQ ID NO:25) | .......:.......Z...... | 4.4 ± 1.2 | 18.8 ± 4.4 |
| 3Df (SEQ ID NO:26) | .......:..A.......... | 1.6 ± 0.1 | 7.7 ± 0.4 |
| 3Dg (SEQ ID NO:27) | .......:..CC.G.ACTG.. | 6.1 ± 1.5 | 18.6 ± 1.5 |
| 3M (SEQ ID NO:28) | TCCATGTCGGTCCTGATGCT | 4.1 ± 0.2 | 23.2 ± 4.9 |
| 3Ma (SEQ ID NO:29) | ......CT............ | 0.9 ± 0.1 | 1.8 ± 0.5 |
| 3Mb (SEQ ID NO:30) | ........Z............ | 1.3 ± 0.3 | 1.5 ± 0.6 |
| 3Mc (SEQ ID NO:31) | ...........:..Z........ | 5.4 ± 1.5 | 8.5 ± 2.6 |
| 3Md (SEQ ID NO:7) | ......A..T.......... | 17.2 ± 9.4 | ND |
| 3Me (SEQ ID NO:32) ....... ..:......C..A. | | 3.6 ± 0.2 | 14.2 ± 5.2 |
| 4 (SEQ ID NO:90) | TCAACGTT | 6.1 ± 1.4 | 19.2 ± 5.2 |
| 4a (SEQ ID NO:91) | ....GC.. | 1.1 ± 0.2 | 1.5 ± 1.1 |
| 4b (SEQ ID NO:92) | ...GCGC. | 4.5 ± 0.2 | 9.6 ± 3.4 |
| 4c (SEQ ID NO:93) | ...TCGA. | 2.7.± 1.0 | ND |
| 4d (SEQ ID NO:94) | ..TT..AA | 1.3 ± 0.2 | ND |
| 4e (Residue 2–8 of SEQ ID NO:90; SEQ ID NO:106) | -...:.. | 1.3 ± 0.2 | 1.1 ± 0.5 |
| 4f (SEQ ID NO:95) | C...:.. | 3.9 ± 1.4 | ND |
| 4g (Residue 11–18 of SEQ ID NO:19; SEQ ID NO:117) | --...:..CT | 1.4 ± 0.3 | ND |
| 4h (SEQ ID NO:96) | ......:.C | 1.2 ± 0.2 | ND |

'Stimulation indexes are the means and std. dev. derived from at least 3 separate experiments, and are compared to wells cultured with no added ODN. ND = not done. CpG dinucleotides are underlined. Dots indicate identity; dashes indicate deletions. Z = 5 methyl cytosine.

TABLE 2

Identification of the optimal CpG motif for Murine IL-6 production and B cell activation.

| ODN | SEQUENCE (5'–3') | IL-6 (pg/ml)[a] | | SI[b] | IgM (ng/ml)[c] |
|---|---|---|---|---|---|
| | | CH12.LX | SPLENIC B CELL | | |
| 512 (SEQ ID No:28) | TCCATGTCGGTCCTGATGCT | 300 ± 106 | 627 ± 43 | 5.8 ± 0.3 | 7315 ± 1324 |
| 1637 (SEQ ID No:33) | .......C........... | 136 ± 27 | 46 ± 6 | 1.7 ± 0.2 | 770 ± 72 |
| 1615 (SEQ ID No:34) | .......G........... | 1201 ± 155 | 850 ± 202 | 3.7 ± 0.3 | 3212 ± 617 |
| 1614 (SEQ ID No:35) | .......A........... | 1533 ± 321 | 1812 ± 103 | 10.8 ± 0.6 | 7558 ± 414 |
| 1636 (SEQ ID No:36) | ........:.A......... | 1181 ± 76 | 947 ± 132 | 5.4 ± 0.4 | 3983 ± 485 |
| 1634 (SEQ ID No:37) | ........:.C......... | 1049 ± 223 | 1671 ± 175 | 9.2 ± 0.9 | 6256 ± 261 |
| 1619 (SEQ ID No:38) | ........:.T......... | 1555 ± 304 | 2908 ± 129 | 12.5 ± 1.0 | 8243 ± 698 |
| 1618 (SEQ ID No:7) | ......A..T......... | 2109 ± 291 | 2596 ± 166 | 12.9 ± 0.7 | 10425 ± 674 |
| 1639 (SEQ ID No:3) | .....AA..T......... | 1827 ± 83 | 2012 ± 132 | 11.5 ± 0.4 | 9489 ± 103 |
| 1707 (SEQ ID No:39) | .......A..TC........ | ND | 1147 ± 175 | 4.0 ± 0.2 | 3534 ± 217 |
| 1708 (SEQ ID No:40) | .....CA..TG......... | ND | 59 ± 3 | 1.5 ± 0.1 | 466 ± 109 |

Dots indicate identity; CpG dinucleotides are underlined; ND = not done
[a]The experiment was done at least three times with similar results. The level of IL-6 of unstimulated control cultures of both CH12.LX and splenic B cells was ≦10 pg/ml. The IgM level of unstimulated culture was 547 ± 82 ng/ml. CpG dinucleotides are underlined and dots indicate identity. Cells were stimulated with 20 µM of various CpG O-ODN. Data present the mean ± SD of triplicates.
[b][³H] Uridine uptake was indicated as a fold increase (SI: stimulation index) from unstimulated control (2322.67 ± 213.68 cpm).
[c]Measured by ELISA.

Other octamer ODN containing a 6 base palindrome with a TpC dinucleotide at the 5' end were also active (e.g., Table 1, ODN 4b, 4c). Other dinucleotides at the 5' end gave reduced stimulation (e.g., ODN 4f, all sixteen possible dinucleotides were tested). The presence of a 3' dinucleotide was insufficient to compensate for the lack of a 5' dinucleotide (e.g., Table 1, ODN 4g). Disruption of the palindrome eliminated stimulation in octamer ODN (e.g., Table 1, ODN 4h), but palindromes were not required in longer ODN.

The kinetics of lymphocyte activation were investigated using mouse spleen cells. When the cells were pulsed at the same time as ODN addition and harvested just four hours later, there was already a two-fold increase in $^3$H uridine incorporation. Stimulation peaked at 12–48 hours and then decreased. After 24 hours, no intact ODN were detected, perhaps accounting for the subsequent fall in stimulation when purified B cells with or without anti-IgM (at a submitogenic dose) were cultured with CpG ODN, proliferation was found to synergistically increase about 10-fold by the two mitogens in combination after 48 hours. The magnitude of stimulation was concentration dependent and consistently exceeded that of LPS under optimal conditions for both. Oligonucleotides containing a nuclease resistant phosphorothioate backbone were approximately two hundred times mor potent than unmodified oligonucleotides.

Cell cycle analysis was used to determine the proportion of B cells activated by CpG-ODN. CpG-ODN induced cycling in more than 95% of B cells. Splenic B lymphocytes sorted by flow cytometry into CD23– (marginal zone) and CD23+ (follicular) subpopulations were equally responsive to ODN-induced stimulation, as were both resting and activated populations of B cells isolated by fractionation over Percoll gradients. These studies demonstrated that CpG-ODN induced essentially all B cells to enter the cell cycle.

Immunostimulatory Nucleic Acid Molecules Block Murine B Cell Apoptosis

Certain B cell lines, such as WEHI-231, are induced to undergo growth arrest and/or apoptosis in response to crosslinking of their antigen receptor by anti-IgM (Jakway, J. P. et al., "Growth regulation of the B lymphoma cell line WEHI-231 by anti-immunoglobulin, lipopolysaccharide and other bacterial products" *J. Immunol.* 137: 2225 (1986); Tsubata, T., J. Wu and T. Honjo: B-cell apoptosis induced yb antigen receptor crosslinking is blocked by a T-cell signal through CD40." *Nature* 365: 645 (1993)). WEHI-231 cells are rescued from this growth arrest by certain stimuli such as LPS and by the CD40 ligand. ODN containing the CpG motif were also found to protect WEHI-231 from anti-IgM induced growth arrest, indicating that accessory cell populations are not required for the effect. Subsequent work indicates that CpG ODN induce Bcl-x and myc expression, which may account for the protection from apoptosis. Also, CpG nucleic acids have been found to block apoptosis in human cells. This inhibition of apoptosis is important, since it should enhance and prolong immune activation by CpG DNA.

Identification of the Optimal CpG Motif for Induction of Murine IL-6 and IgM Secretion and B Cell Proliferation To evaluate whether the optimal B cell stimulatory CpG motif was identical with the optimal CpG motif for IL-6 secretion, a panel of ODN in which the bases flanking the CpG dinucleotide were progressively substituted was studied. This ODN panel was analyzed for effects on B cell proliferation, Ig production, and IL-6 secretion, using both splenic B cells and CH12.LX cells. As shown in Table 2, the optimal stimulatory motif contains an unrmethylated CpG flanked by two 5' purines and two 3' pyrimidines. Generally a mutation of either 5' purines to C were especially deleterious, but changes in 5' purines to T or 3' pyrimidines to purines had less marked effects. Based on analyses of these and scores of other ODN, it was determined that the optimal CpG motif for induction of IL-6 secretion is TGACGTT (SEQ. ID. NO: 108), which is identical with the optimal mitogenic and IgM-inducing CpG motif (Table 2). This motif was more stimulatory than any of the palindrome containing sequences studied (1639, 1707 and 1708).

Induction of Murine Cytokine Secretion by CpG Motifs in Bacterial DNA or Oligonucleotides As described in Example 9, the amount of IL-6 secreted by spleen cells after CpG DNA stimulation was measured by ELISA. T cell depleted spleen cell cultures rather than whole spleen cells were used for in vitro studies following preliminary studies showing that T cells contribute little or nothing to the IL-6 produced by CpG DNA-stimulated spleen cells. As shown in Table 3, IL-6 production was markedly increased in cells cultured with *E. coli* DNA but not in cells cultured with calf thymus DNA. To confirm that the increased IL-6 production observed with *E. coli* DNA was not de to contamination by other bacterial products, the DNA was digested with DNAse prior to analysis. DNAse pretreatment abolished IL-6 production induced by *E. coli* DNA (Table 3). In addition, spleen cells from LPS-nonresponsive C2H/HeJ mouse produced similar levels of IL-6 in response to bacterial DNA. To analyze whether the IL-6 secretion induced by *E. coli* DNA was mediated by the unmethylated CpG dinucleotides in bacterial DNA, methylated *E. coli* DNA and a panel of synthetic ODN were examined. As shown in Table 3, CpG ODN significantly induced IL-6 secretion (ODN 5a, 5b, 5c) while CpG methylated *E. coli* DNA, or ODN containing methylated CpG (ODN 5f) or no CpG (ODN 5d) did not. Changes at sites other than CpG dinucleotides (ODN 5b) or methylation of other cytosines (ODN 5g) did not reduce the effect of CpG ODN. Methylation of a single CpG in an ODN with three CpGs resulted in a partial reduction in the stimulation (compare ODN 5c to 5e; Table 3).

TABLE 3

Induction of Murine IL-6 secretion by CpG motifs in bacterial DNA or oligonucleotides.

| Treatment | | IL-6 (pg/ml) |
|---|---|---|
| calf thymus DNA | | ≦10 |
| calf thymus DNA + DNase | | ≦10 |
| E. coli DNA | | 1169.5 ± 94.1 |
| E. coli DNA + DNase | | ≦10 |
| CpG methylated E. coli DNA | | ≦10 |
| LPS | | 280.1 ± 17.1 |
| Media (no DNA) | | ≦10 |
| 5a SEQ. ID. No:115 | ATGGACTCTCCAGCGTTCTC | 1096.4 ± 372.0 |
| 5b SEQ. ID. No:19 | .....AGG....A........ | 1124.5 ± 126.2 |
| 5c SEQ. ID. No:15 | ..C.......G.......... | 1783.0 ± 189.5 |
| 5d SEQ. ID. No:114 | .... AGG..C..T...... | ≦10 |
| 5e SEQ. ID. No:116 | ..C.......G...Z...... | 851.1 ± 114.4 |
| 5f SEQ. ID. No:16 | ..Z......ZG...Z...... | ≦10 |
| 5g SEQ. ID. No:18 | ..C.......G.......Z.. | 1862.3 ± 87.26 |

T cell depleted spleen cells from DBA/2 mice were stimulated with phosphodiester modified oligonucleotides (O-ODN) (20 μM), calf thymus DNA (50 μg/ml) or E. coli DNA (50 μg/ml) with or without enzyme treatment, or LPS (10 μg/ml) for 24 hr. Data represent the mean (pg/ml) ± SD of triplicates. CpG dinucleotides are underlined and dots indicate identity. Z indicates 5-methylcytosine.

CpG Motifs can be Used as an Artificial Adjuvant

Nonspecific simulators of the immune response are known as adjuvants. The use of adjuvants is essential to induce a strong antibody response to soluble antigens (Harlow and Lan, *Antibodies: A Laboratory manual*, Cold Spring harbor, N.Y. Current Edition; hereby incorporated by reference). The overall effect of adjuvants is dramatic and their importance cannot be overemphasized. The action of an adjuvant allows much smaller doses of antigen to be used and generates antibody responses that are more persistent. The nonspecific activation of the immune response often can spell the difference between success and failure in obtaining an immune response. Adjuvants should be used for first injections unless there is some very specific reason to avoid this. Most adjuvants incorporate two components. One component is designed to protect the antigen from rapid catabolism (e.g., liposomes or synthetic surfactants (Hunter et al. 1981)). Liposomes are only effective when the immunogen is incorporated into the outer lipid layer; entrapped molecules are not seen by the immune system. The other component is a substance that will stimulate the immune response nonspecifically. These substances act by raising the level of lymphokines. Lymphokines stimulate the activity of antigen-processing cells directly and cause a local inflammatory reaction at the site of injection. Early work relied entirely on heat-killed bacteria (Dienes 1936) or lipopolysaccharide (LPS) (Johnson et al. 1956). LPS is reasonably toxic, and, through analysis of its structural components, most of its properties as an adjuvant have been shown to be in a portion known as lipid A. Lipid A is available in a number of synthetic and natural forms that are much less toxic than LPS, but still retains most of the better adjuvant properties of parental LPS molecule. Lipid A compounds are often delivered using liposomes.

Recently an intense drive to find potent adjuvants with more acceptable side effects has led to the production of new synthetic adjuvants. The present invention provides the sequence 1826 TCCATGACGTTCCTGACGTT (SEQ ID NO: 10), which is an adjuvant including CpG containing nucleic acids. The sequence is a strong immune activating sequence and is a superb adjuvant, with efficacy comparable or superior to complete Freund's, but without apparent toxicity.

Titration of Induction of Murine IL-6 Secretion by CpG Motifs

Figure 1A:
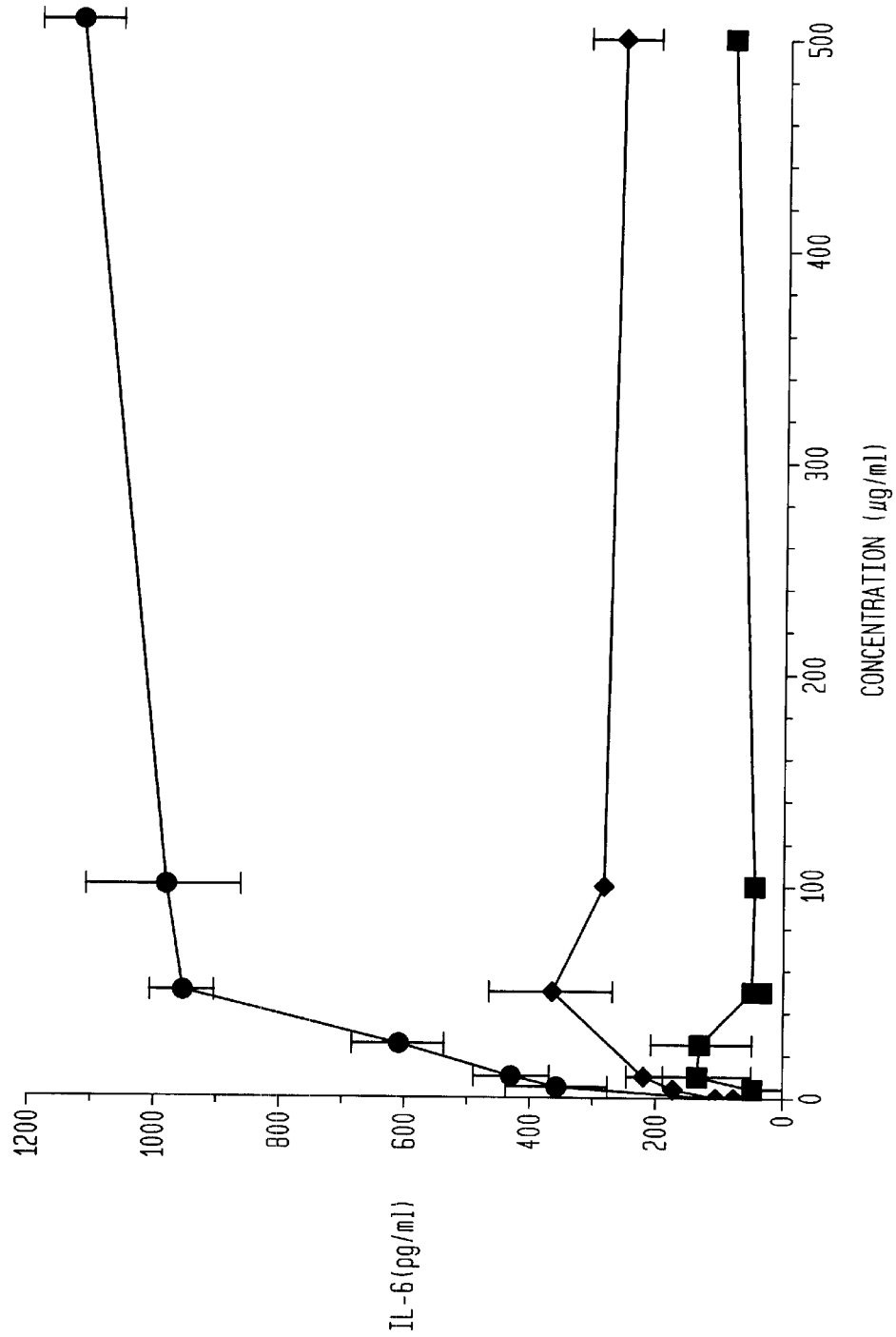
FIGS. 1A–C are graphs plotting dose-dependent IL-6 production in response to various DNA sequences in T cell depleted spleen cell cultures.
Figure 1B:
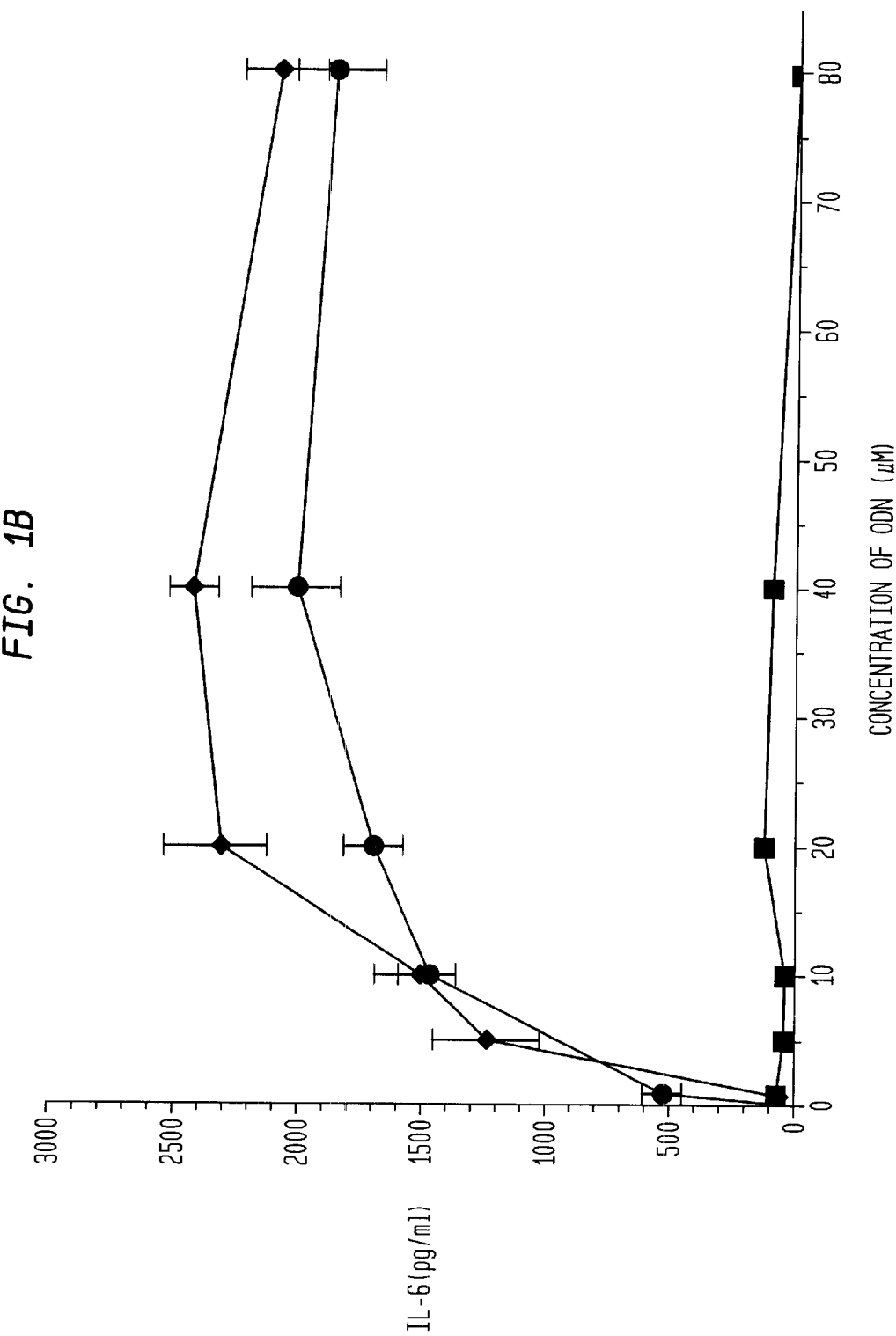
Figure 1C:
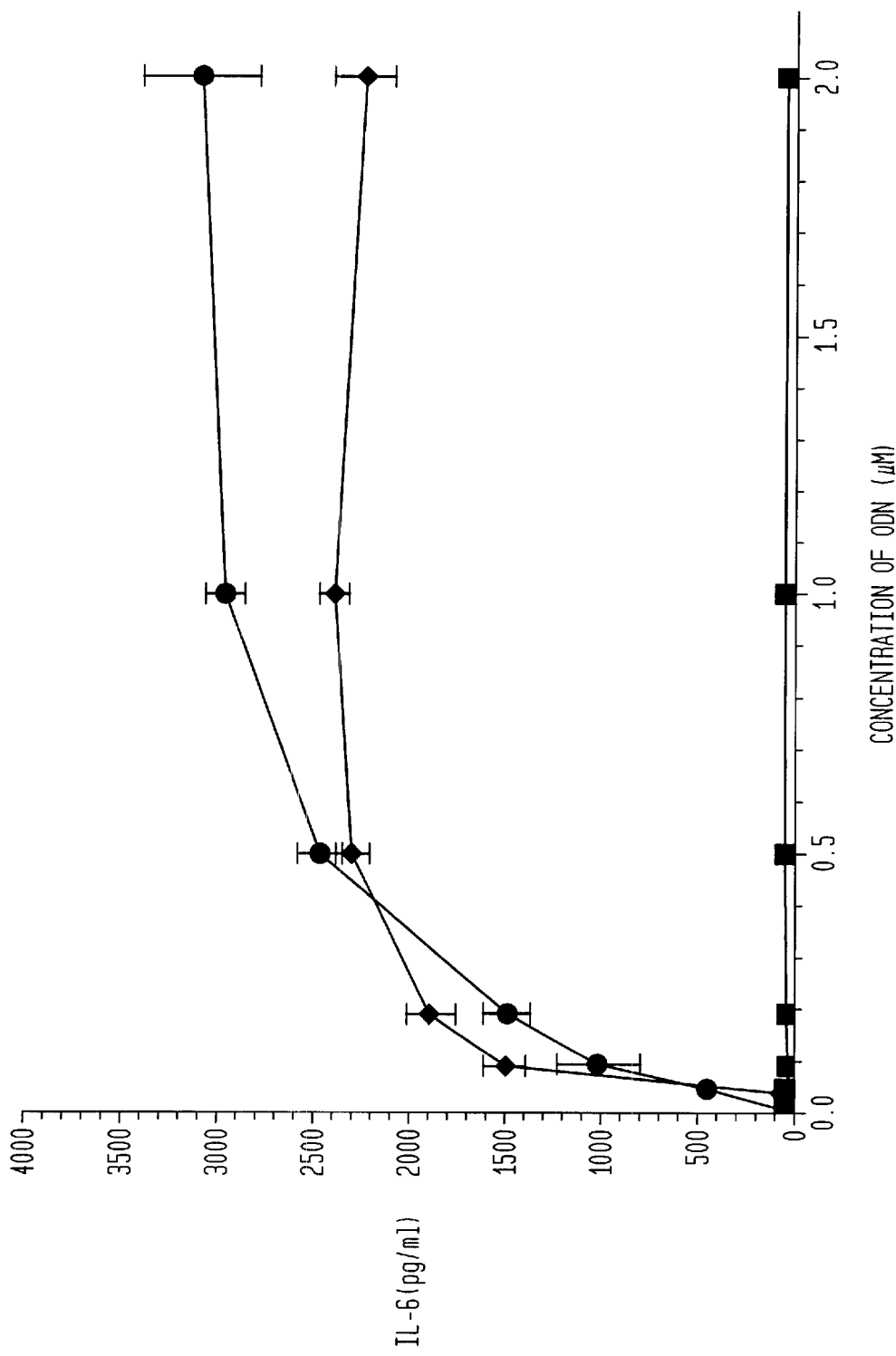

Bacterial DNA and CpG ODN induced IL-6 production in T cell depleted murine spleen cells in a dose-dependent manner, but vertebrate DNA and non-CpG ODN did not (FIG. 1). IL-6 production plateaued at approximately 50 μg/ml of bacterial DNA or 40 μM of CpG O—ODN. The maximum levels of IL-6 induced by bacterial DNA and CpG ODN were 1–1.5 ng/ml and 2–4 ng/ml respectively. These levels were significantly greater than those seen-after stimulation by LPS (0.35 ng/ml) (FIG. 1A). To evaluate whether CpG ODN with a nuclease-resistant DNA backbone would also induce IL-6 production, S—ODN were added to T cell depleted murine spleen cells. CpG S—ODN also induced IL-6 production in a dose-dependent manner to approximately the same level as CpG O—ODN while non-CpG S—ODN failed to induce IL-6 (FIG. 1C). CpG S—ODN at a concentration of 0.05 μM could induce maximal IL-6 production in these cells. This result indicted that the nuclease-resistant DNA backbone modification retains the sequence specific ability of CpG DNA to induce IL-6 secretion and that CpG S—ODN are more than 80-fold more potent than CpG O—ODN in this assay system.

Induction of Murine IL-6 Murine by CpG DNA in vivo

To evaluate the ability of bacterial DNA and CpG S—ODN to induce Il-6 secretion in vivo, BALB/c mice were injected iv. with 100 μg of *E. coli* DNA, calf thymus DNA, or CpG or non-stimulatory S—ODN and bled 2 hr after stimulation. The level of IL-6 in the sera from the *E. coli* DNA injected group as approximately 13 ng/ml while IL-6 was not detected in the sera from calf thymus DNA or PBS injected groups (Table 4). CpG S—ODN also induced IL-6 secretion in vivo. The IL-6 level in the sera from CpG S—ODN injected groups was approximately 20 ng/ml. In contrast, IL-6 was not detected in the sera from non-stimulatory S—ODN stimulated group (Table 4).

TABLE 4

Secretion of Murine IL-6 induced by CpG DNA stimulation in vivo.

| Stimulant | IL-6 (pg/ml) |
|---|---|
| PBS | <50 |
| E. coliDNA | 13858 ± 3143 |
| Calf Thymus DNA | <50 |
| CpG S-ODN | 20715 ± 606 |
| non-CpG S-ODN | <50 |

Mice (2 mice/group) were i.v. injected with 100 μl of PBS, 200 μl of *E. coli* DNA or calf thymus DNA, or 500 μg of CpG S-ODN or non-CpG control S-ODN. Mice were bled 2 hr after injection and 1:10 dilution of each serum was analyzed by IL-6 ELISA. Sensitivity limit of IL-6 ELISA was 5 pg/ml. Sequences of the CpG S-ODN is 5'GCATGACGTTGAGCT3'(SEQ. ID. No:6) and of the non-stimulatory S-ODN is 5'GCTAGATGTTAGCGT3'(SEQ. ID. No:4). Note that although there is a CpG in sequence 48, it is too close to the 3' end to effect stimulation, as explained herein. Data represent mean ± SD of duplicates. The experiment was done at least twice with similar results.

Kinetics of Murine IL-6 Secretion After Stimulation by CpG Motifs in vivo

Figure 2:
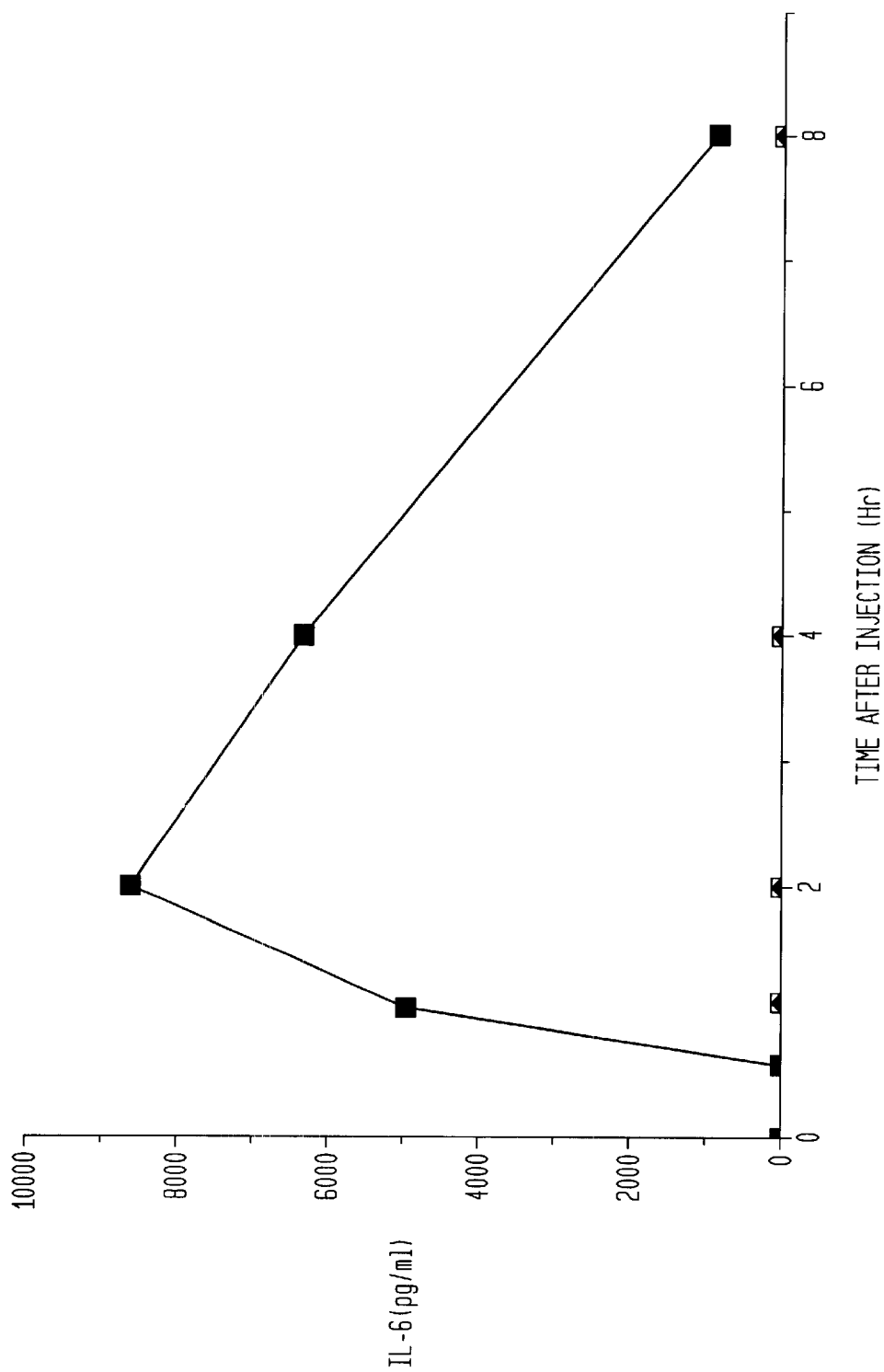
FIG. 2 is a graph plotting IL-6 production induced by CpG DNA in vivo as determined 1–8 hrs after injection. Data represent the mean for duplicate analyses of sera from two mice. BALB/c mice (two mice/group) were inject iv. with 100 μl of PBS (□) of 200 μg of CpG phosphorothioate ODN 5' TCCATGACGTTCCTGATGCT 3' (SEQ ID NO:7) (■) or non-CpG phosphorothioate 5' TCCATGAGCTTCCTGAGTCT 3' (SEQ ID NO: 8) (♦).

To evaluate the kinetics of induction of IL-6 secretion by CpG DNA n vivo, BALB/c mice were injected iv. with CpG or control non-CpG S—ODN. Serum IL-6 levels were significantly increased within 1 hr and peaked at 2 hr to a level of approximately 9 ng/ml in the CpG S—ODN injected group (FIG. 2). Il-6 protein in sera rapidly decreased after 4 hr and returned to basal level by 12 hr after stimulation. In contrast to CpG DNA stimulated groups, no significant increase of IL-6 was observed in the sera from the non-stimulatory S—ODN or PBS injected groups (FIG. 2).

Tissue Distribution and Kinetics of IL-6, mRNA Expression Induced by CpG Motifs in vivo As shown in FIG. 2, the level of serum IL-6 increased rapidly after CpG DNA stimulation. To investigate the possible tissue origin of this serum IL-6, and the kinetics of IL-6 gene expression in vivo after CpG DNA stimulation, BALB/c mice were injected iv with CpG or non-CpG S—ODN and RNA was extracted from liver, spleen, thymus, and bone marrow at various time points after stimulation. As shown in FIG. 3A, the level of IL-6 mRNA in liver, spleen, and thymus was increased within 30 min. after injection of CpG S—ODN. The liver IL-6 mRNA peaked at 2 hr post-injection and rapidly decreased and reached basal level 8 hr after stimulation (FIG. 3A). Splenic IL-6 mRNA peaked at 2 hr after stimulation and then gradually decreased (FIG. 3A). Thymus IL-6 mRNA peaked at 1 hr post-injection and then gradually decreased (FIG. 3A). IL-6 mRNA was significantly increased in bone marrow within 1 hr after CpG S—ODN injection but then returned to basal level. In response to CpG S—ODN, liver, spleen and thymus showed more substantial increases in IL-6 mRNA expression than the bone marrow.

Patterns of Murine Cytokine Expression Induced by CpG DNA

In vivo or in whole spleen cells, no significant increase in the protein levels of the following interleukins: IL-2, IL-3, IL-4, IL-5, or IL-10 was detected within the first six hours (Klinnan, D. M. et al., (1996) *Proc. Natl. Acad. Sci. USA* 93:2879–2883). However, the level of TNF-α is increased within 30 minutes and the level of IL-6 increased strikingly within 2 hours in the serum of mice injected with CpG ODN. Increased expression of IL-12 and interferon gamma (IFN-γ) mRNA by spleen cells was also detected within the first two hours.

TABLE 5

| ODN | Sequence(5"-3") | IL-6$_1$ | TNF-α$_1$ | IFN-γ$_1$ | GM-CSF | IL-11 |
|---|---|---|---|---|---|---|
| 512 SEQ ID NO:28 | TCCATGTCGGT CCTGATGCT | 500 | 140 | 15.6 | 70 | 250 |
| 1637 SEQ ID NO:33 | ... C_. ... | 550 | 16 | 7.8 | 15.6 | 16 |
| 1615 SEQ ID NO:34 | ... G_. ... | 600 | 145 | 7.8 | 45 | 145 |
| 1614 SEQ ID NO:35 | ... A_. ... | 550 | 31 | 0 | 50 | 31 |
| 1636 SEQ ID NO:36 | ... _A ... | 325 | 400 | 35 | 40 | 250 |
| 1634 SEQ ID NO:37 | ... _C ... | 300 | 400 | 40 | 85 | 400 |
| 1619 SEQ ID NO:38 | ... _T ... | 275 | 450 | 200 | 80 | 450 |
| 1618 SEQ ID NO:7 | ... A_T ... | 300 | 60 | 15.6 | 15.6 | 62 |
| 1639 SEQ ID NO:3 | ... AA_T ... | 625 | 220 | 15.6 | 40 | 220 |
| 1707 SEQ ID NO:39 | ... A_TC ... | 300 | 70 | 17 | 0 | 70 |
| 1708 SEQ ID NO:40 | ... CA_TG ... | 270 | 10 | 17 | ND | 10 | dots indicate identity; CpG dinucleotides are underlined
[1]measured by ELISA using Quantikine kits from R&D Systems (pg/ml)
Cells were cultured in 10% autologous serum with the indicated oligodeoxynucleotides (12 μg/ml) for 4 hr in the case of TNF-α or 24 hr for the other cytokines before supernatant harvest and assay. Data are presented as the level of cytokine above that in wells with no added oligodeoxynucleotide.

CpG DNA Induces Cytokine Secretion by Human PBMC, Specifically Monocytes

The same panels of ODN used for studying mouse cytokine expression were used to determine whether human cells also are induced by CpG motifs to express cytokine (or proliferate), and to identify the CpG motif(s) responsible. Oligonucleotide 1619 (GTCGTT; SEQ. ID. NO: 57) was the best inducer of TNF-α and IFN-γ secretion, and was closely followed by a nearly identical motif in oligonucleotide 1634 (GTCGCT; SEQ. ID. NO: 58) (Table 5). The motifs in oligodeoxynucleotides 1637 and 1614 (GCCGGT; SEQ. ID. NO: 109) and (GACGGT; SEQ. ID. NO: 110) led to strong IL-6 secretion with relatively little induction of other cytokines. Thus, it appears that human lymphocytes, like murine lymphocytes, secrete cytokines differentially in response to CpG dinucleotides, depending on the surrounding bases. Moreover, the motifs that stimulate murine cells best differ from those that are most effective with human cells. Certain CpG oligodeoxynucleotides are poor at activating human cells (oligodeoxynucleotides 1707, 1708, which contain the palindrome forming sequences GACGTC (SEQ. ID. NO: 111) and CACGTG (SEQ. ID. NO: 112) respectively).

The cells responding to the DNA appear to be monocytes, since the cytokine secretion is abolished by treatment of the cells with L-leucyl-L-leucine methyl ester (L-LME), which is selectively toxic to monocytes (but also to cytotoxic T lymphocytes and NK cells), and does not affect B cell Ig secretion (Table 6). The cells surviving L-LME treatment had >95% viability by trypan blue exclusion, indicating that the lack of a cytokine response among these cells did not simply reflect a nonspecific death of all cell types. Cytokine secretion in response to *E. coli* (EC) DNA requires unmethylated CpG motifs, since it is abolished by methylation of the EC DNA (next to the bottom row, Table 6). LPS contamination of the DNA cannot explain the results since the level of contamination was identical in the native and methylated DNA, and since addition of twice the highest amount of contaminating LPS had no effect (not shown).

TABLE 6

CpG DNA induces cytokine secretion by human PBMC

| DNA | TNF-α(pg/ml)[1] | IL-6 (pg/ml) | IFN-γ (pg/ml) | RANTES (pg/ml) |
|---|---|---|---|---|
| EC DNA (50 μg/ml) | 900 | 12,000 | 700 | 1560 |
| EC DNA (5 μg/ml) | 850 | 11,000 | 400 | 750 |
| EC DNA (0.5 μg/ml) | 500 | ND | 200 | 0 |
| EC DNA (0.05 μg/ml) | 62.5 | 10,000 | 15.6 | 0 |
| EC DNA (50 μg/ml) + L-LME$_2$ | 0 | ND | ND | ND |
| EC DNA (10 μg/ml) Methyl.[3] | 0 | 5 | ND | ND |
| CT DNA (50 μg/ml) | 0 | 600 | 0 | 0 |

[1]Levels of all cytokines were determined by ELISA using Quantikine kits from R&D Systems as described in the previous table. Results are representative using PBMC from different donors.
[2]Cells were pretreated for 15 min. with L-leucyl-L-leucine methyl ester (M-LME) to determine whether the cytokine production under these conditions was from monocytes (or other L-LME-sensitive cells).
[3]EC DNA was methylated using 2U/μg DNA of CpG methylase (New England Biolabs) according to the manufacturer's directions, and methylation confirmed by digestion with Hpa-II and Msp-I. As a negative control, samples were included containing twice the maximal amount of LPS contained in the highest concentration of EC DNA which failed to induce detectable cytokine production under these experimental conditions. ND = not done The loss of cytokine production in the PBMC treated with L-LME suggested that monocytes may be responsible for cytokine production in response to CpG DNA. To test this hypothesis more directly, the effects of CpG DNA on highly purified human monocytes and macrophages was tested. As hypothesized, CpG DNA directly activated production of the cytokines IL-6, GM-CSF, and TNF-α by human macrophages, whereas non-CpG DNA did not (Table 7).

TABLE 7

CpG DNA induces cytokine expression in purified human macrophages

| | IL-6 (pg/ml) | GM-CSF (pg/ml) | TNF-α(pg/ml) |
|---|---|---|---|
| Cells alone | 0 | 0 | 0 |
| CT DNA (50 μg/ml) | 0 | 0 | 0 |
| EC DNA (50 μg/ml) | 2000 | 15.6 | 1000 |

Figure 4A:
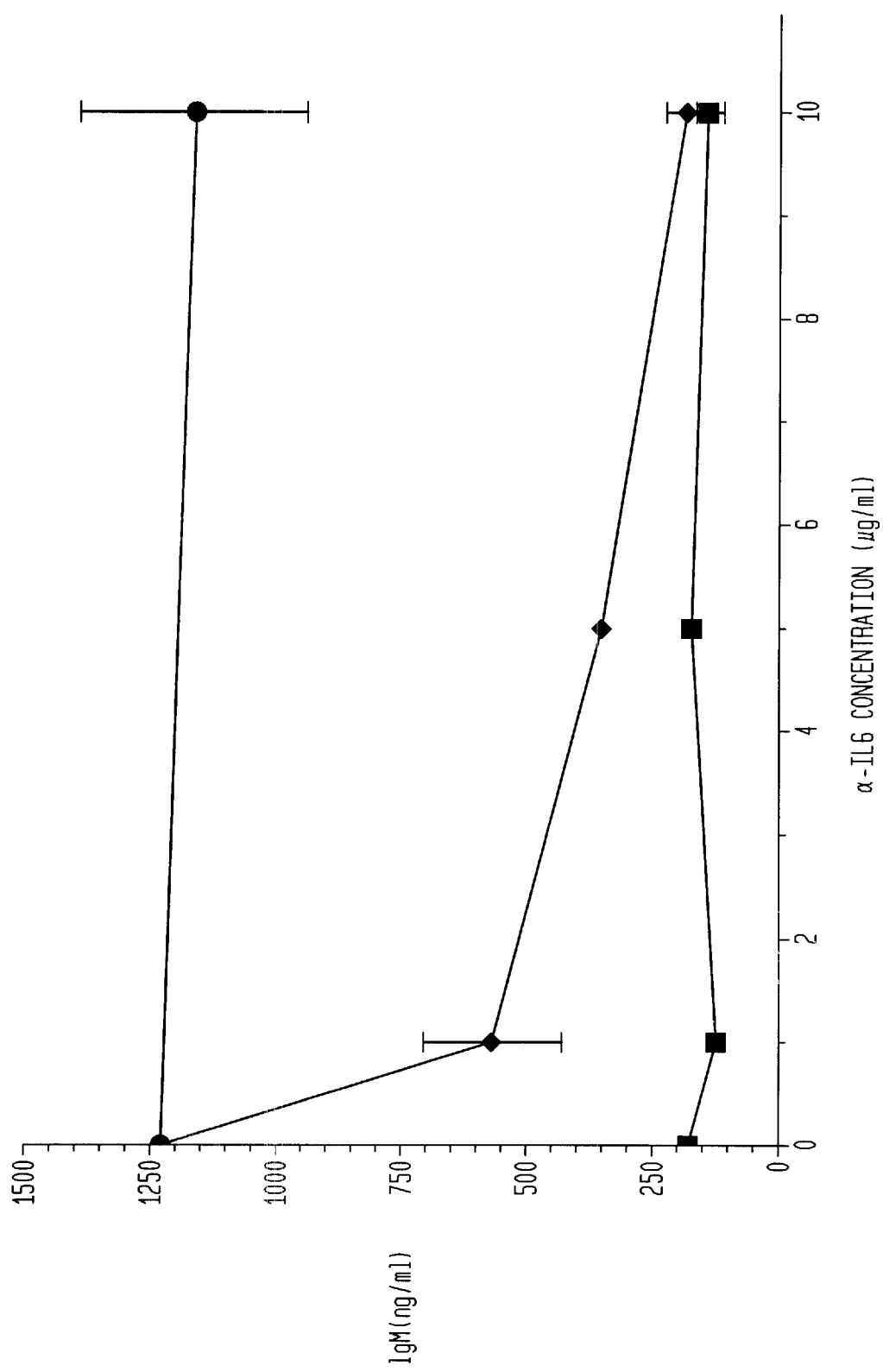
FIG. 4A is a graph plotting dose-dependent inhibition of CpG-induced IgM production by anti-IL-6. Splenic B-cells from DBA/2 mice were stimulated with CpG ODN 5' TCCAAGACGTTCCTGATGCT 3' (SEQ ID NO:9) in the presence of the indicated concentrations of neutralizing anti-IL-6 (♦) or isotype control Ab (●) and IgM levels in culture supernatants determined by ELISA. In the absence of CpG ODN, the anti-IL-6 Ab had no effect on IgM secretion (■).
Figure 4B:
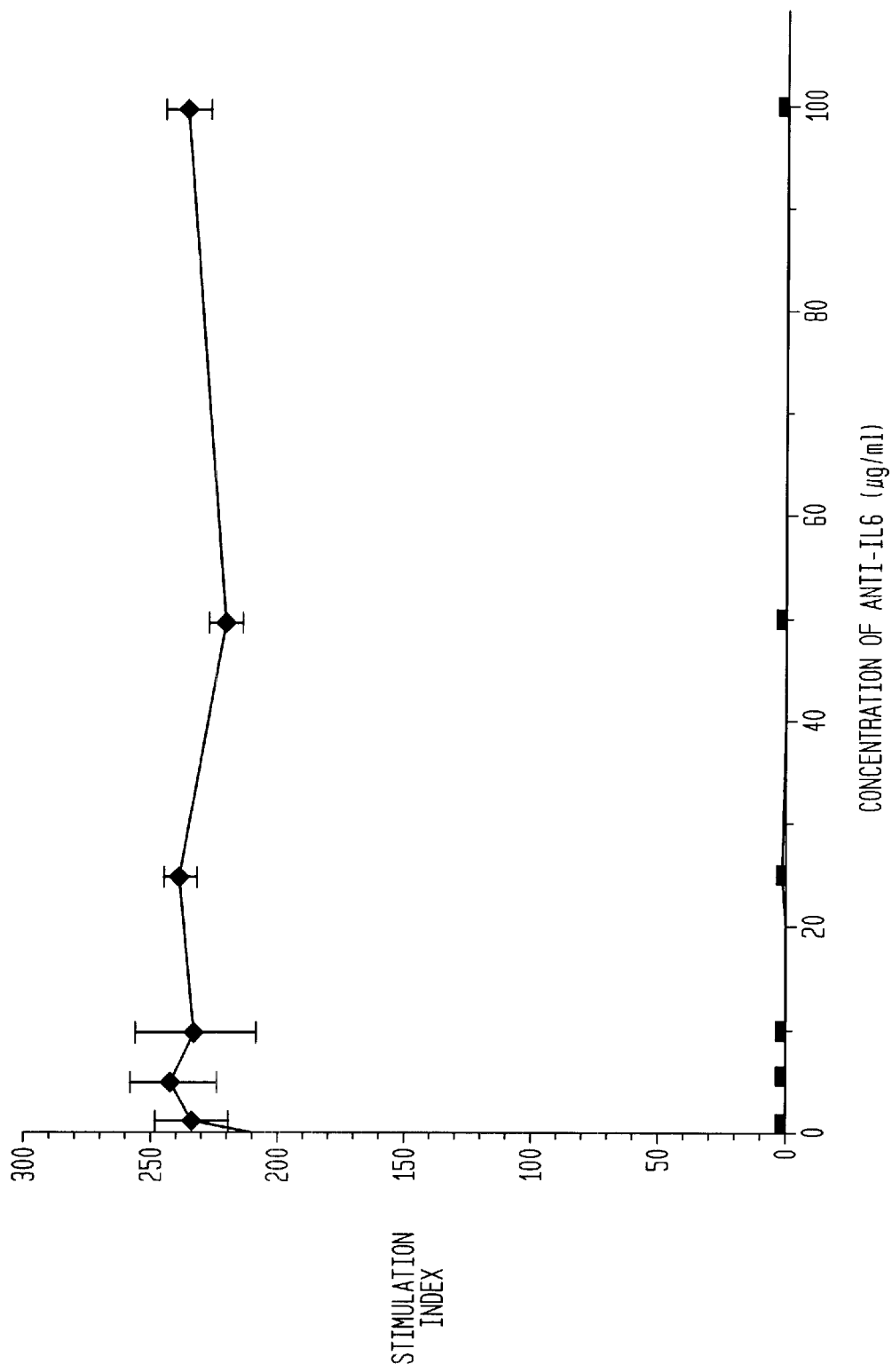
FIG. 4B is a graph plotting the stimulation index of CpG-induced splenic B cells cultured with anti-IL-6 and CpG S—ODN 5' TCCATGACGTTCCTGATGCT 3' (SEQ ID NO:7) (♦) or anti-IL-6 antibody only (■). Data present the mean±standard deviation of triplicates.

Biological Role of IL-6 in Inducing Murine IgM Production in Response to CpG Motifs The kinetic studies described above revealed that induction of IL-6 secretion, which occurs within 1 hr post CpG stimulation, precedes IgM secretion. Since the optimal CpG motif for ODN inducing secretion of IL-6 is the same as that for IgM (Table 2), whether the CpG motifs independently induce IgM and IL-6 production or whether the IgM production is dependent on prior IL-6 secretion was examined. The addition of neutralizing anti-IL-6 antibodies inhibited in vitro IgM production mediated by CpG ODN in a dose-dependent manner but a control antibody did not (FIG. 4A). In contrast, anti-IL-6 addition did not affect either the basal level or the CpG-induced B cell proliferation (FIG. 4B).

Figure 5:
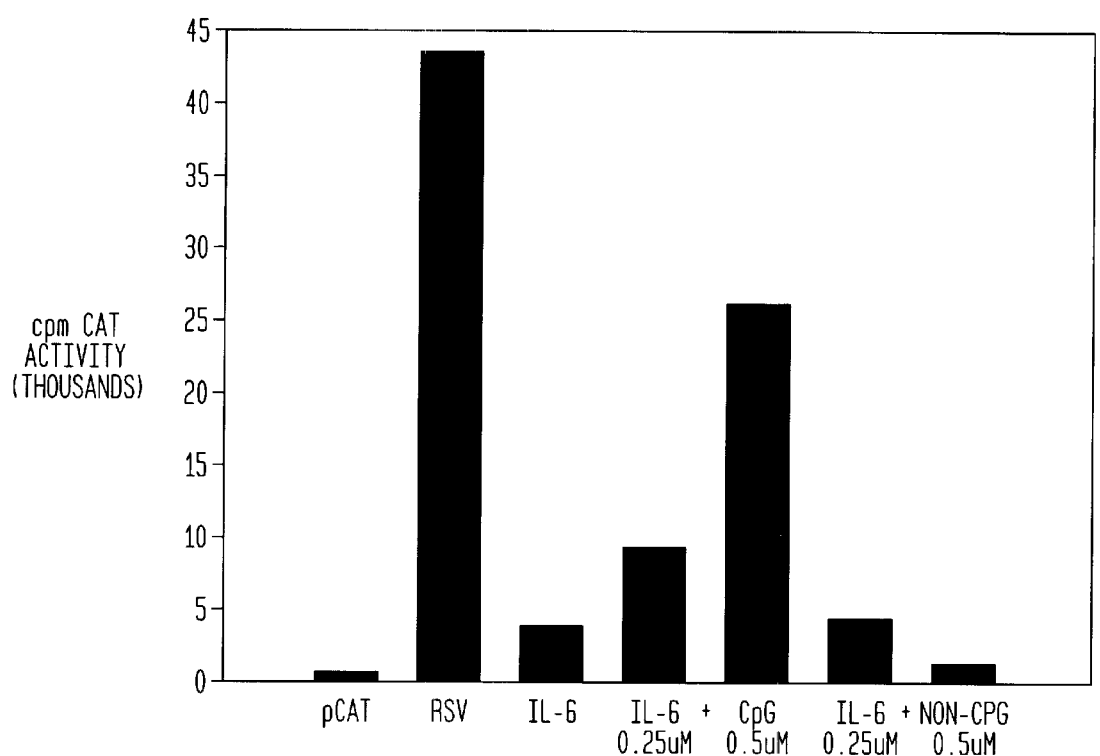
FIG. 5 is a bar graph plotting chloramphenicol acetyltransferase (CAT) activity in WEH1-231 cells transfected with a promoter-less CAT construct (pCAT), positive control plasmid (RSV), or IL-6 promoter-CAT construct alone or cultured with CpG 5' TCCATGACGTTCCTGATGCT 3' (SEQ ID NO: 7) or non-CpG 5' TCCATGAGCTTCCTGAGTCT 3' (SEQ ID NO: 8) phosphorothioate ODN at the indicated concentrations. Data present the mean of triplicates.

Increased Transcriptional Activity of the IL-6 Promoter in Response to CpG DNA The increased level of IL-6 mRNA and protein after CpG DNA stimulation could result from transcriptional or post-transcriptional regulation. To determine if the transcriptional activity of the IL-6 promoter was unregulated in B cells cultured with CpG ODN, a murine B cell line, WEHI-231, which produces IL-6 in response to CpG DNA, was transfected with an IL-6 promoter-CAT construct (pIL-6/CAT) (Pottrats, S. T. et al, 17B-estradiol) inhibits expression of human interleukin-6-promoter-reporter constructs by a receptor-dependent mechanism. *J. Clin. Invest.* 93:944). CAT assays were performed after stimulation with various concentrations of CpG or non-CpG ODN. As shown in FIG. 5, CpG ODN induced increased CAT activity in dose-dependent manner while non-CPG ODN failed to induce CAT activity. This confirms that CpG induces the transcriptional activity of the IL-6 promoter.

Dependence of B Cell Activation by CpG ODN on the Number of 5' and 3' Phosphorothioate Internucleotide Linkages To determine whether partial sulfur modification of the ODN backbone would be sufficient to enhance B cell activation, the effects of a series of ODN with the same sequence, but with differing numbers of S internucleotide linkages at the 5' end of ODN were required to provide optimal protection of the ODN from degradation by intracellular exo- and endo-nucleases. Only chimeric ODN containing two 5' phosphorothioate-modified linkages, and a variable number of 3' modified linkages were therefore examined.

The lymphocyte stimulating effects of these ODN were tested at three concentrations (3.3, 10, and 30 $\mu$M) by measuring the total levels of RNA synthesis (by $^3$H uridine incorporation) or DNA synthesis (by $^3$H thymidine incorporation) in treated spleen cell cultures (Example 10). O—ODN (0/0 phosphorothioate modifications) bearing a CpG motif caused no spleen cell stimulation unless added to the cultures at concentrations of at least 10 $\mu$M (Example 10). However, when this sequence was modified with two S linkages at the 5' end and at least three S linkages at the 3' end, significant stimulation was seen at a dose of 3.3 $\mu$M. At this low dose, the level of stimulation showed a progressive increase as the number of 3' modified bases was increased, until this reached or exceeded six, at which point the stimulation index began to decline. In general, the optimal number of 3' S linkages for spleen cell stimulation was five. Of all three concentrations tested in these experiments, the S—ODN was less stimulatory than the optimal chimeric compounds.

Dependent of GpG-mediated Lymphocyte Activation on the Type of Backbone Modification Phosphorothioate modified ODN (S—ODN) are far more nuclease resistant than phosphodiester modified ODN (O—ODN). Thus, the increased immune stimulation caused by S—ODN and S—O—ODN (i.e., chimeric phosphorothioate ODN in which the central linkages are phosphodiester, but the two 5' and five 3' linkages are phosphorothioate modified) compared to O—ODN may result from the nuclease resistance of the former. To determine the role of ODN nuclease resistance in immune stimulation by CpG ODN, the stimulatory effects of chimeric ODN in which the 5' and 3' ends were rendered nuclease resistant with either methylphosphonate (MP-), methylphosphorothioate (MPS-), phosphorothioate (S-), or phosphorodithioate (S$_2$-) internucleotide linkages were tested (Example 10). These studies showed that despite their nuclease resistance, MP—O—ODN were actually less immune stimulatory than O—ODN. However, combining the MP and S modifications by replacing both nonbridging O molecules with 5', and 3' MPS internucleotide linkages restored immune stimulation to a slightly higher level than that triggered by O—ODN.

S—O—ODN were far more stimulatory than O—ODN, and were even more stimulatory than S—ODN, at least at concentrations above 3.3 $\mu$M. At concentrations below 3 $\mu$M, the S—ODN with the 3M sequence was more potent than the corresponding S—O—ODN, while the S—ODN with the 3D sequence was less potent than the corresponding S—O—ODN (Example 10). In comparing the stimulatory CpG motifs of these two sequences, it was noted that the 3D sequence is a perfect match for the stimulatory motif in that the CpG is flanked by two 5' purines and two 3' pyrimidines. However, the bases immediately flanking the CpG in ODN 3D are not optimal; it has a 5' pyrimidine and a 3' purine. Based on further testing, it was found that the sequence requirement for immune stimulation is more stringent for S—ODN than for S—O— or O—ODN. S—ODN with poor matches to the optimal CpG motif cause little or no lymphocyte activation (e.g., Sequence 3D). However, S—ODN with good matches to the motif, most critically at the positions immediately flanking the CpG, are more potent than the corresponding S—O—ODN (e.g., Sequence 3M, Sequences 4 and 6), even though at higher concentrations (greater than 3 $\mu$M) the peak effect from the S—O—ODN is greater (Example 10).

S$_2$—O—ODN were remarkably stimulatory, and caused substantially greater lymphocyte activation than the corresponding S—ODN or S—O—ODN at every tested concentration.

The increased B cell stimulation seen with CpG ODN bearing S or S$_2$ substitutions could result from any or all of the following effects: nuclease resistance, increased cellular uptake, increased protein binding, and altered intracellular localization. However, nuclease resistance cannot be the only explanation, since the MP—O—ODN were actually less stimulatory than the O—ODN with CpG motifs. Prior studies have shown that ODN uptake by lymphocytes is markedly affected by the backbone chemistry (Zhao, et al. (1993) Comparison of cellular binding and uptake of antisense phosphodiester, phosphorothioate, and mixed phosphorothioate and methylphosphonate oligonucleotides. (Antisense Research and Development 3, 53–66; Zhao et al., (1994) Stage specific oligonucleotide uptake in murine bone marrow B cell precursors. Blood 84, 3660–3666). The highest cell membrane binding and uptake was seen with S—ODN, followed by S—O—ODN, O—ODN, and MP—ODN. This differential uptake correlates with the degree of immune stimulation.

Unmethylated CpG Containing Oligos Have NK Cell Stimulatory Activity

Experiments were conducted to determine whether CpG containing oligonucleotides stimulated the activity of natural killer (NK) cells in addition to B cells. As shown in Table 8, a marked induction of NK activity among spleen cells cultured with CpG ODN 1 and 3Dd was observed. In contrast, there was relatively on induction in effectors that had been treated with non-CpG control ODN.

TABLE 8

Induction Of NK Activity By CpG Oligodeoxynucleotides (ODN)

| ODN | % YAC-1 Specific Lysis* | | % 2C11 Specific Lysis | |
|---|---|---|---|---|
| | Effector: 50:1 | Target 100:1 | Effector: 50:1 | Target 100:1 |
| None | −1.1 | −1.4 | 15.3 | 16.6 |
| 1 | 16.1 | 24.5 | 38.7 | 47.2 |
| 3Dd | 17.1 | 27.0 | 37.0 | 40.0 |
| non-CpG ODN | −1.6 | −1.7 | 14.8 | 15.4 |

Induction of NK Activity by DNA Containing CpG Motifs, but Not by Non-CpG DNA

Bacterial DNA cultured for 18 hrs at 37° C. and then assayed for killing of K562 (human) or Yac-1 (mouse) target cells induced NK lytic activity in both mouse spleen cells depleted of B cells and human PBMC, but vertebrate DNA may be a consequence of its increased level of unmethylated CpG dinucleotides, the activating properties of more than 50 synthetic ODN containing unmethylated, methylated, or no CpG dinucleotides was tested. The results, summarized in Table 9, demonstrate that synthetic ODN can stimulate significant NK activity, as long as they contain at least one unmethylated CpG dinucleotide. No difference was observed in the stimulatory effects of ODN in which the CpG was within a palindrome (such as ODN 1585, which contains the palindrome AACGTT; SEQ. ID. NO: 105) from those ODN without palindromes (such as 1613 ro 1619), with the caveat that optimal stimulation was generally seem with ODN in which the CpG was flanked by two 5' purines or a 5' GpT dinucleotide and two 3' pyrimidines. Kinetic experiments demonstrated that NK activity peaked around 18 hrs. after addition of the ODN. The data indicates that the murine NK response is dependent on the prior activation of monocytes by CpG DNA, leading to the production of IL-12, TNF-α, and IFN-α/b (Example 11).

Figure 6:
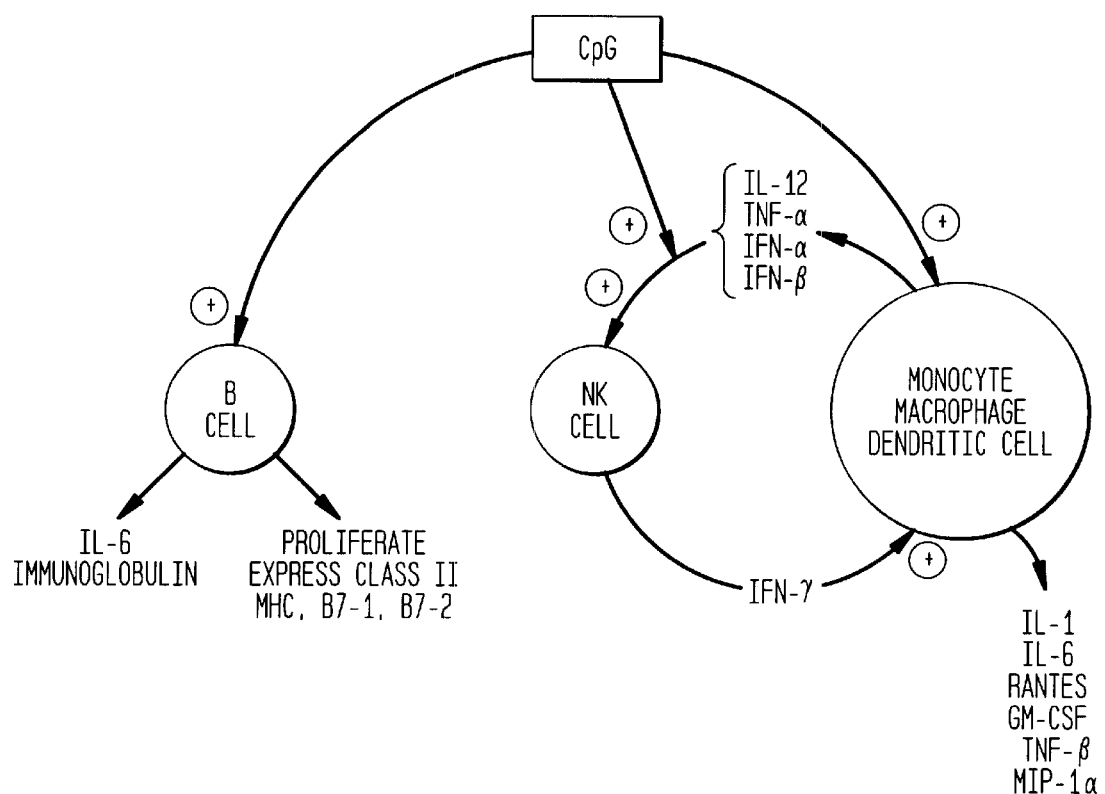
FIG. 6 is a schematic overview of the immune effects of the immunostimulatory unmethylated CpG containing nucleic acids, which can directly activate both B cells and monocytic cells (including macrophages and dendritic cells) as shown. The immunostimulatory oligonucleotides do not directly activate purified NK cells, but render them competent to respond to IL-12 with a marked increase in their IFN-γ secretion by NK cells, the immunostimulatory nucleic acids promote a Th1 type immune response. No direct activation of proliferation of cytokine secretion by highly purified T cells has been found. However, the induction of Th1 cytokine secretion by the immunostimulatory oligonucleotides promotes the development of a cytotoxic lymphocyte response.

From all of these studies, a more complete understanding of the immune effects of CpG DNA has been developed, which is summarized in FIG. 6.

Immune activation by CpG motifs may depend on bases flanking the CpG, and the number of spacing of the CpGs present within an ODN. Although a single CpG in an ideal base context can be a very strong and useful immune activator, superior effects can be seen with ODN containing several CpGs with the appropriate spacing and flanking bases. For activation of murine B cells, the optimal CpG motif is TGACGTT (SEQ. ID. NO: 108); residues 10–17 of Seq. ID. No 70.

The following studies where conducted to identify optimal ODN sequences for stimulation of human cells by examining the effects of changing the number, spacing, and flanking bases of CpG dinucleotides.

Identification of Phosphorothioate ODN with Optimal CpG Motifs for Activation of Human NK Cells To have clinical utility, ODN must be administered to a subject in a form that protects them against nuclease degradation. Methods to accomplish this with phosphodiester ODN are well known in the art and include encapsulation in lipids or delivery systems such as nanoparticles. This protection can also be achieved using chemical substitutions to the DNA such as modified DNA backbones including those in which the internucleotide linkages are nuclease resistant. Some modifications may confer additional desirable properties such as increasing cellular uptake. For example, the phosphodiester linkage can be modified via replacement of one of the nonbridging oxygen atoms with a sulfur, which constitutes phosphorothioate DNA. Phosphorothioate ODN have enhanced cellular uptake (Krieg et al., Antisense Res. Dev. 6:133, 1996.) and improved B cell stimulation if they also have a CpG motif. Since NK activation correlates strongly with in vivo adjuvant effects, the identification of phosphorothioate ODN that will activate human NK cells is very important.

The effects of different phosphorothioate ODNs—containing CpG dinucleotides in various base contexts—on human NK activation (Table 10) were examined. ODN 1840, which contained 2 copies of the TGTCGTT (SEQ. ID.

TABLE 9

Induction of NK Activity by DNA Containing CpG Motifs but not by Non-CpG DNA

| DNA or Cytokine Added | | | LU/$10^6$ | |
|---|---|---|---|---|
| | | | Mouse Cells | Human Cells |
| Expt. 1 | None | | 0.00 | 0.00 |
| | IL-2 | | 16.68 | 15.82 |
| | E. Coli. DNA | | 7.23 | 5.05 |
| | Calf thymus DNA | | 0.00 | 0.00 |
| Expt. 2 | None | | 0.00 | 3.28 |
| | 1585 ggGGTCAACGTTGAGggggg | (SEQ ID No.12) | 7.38 | 17.98 |
| | 1629 -------gtc------ | (SEQ ID No.41) | 0.00 | 4.4 |
| Expt. 3 | None | | 0.00 | |
| | 1613 GCTAGACGTTAGTGT | (SEQ ID No. 42) | 5.22 | |
| | 1769 -------Z------ | (SEQ ID No. 117) | 0.02 | ND |
| | 1619 TCCATGTCGTTCCTGATGCT | (SEQ ID No. 38) | 3.35 | |
| | 1765 --------Z---------- | (SEQ ID No. 44) | 0.11 | |

CpG dinucleotides in ODN sequences are indicated by underlying; Z indicates methylcytosine. Lower case letters indicate nuclease resistant phosphorothioate modified internucleotide linkages which, in titration experiments, were more than 20 times as potent as non-modified ODN, depending on the flanking bases. Poly G ends (g) were used in some ODN, because they significantly increase the level of ODN uptake.

NO: 102) residues 14–20 of SEQ. ID. NO: 47 motif, had significant NK lytic activity (Table 10). To further identify additional ODNs optimal for NK activation, approximately one hundred ODN containing different numbers and spacing of CpG motifs, were tested with ODN1982 serving as a control. The result are shown in Table 1.

Effective ODNs began with a TC or TG at the 5' end, however, this requirement was not mandatory. ODNs with internal CpG motifs (e.g., ODN 1840) are generally less potent stimulators than those in which a GTCGCT (SEQ. ID. NO: 58) motif immediately follows the 5' TC (e.g., ODN 1967 and 1968). ODN 1968, which has a second GTCGTT SEQ. ID. NO: 57) motif in its 3' half, was consistently more stimulatory than ODN 1967, which lacks this second motif. ODN 1967, however, was slightly more potent than ODN 1968 in experiments 1 and 3, but not in experiment 2. ODN 2005, which has a third GTCGTT (SEQ. ID NO: 57) motif, inducing slightly higher NK activity on average than 1968. However, ODN 2006, in which the spacing between the GTCGTT (SEQ. ID. NO: 57) motifs was increased by the addition of two Ts between each motif, was superior to ODN 2005 and to ODN 2007, in which only one of the motifs had the additional of the spacing two Ts. The minimal acceptable spacing between CpG motifs is one nucleotide as long as the ODN has two pyrimidines (preferably T) at the 3' end (e.g., ODN 2015). Surprisingly, joining two GTCGTT (SEQ. ID. NO: 57) motifs end to end with a 5' T also created a reasonably strong inducer of NK activity (e.g., ODN 2016). The choice of thymine (T) separating consecutive CpG dinucleotides is not absolute, since ODN 2002 induced appreciable NK activation despite the fact that adenine (A) separated its CpGs (i.e., CGACGTT; SEQ. ID. NO: 113). It should also be noted that ODNs containing no CpG (e.g., ODN 1982), runs of CpGs, or CpGs in bad sequence contents (e.g., ODN 2010) had no stimulatory effect on NK activation.

TABLE 10

| ODN cells alone | Sequence (5'–3') | LU 0.01 | |
|---|---|---|---|
| 1754 | ACCATGGACGATCTGTTTCCCCTC | 0.02 | SEQ ID NO:59 |
| 1758 | TCTCCCAGCGTGCGCCAT | 0.05 | SEQ ID NO:45 |
| 1761 | TACCGCGTGCGACCCTCT | 0.05 | SEQ ID NO:60 |
| 1776 | ACCATGGACGAACTGTTTCCCCTC | 0.03 | SEQ ID NO:61 |
| 1777 | ACCATGGACGAGCTGTTTCCCCTC | 0.05 | SEQ ID NO:62 |
| 1778 | ACCATGGACGACCTGTTTCCCCTC | 0.01 | SEQ ID NO:63 |
| 1779 | ACCATGGACGTACTGTTTCCCCTC | 0.02 | SEQ ID NO:64 |
| 1780 | ACCATGGACGGTCTGTTTCCCCTC | 0.29 | SEQ ID NO:65 |
| 1781 | ACCATGGACGTTCTGTTTCCCCTC | 0.38 | SEQ ID NO:66 |
| 1823 | GCATGACGTTGAGCT | 0.08 | SEQ ID NO:6 |
| 1824 | CACGTTGAGGGGCAT | 0.01 | SEQ ID NO:67 |
| 1825 | CTGCTGAGACTGGAG | 0.01 | SEQ ID NO:68 |
| 1828 | TCAGCGTGCGCC | 0.01 | SEQ ID NO:69 |
| 1829 | ATGACGTTCCTGACGTT | 0.42 | SEQ ID NO:70 |
| 1830[2] | RANDOM SEQUENCE | 0.25 | |
| 1834 | TCTCCCAGCGGGCGCAT | 0.00 | SEQ ID NO:71 |
| 1836 | TCTCCCAGCGCGCGCCAT | 0.46 | SEQ ID NO:72 |
| 1840 | TCCATGTCGTTCCTGTCGTT | 2.70 | SEQ ID NO:73 |
| 1841 | TCCATAGCGTTCCTAGCGTT | 1.45 | SEQ ID NO:74 |
| 1842 | TCGTCGCTGTCTCCGCTTCTT | 0.06 | SEQ ID NO:75 |
| 1851 | TCCTGACGTTCCTGACGTT | 2.32 | SEQ ID NO:76 |

[1]Lytic units (LU) were measured as described (8). Briefly, PBMC were collected from normal donors and spun over Ficoll, then cultured with or without the indicated ODN (which were added to cultures at 6 µg/ml) for 24 hr. Then their ability to lyse $^{51}$Cr-labeled K562 cells was determined. The results shown are typical of those obtained with several different normal human donors.
[2]This oligo mixture contained a random selection of all 4 bases at each position.

Table 11. Induction of NK LU by Phosphorothioate CpG ODN with Good Motifs

TABLE 11

Induction of NK LU by Phosphorothioate CpG ODN with Good Motifs

| ODN[1] cells alone | sequence (5'–3') | SEQ ID NO: | expt. 1 0.00 | expt. 2 1.26 | expt. 3 0.46 |
|---|---|---|---|---|---|
| 1840 | TCCATGT<u>CG</u>TTCCTGT<u>CG</u>TT | 73 | 2.33 | ND | ND |
| 1960 | TCCTGT<u>CG</u>TTCCTGT<u>CG</u>TT | 77 | ND | 0.48 | 8.99 |
| 1961 | TCCATGT<u>CG</u>TTTTTGT<u>CG</u>TT | 78 | 4.03 | 1.23 | 5.08 |
| 1962 | TCCTGT<u>CG</u>TTCCTTGT<u>CG</u>TT | 52 | ND | 1.60 | 5.74 |
| 1963 | TCCTTGT<u>CG</u>TTCCTGT<u>CG</u>TT | 121 | 3.42 | ND | ND |
| 1965 | TCCTGT<u>CG</u>TTTTTTGT<u>CG</u>TT | 53 | 0.46 | 0.42 | 3.48 |
| 1966 | T<u>CG</u>T<u>CG</u>CTGTCTCCGCTTCTT | 75 | 2.62 | ND | ND |
| 1967 | T<u>CG</u>T<u>CG</u>CTGTCTGCCCTTCTT | 54 | 5.82 | 1.64 | 8.32 |
| 1968 | T<u>CG</u>T<u>CG</u>CTGTTGTCGTTTCTT | 55 | 3.77 | 5.26 | 6.12 |
| 1979 | TCCATGTZGTTCCTGTZGTT | 122 | 1.32 | ND | ND |
| 1982 | TCCAGGACTTCTCTCAGGTT | 79 | 0.05 | ND | 0.98 |
| 1990 | TCCATG<u>CG</u>TG<u>CG</u>TG<u>CG</u>TTTT | 80 | 2.10 | ND | ND |
| 1991 | TCCATG<u>CG</u>TTG<u>CG</u>TTG<u>CG</u>TT | 81 | 0.89 | ND | ND |
| 2002 | TCCACGA<u>CG</u>TTTT<u>CGA</u>CGTT | 82 | 4.02 | 1.31 | 9.79 |

TABLE 11-continued

Induction of NK LU by Phosphorothioate CpG ODN with Good Motifs

| ODN[1] cells alone | sequence (5'-3') | SEQ ID NO: | expt. 1 0.00 | expt. 2 1.26 | expt. 3 0.46 |
|---|---|---|---|---|---|
| 2005 | TCGTCGTTGTCGTTGTCGTT | 47 | ND | 4.22 | 12.75 |
| 2006 | TCGTCGTTTTGTCGTTTTGTCGT | 123 | ND | 6.17 | 12.82 |
| 2007 | TCGTCGTTGTCGTTTTGTCGTT | 49 | ND | 2.68 | 9.66 |
| 2008 | GCGTGCGTTGTCGTTGTCGTT | 56 | ND | 1.37 | 8.15 |
| 2010 | GCGGCGGGCGGCGCGCGCCC | 83 | ND | 0.01 | 0.05 |
| 2012 | TGTCGTTTGTCGTTTGTCGTT | 48 | ND | 2.02 | 11.61 |
| 2013 | TGTCGTTGTCGTTGTCGTTGTCGTT | 84 | ND | 0.56 | 5.22 |
| 2014 | TGTCGTTGTCGTTGTCGTT | 50 | ND | 5.74 | 10.89 |
| 2015 | TCGTCGTCGTCGTT | 51 | ND | 4.53 | 10.13 |
| 2016 | TGTCGTTGTCGTT | 85 | ND | 6.54 | 8.06 |

[1]PBMC essentially as described herein. Results are representative of 6 separate experiments; each experiment represents a different donor.
[2]This is the methylated version of ODN 1840; Z = 5-methyl cytosine LU is lytic units; ND = not done; CpG dinucleotides are underlined for clarity.

Identification of Phosphorothioate ODN with Optimal CpG Motifs for Activation of Human B Cell Proliferation The ability of a CpG ODN to induce B cell proliferation is a good measure of its adjuvant potential. Indeed, ODN with strong adjuvant effects generally also induce B cell proliferation. To determine whether the optimal CpG ODN for inducing B cell proliferation are the same as those for inducing NK cell activity, similar panels of ODN (Table 12) were tested. The most consistent stimulation appeared with ODN 2006 (Table 12).

Identification of Phosphorothioate ODN that Induce Human IL-2 Secretion

The ability of a CpG ODN to induce IL-12 secretion is a good measure of its adjuvant potential, especially in terms of its ability to induce a Th1 immune response, which is highly dependent on IL-12. Therefore, the ability of a panel of phosphorothioate ODN to induce OIL-12 secretion from human PBMC in vitro (Table 13) was examined. These experiments showed that in some human PBMC, most CpG ODN could induce IL-12 secretion (e.g., expt. 1). However,

TABLE 12

Induction of human B cell proliferation by Phosphorothioate CpG ODN

| | | | Stimulation Index[1] | | | | | |
|---|---|---|---|---|---|---|---|---|
| ODN | sequence (5'-3') | SEQ ID NO: | expt. 1 | expt. 2 | expt. 3 | expt 4 | expt. 5 | expt. 6 |
| 1840 | TCCATGTCGTTCCTGTCGTT | 73 | 4 | ND | ND | ND | ND | 34 |
| 1841 | TCCATAGCGTTCCTAGCGTT | 74 | 3 | ND | ND | ND | ND | ND |
| 1960 | TCCTGTCGTTCCTGTCGTT | 77 | ND | 2.0 | 2.0 | 3.6 | ND | ND |
| 1961 | TCCATGTCGTTTTTGTCGTT | 78 | 2 | 39 | 1.9 | 3.7 | ND | 37 |
| 1962 | TCCTGTCGTTCCTTGTCGTT | 52 | ND | 3.3 | 1.9 | 3.9 | 5.4 | 35 |
| 1963 | TCCTTGTCGTTCCTGTCGTT | 121 | 3 | ND | ND | ND | ND | ND |
| 1965 | TCCTGTCGTTTTTTTGTCGTT | 53 | 4 | 3.7 | 2.4 | 4.7 | 6.0 | 43 |
| 1967 | TCGTCGCTGTCTGCCCTTCTT | 54 | ND | 4.4 | 2.0 | 4.5 | 5.0 | 36 |
| 1968 | TCGTCGCTGTTGTCGTTTCTT | 55 | ND | 4.0 | 2.0 | 4.9 | 87 | 38 |
| 1982 | TCCAGGACTTCTCTCAGGTT | 79 | 3 | 1.8 | 1.3 | 3.1 | 3.2 | 1.2 |
| 2002 | TCCACGACGTTTTCGACGTT | 86 | ND | 2.7 | 1.4 | 4.4 | ND | 14 |
| 2005 | TCGTCGTTGTCGTTGTCGTT | 47 | 5 | 3.2 | 1.2 | 3.0 | 7.9 | 37 |
| 2006 | TCGTCGTTTTGTCGTTTTGTCGT | 46 | 4 | 4.5 | 2.2 | 5.8 | 8.3 | 40 |
| 2007 | TCGTCGTTGTCGTTTTGTCGTT | 49 | 3 | 4.0 | 4.2 | 4.1 | ND | 22 |
| 2008 | GCGTGCGTTGTCGTTGTCGTT | 56 | ND | 3.0 | 2.4 | 1.6 | ND | 12 |
| 2010 | GCGGCGGGCGGCGCGCGCCC | 83 | ND | 1.6 | 1.9 | 3.2 | ND | ND |
| 2012 | TGTCGTTTGTCGTTTGTCGTT | 48 | 2 | 2.8 | 0 | 3.2 | ND | 33 |
| 2013 | TGTCGTTGTCGTTGTCGTTGTCGTT | 84 | 3 | 2.3 | 3.1 | 2.8 | ND | 7 |
| 2014 | TGTCGTTGTCGTTGTCGTT | 50 | 3 | 2.5 | 4.0 | 3.2 | 6.7 | 14 |
| 2015 | TCGTCGTCGTCGTT | 51 | 5 | 1.8 | 2.6 | 4.5 | 9.4 | 1 |
| 2016 | TGTCGTTGTCGTT | 85 | ND | 1.1 | 1.7 | 2.7 | 7.3 | 1 |

[1]Cells = human spleen cells stored at -70° C. after surgical harvest or PBMC collected from normal donors and spun over Ficoll. Cells were cultured in 96 well U-bottom microtiter plates with or without the indicated ODN (which were added to cultures at 6 μml). N = 12 experiments. Cells were cultured for 4–7 days, pulsed with 1 μCi of ³H thymidine for 18 hr. before harvest and scintillation counting. Stimulation index = the ratio of cpm in wells without ODN to that in wells that had been stimulated throughout the culture period with the indicated ODN (there were no further additions of ODN after the cultures were set up). ND = not done.

other donors responded to just a few CpG ODN (E.g., expt. 2). ODN 2006 was a consistent inducer of IL12 secretion from most subjects (Table 13).

mitogenicity, demonstrates that the difference in CpG status is the cause of B cell stimulation by bacterial DNA. This data supports the following conclusion: that unmethylated

TABLE 13

Induction of human IL-12 secretion by Phosphorothioate CpG ODN

| ODN[1] cells alone | sequence (5'-3') | SEQ ID NO: | IL-12 (pg/ml) expt. 1 0 | expt. 2 0 |
|---|---|---|---|---|
| 1962 | TCCTGTCGTTCCTTGTCGTT | 52 | 19 | 0 |
| 1965 | TCCTGTCGTTTTTTGTCGTT | 53 | 36 | 0 |
| 1967 | TCGTCGCTGTCTGCCCTTCTT | 119 | 41 | 0 |
| 1968 | TCGTCGCTGTTGTCGTTTCTT | 120 | 24 | 0 |
| 2005 | TCGTCGTTGTCGTTGTCGTT | 47 | 25 | 0 |
| 2006 | TCGTCGTTTTGTCGTTTTGTCGTT | 46 | 29 | 15 |
| 2014 | TGTCGTTGTCGTTGTCGTT | 50 | 28 | 0 |
| 2015 | TCGTCGTCGTCGTT | 51 | 14 | 0 |
| 2016 | TGTCGTTGTCGTT | 85 | 3 | 0 |

[1]PBMC were collected from normal donors and spun over Ficoll, then cultured at $10^6$ cells/we in 96 well microtiter plates with or without the indicated ODN which were added to cultures a μg/ml. Supernatants were collected at 24 hr and tested for IL-12 levels by ELISA as described methods. A standard curve was run in each experiment, which represents a different donor.

Identification of B Cell and Monocyte/NK Cell-specific Oligonucleotides

As shown in FIG. 6, CpG DNA can directly activate highly purified B cells and monocytic cells. There are many similarities in the mechanism through which CpG DNA activates these cell types. For example, both require NFκB activation as explained further below.

In further studies of different immune effects of CpG DNA, it was found that there is more than one type of CpG motif. Specifically, olio 1668, with the best mouse B cell motif, is a strong inducer of both B cell and natural killer (NK) cell activation, while olio 1758 is a weak B cell activator, but still induces excellent NK responses (Table 14).

CpG dinucleotides present within bacterial DNA are responsible for the stimulatory effects of bacterial DNA.

Teleologically, it appears likely that lymphocyte activation by the CpG motif represents an immune defense mechanism that can thereby distinguish bacterial from host DNA. Host DNA, which would commonly be present in many anatomic regions and areas of inflammation due to apoptosis (cell death), would generally induce little or mo lymphocyte activation due to CpG suppression and methylation. However, the presence of bacterial DNA containing unmethylated CpG motifs can cause lymphocyte activation precisely in infected anatomic regions, where it is beneficial. This novel activation pathway provides a rapid alternative to T cell dependent antigen specific B cell activation. Since the

TABLE 14

Different CpG motifs stimulate optimal murine B cell and NK activation

| ODN | Sequence |  | B cell activation | NK activation |
|---|---|---|---|---|
| 1668 | TCCATGACGTTCCTGATGCT | (SEQ.ID.NO 7) | 42,849 | 2.52 |
| 1758 | TCTCCCAGCGTGCGCCAT | (SEQ.ID.NO.45) | 1,747 | 6.66 |
| NONE |  |  | 367 | 0.00 |

CpG dinucleotides are underlined; oligonucleotides were synthesized with phosphorothioate modified backbones to improve their nuclease resistance. Measured by H thymidine incorporation after 48 hr culture with oligodeoxynucleotides at a 200 nM concentration as described in Example 1. Measured in lytic units.

Teleological Basis of Immunostimulatory, Nucleic Acids

Vertebrate DNA is highly methylated and CpG dinucleotides are under represented. However, the stimulatory CpG motif is common in microbial genomic DNA, but quite rare in vertebrate DNA. In addition, bacterial DNA has been reported to induce B cell proliferation and immunoglobulin (Ig) production, while mammalian DNA does not (Messina, J. P. et al., *J. Immunol.* 147:1759 (1991)). Experiments further described in Example 3, in which methylation of bacterial DNA with CpG methylase was found to abolish CpG pathway synergizes with B cell activation through the antigen receptor, B cells bearing antigen receptor specific for bacterial antigens would receive on e activation signal through cell membrane Ig and a second signal from bacterial DNA, and would therefore tend to be preferentially activated. The interrelationship of this pathway with other pathways of B cell activation provide a physiologic mechanism employing a polyclonal antigen to induce antigen-specific responses.

However, it is likely that B cell activation would not be totally nonspecific. B cells bearing antigen receptors specific for bacterial products could receive one activation signal through cell membrane Ig, and a second from bacterial DNA, thereby more vigorously triggering antigen specific immune responses. As with other immune defense mechanisms, the response to bacterial DNA could have undesirable consequences in some settings. For example, autoimmune responses to self antigens would also tend to be preferentially triggered by bacterial infections, since autoantigens could also provide a second activation signal to autoreactive B cells triggered by bacterial DNA. Indeed the induction of autoimmunity by bacterial infections is a common clinical observance. For example, the autoimmune disease systemic lupus erythematosus, which is: i) characterized by the production of anti-DNA antibodies; ii) induced by drugs which inhibit DNA methyltransferase (Comaccia, E. J. et al., *J. Clin. Invest.* 92:38 (1993)); and iii) associated with reduced DNA methylation (Richardson, B., L. et al., *Arth. Rheum* 35:647 (1992)), is likely triggered at least in part by activation of DNA-specific B cells through stimulatory signals provided by CpG motifs, as well as by binding of bacterial DNA to antigen receptors.

Further, sepsis, which is characterized by high morbidity and mortality due to massive and nonspecific activation of the immune system may be initiated by bacterial DNA and other products released from dying bacteria that reach concentrations sufficient to directly activate many lymphocytes. Further evidence of the role of CpG DNA in the sepsis syndrome is described in Cowdery, J., et. al., (1996) *the Journal of Immunology* 156:4570–4575.

Unlike antigens that trigger B cells through their surface Ig receptor, CpG-ODN did not induce any detectable $Ca^{2+}$ flux, changes in protein tyrosine phosphorylation, or IP 3 generation. Flow cytometry with FITC-conjugated ODN with or without a CpG motif was performed as described in Zhao, Q et al., (*Antisense Research and Development* 3:53–66 (1993)), and showed equivalent membrane binding, cellular uptake, efflux, and intracellular localization. This suggests that there may not be cell membrane proteins specific for CpG ODN. Rather than acting through the cell membrane, that data suggests that unmethylated CpG containing oligonucleotides require cell uptake for activity: ODN covalently linked to a solid Teflon support were nonstimulatory, as were biotinylated ODN immobilized on either avidin beads or avidin coated petri dishes. CpG ODN conjugated to either FITC or biotin retained full mitogenic properties, indicated no stearic hindrance.

Figure 7:
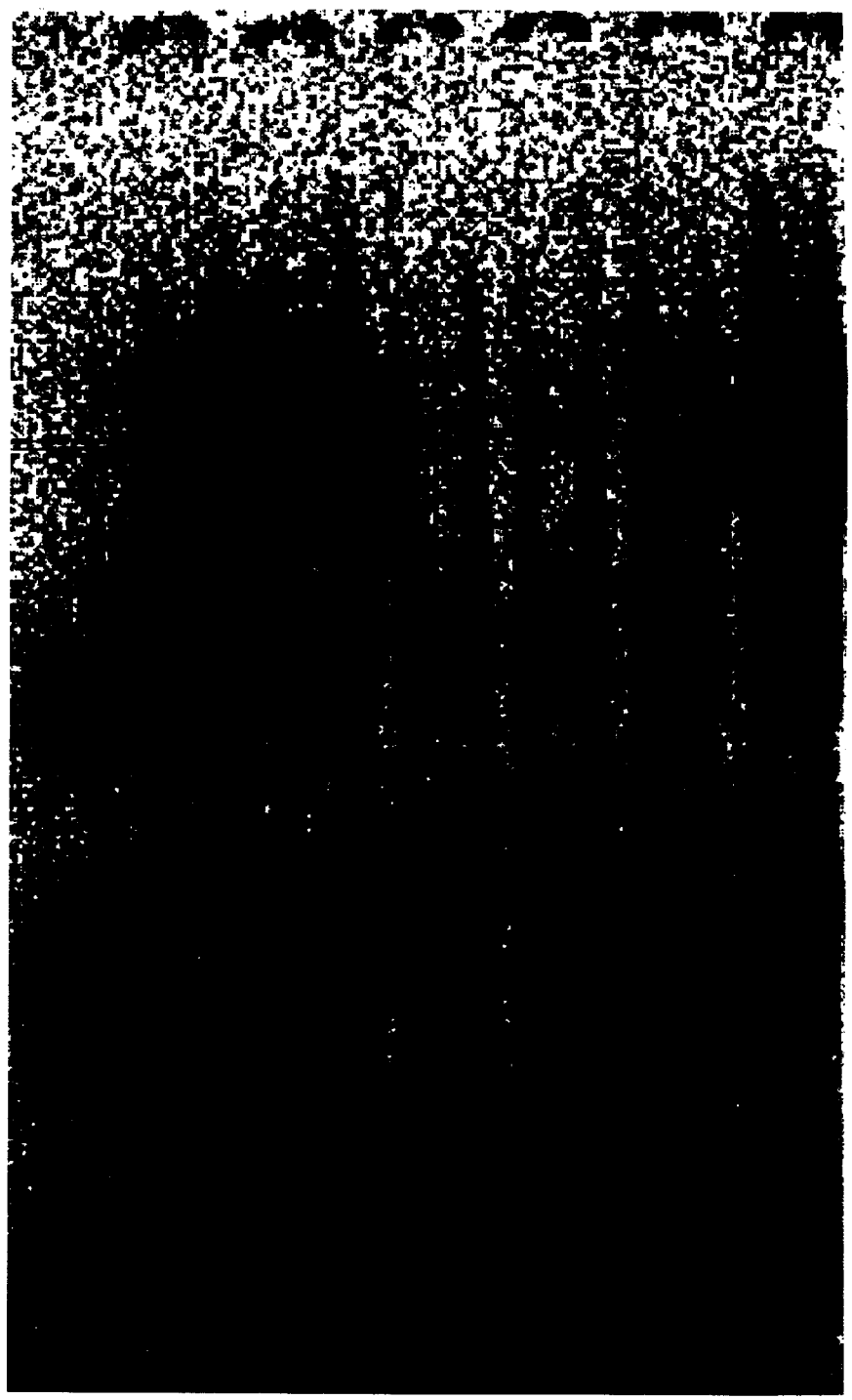
FIG. 7 is an autoradiograph showing NFκB mRNA induction in monocytes treated with *E. coli* (EC) DNA (containing unmethylated CpG motifs), control (CT) DNA (containing no unmethylated CpG motifs) and lipopolysaccharide (LPS) at various measured times, 15 and 30 minutes after contact.

Recent data indicate the involvement of the transcription factor NFkB as a direct or indirect mediator of the CpG effect. For example, within 15 minutes of treating B cells or monocytes with CpG DNA, the level of NFkB binding activity is increased (FIG. 7). However, it is not increased by DNA that does not contain CpG motifs. In addition, it was found that two different inhibitors of NFkB activation, PDTC and gliotoxin, completely block the lymphocyte stimulation by CpG DNA as measured by B cell proliferation or monocytic cell cytokine secretion, suggesting that NFkB activation is required for both cell types.

There are several possible mechanisms through which NFkB can be activated. These include through activation of various protein kinases, or through the generation of reactive oxygen species. No evidence for protein kinase activation induced immediately after CpG DNA treatment of B cells or monocytic cells have been found, and inhibitors of protein kinase A, protein kinase C, and protein tyrosine kinases had no effects on the CpG induced activation. k However, CpG DNA causes a rapid induction of the production of reactive oxygen species in both B cells and monocytic cells, as detected by the sensitive fluorescent dye dihydrorhodamine 123 as described in Royall, J. A., and Ischiropoulos, H. (*Archives of Biochemistry and Biophysics* 302:348–355 (1993)). Moreover, inhibitors of the generation of these reactive oxygen species completely block the induction of NFkB and the later induction of cell proliferation and cytokine secretion by CpG DNA.

Figure 8A:
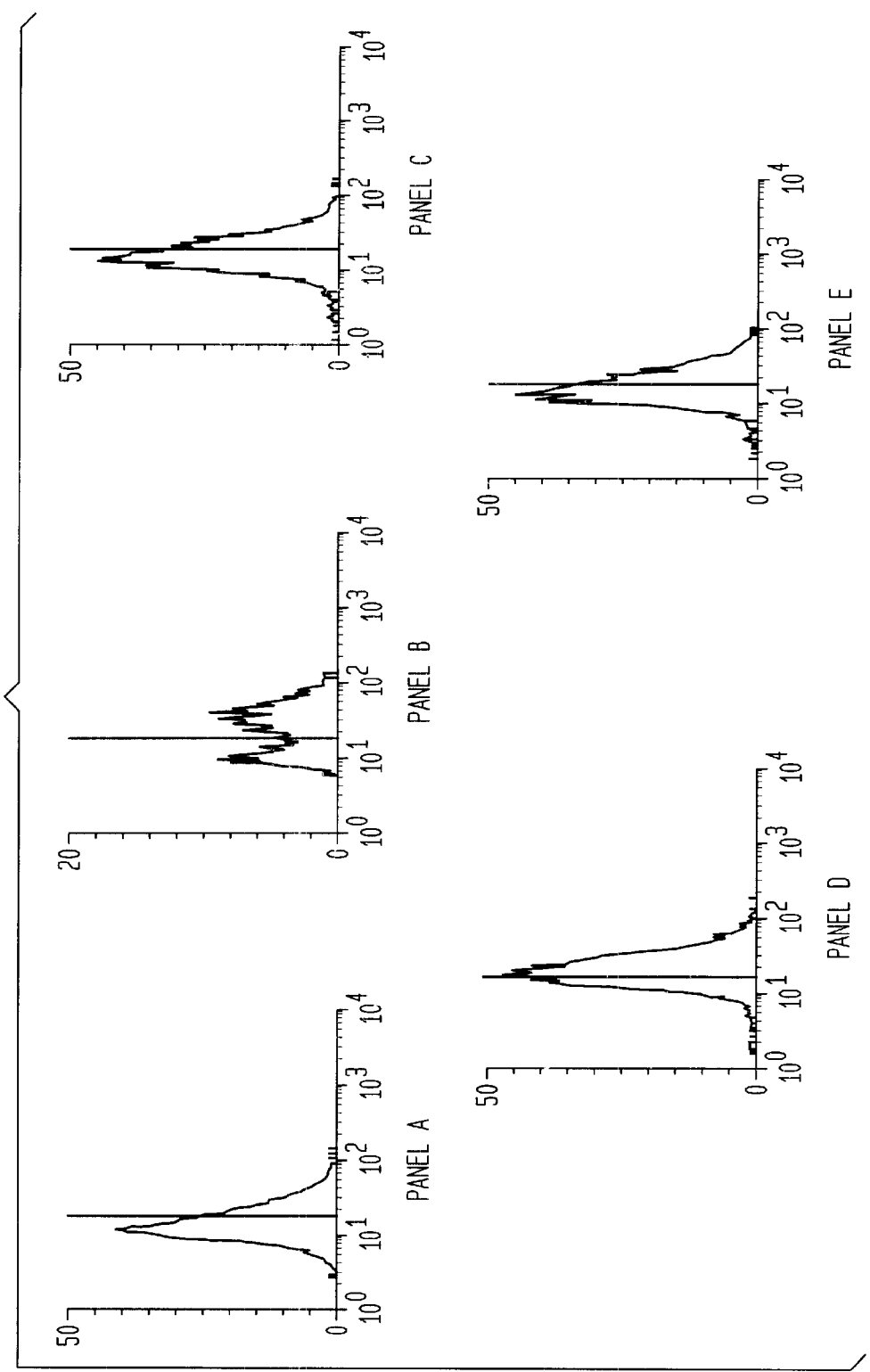
FIG. 8A shows the results from a flow cytometry study using mouse B cells with the dihydrorhodamine 123 dye to determine levels of reactive oxygen species. The dye only sample in Panel A of the figure shows the background level of cells positive for the dye at 28.6%. This level of reactive oxygen species was greatly increased to 80% in the cells treated for 20 minutes with PMA and ionomycin, a positive control (Panel B). The cells treated with the CpG oligo (TCCATGACGTTCCTGACGTT SEQ ID NO: 10) also showed an increase in the level of reactive oxygen species such that more than 50% of the cells became positive (Panel D). However, cells treated with an oligonucleotide with the identical sequence except that the CpGs were switched (TCCATGAGCTTCCTGAGTCT SEQ ID NO: 8) did not show this significant increase in the level of reactive oxygen species (Panel E).

Work backwards, the next question was how CpG DNA leads to the generation of reactive oxygen species so quickly. Previous studies by the inventors demonstrated that oligonucleotides and plasmid or bacterial DNA are taken up by cells into endosomes. These endosomes rapidly become acidified inside the cell. To determine whether this acidification step may be important in the mechanism through which CpG DNA activates reactive oxygen species, the acidification step was blocked with specific inhibitors of endosome acidification including chloroquine, monensin, and bafilomycin, which work through different mechanisms. FIG. 8A shows the results from a flow cytometry study using mouse B cells with the dihydrorhodamine 123 dye to determine levels of reactive oxygen species. The dye only sample in Panel A of the figure shows the background level of cells positive for the dye at 28.6%. as expected, this level of reactive oxygen species was greatly increased to 80% in the cells treated for 20 minutes with PMA and ionomycin, a positive control (Panel B). The cells treated with the CpG oligo also showed an increase in the level of reactive oxygen species such that more than 50% of the cells became positive (Panel D). However, cells treated with an oligonucleotide with the identical sequence except that the CpG was switched did not show this significant increase in the level of reactive oxygen species (Panel E).

Figure 8B:
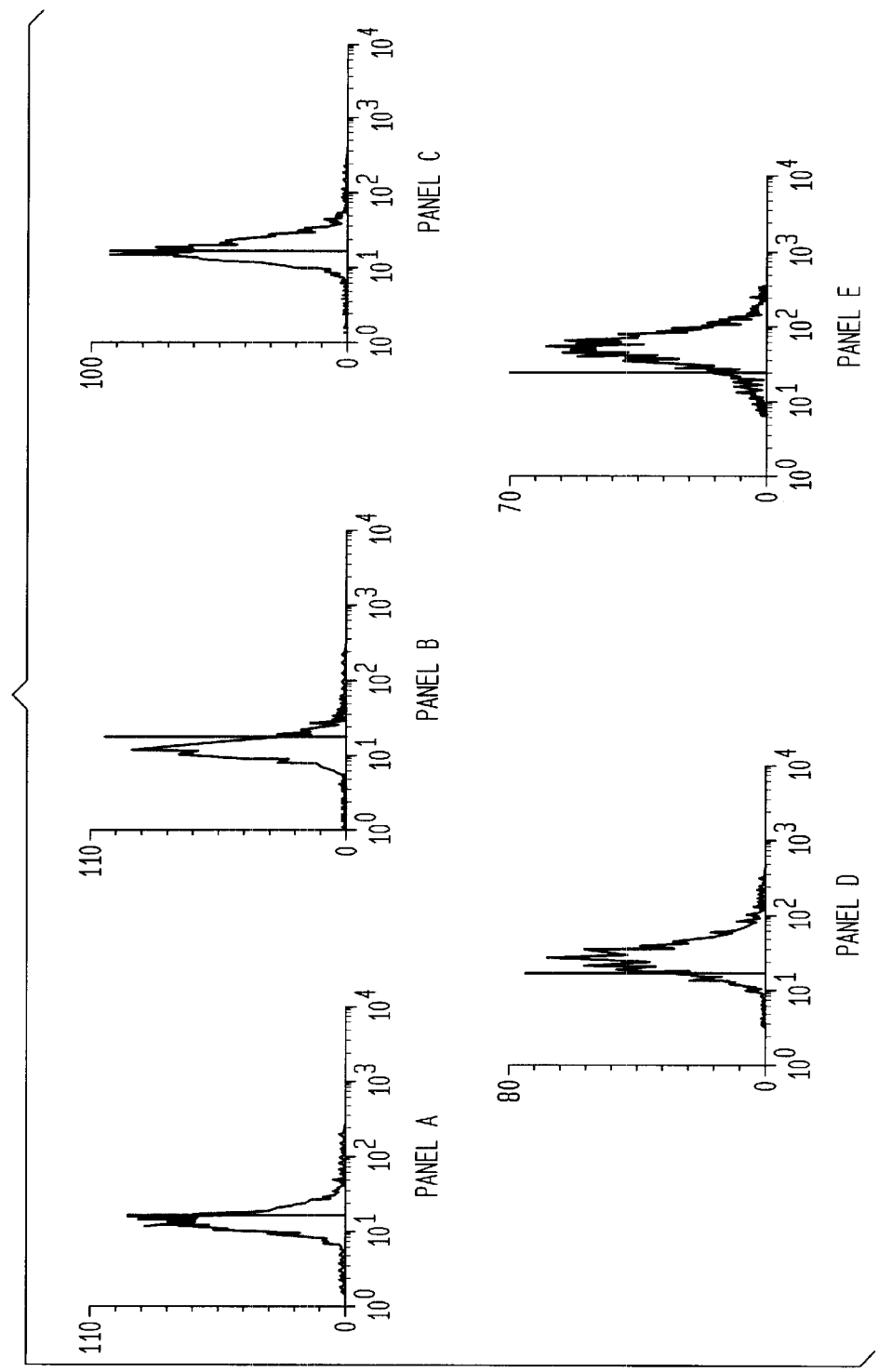
FIG. 8B shows the results from a flow cytometry study using mouse B cells in the presence of chloroquine with the dihydrorhodamine 123 dye to determine levels of reactive oxygen species. Chloroquine slightly lowers the background level of reactive oxygen species in the cells such that the untreated cells in Panel A have only 4.3% that are positive. Chloroquine completely abolishes the induction of reactive oxygen species in the cells treated with CpG DNA (Panel B) but does not reduce the level of reactive oxygen species in the cells treated with PMA and ionomycin (Panel E).

In the presence of chloroquine, the results are very different (FIG. 8B). Chloroquine slightly lowers the background level of reactive oxygen species in the cells such that the untreated cells in Panel A have only 4.3% that are positive. Chloroquine completely abolishes the induction of reactive oxygen species in the cells treated with CpG DNA (Panel B) but does not reduce the level of reactive oxygen species in t he cells treated with PMA and ionomycin (Panel E). This demonstrates that unlike the PMA plus ionomycin, the generation of reactive oxygen species following treatment of B cells with CpG DNA requires that the DNA undergo an acidification step in the endosomes. This is a completely novel mechanism of leukocyte activation. Chloroquine, monensin, and bafilomycin also appear to block the activation of NFkB by CpG DNA as well as the subsequent proliferation and induction of cytokine secretion.

Chronic Immune Activation by CpG DNA and Autoimmune Disorders

B cell activation by CpG DNA synergizes with signals through the B cell receptor. This raises the possibility that DNA-specific B cells may be activated by the concurrent binding of bacterial DNA to their antigen receptor, and by the co-stimulatory CpG-mediated signals. In addition, CpG DNA induces B cells to become resistant to apoptosis, a mechanism thought to be important for preventing immune responses to self antigens, such as DNA. Indeed, exposure to bDNA can trigger anti-DNA Ab production. Given this potential ability of CpG DNA to promote autoimmunity, it is therefore noteworthy that patients with the autoimmune disease systemic lupus erythematosus have persistently elevated levels of circulating plasma DNA which is enriched in hypomethylated CpGs. These findings suggest a possible role for chronic immune activation by CpG DNA in lupus etiopathogenesis.

A class of medications effective in the treatment of lupus is antimalarial drugs, such as chloroquine. While the therapeutic mechanism of these drugs has been unclear, they are known to inhibit endosomal acidification. Leukocyte activation by CpG DNA is not medicated through binding to a cell surface receptor, but requires cell uptake, which occurs via adsorptive endocytosis into an acidified chloroquine-sensitive intracellular compartment. This suggested the hypothesis that leukocyte activation by CpG DNA may occur in association with acidified endosomes, and might even be pH dependent. To test this hypothesis specific inhibitors of DNA acidification were applied to determine whether B cells or monocytes could respond to CpG DNA if endosomal acidification was prevented.

The earliest leukocyte activation event that was detected in response to CpG DNA is the production of reactive oxygen species (ROS), which is induced within five minutes in primary spleen cells and both B and monocyte cell lines. Inhibitors of endosomal acidification including chloroquine, bafilomycin A, and monensin, which have different mechanisms of action, blocked the CpG-induced generation of ROS, but had no effect on ROS generation mediated by PMA, or ligation of CD40 or IgM. These studies show that ROS generation is a common event in leukocyte activation through diverse pathways. This ROS generation is generally independent of endosomal acidification, which is required only for the ROS response to CpG DNA. ROS generation in response to CpG is not inhibited by the NFκB inhibitor gliotoxin, confirming that it is not secondary to NFκB activation.

To determine whether endosomal acidification of CpG DNA was also required for its other immune stimulatory effects were performed. Both LPS and CpG DNA induce similar rapid NFκB activation, increases in proto-oncogene mRNA levels, and cytokine secretion. Activation of NFκB by DNA depended on CpG motifs since it was not induced by bDNA treated with CpG methylase, nor by ODN in which bases were switched to disrupt the CpGs. Supershift experiments using specific antibodies indicated that the activated NFκB complexes included the p50 and p65 components. Not unexpectedly, NFκB activation in LPS- or CpG-treated cells was accompanied by the degradation of IκBα and IκBβ. However, inhibitors of endosomal acidification selectively blocked all of the CpG-induced but none of the LPS-induced cellular activation events. The very low concentration of chloroquine (<10 μM) that has been determined to inhibit CpG-mediated leukocyte activation is noteworthy since it is well below that required for antimalarial activity and other reported immune effects (e.g., 100–1000 μM). These experiments support the role of a pH-dependent signaling mechanism in mediating the stimulatory effects of CpG DNA.

TABLE 15

Specific blockade of CpG-induced TNF-α and IL-12 expression by inhibitors of endosomal acidification or NFκB activation

| activators | Medium | | Inhibitors: Bafilomycin (250 nM) | | Chloroquine (2.5 μg/ml) | | Monensin (10 μM) | | NAC (50 mM) | TPCK (50 μM) | Gliotoxin (0.1 μg/ml) | Bisgliotoxin (0.1 μg/ml) |
|---|---|---|---|---|---|---|---|---|---|---|---|---|
| | TNF-α | IL-12 | TNF-α | IL-12 | TNF-α | IL-12 | TNF-α | IL-12 | TNF-α | TNF-α | TNF-α | TNF-α |
| Medium | 37 | 147 | 46 | 102 | 27 | 20 | 22 | 73 | 10 | 24 | 17 | 41 |
| CpG ODN | 455 | 17,114 | 71 | 116 | 28 | 6 | 49 | 777 | 54 | 23 | 31 | 441 |
| LPS | 901 | 22,485 | 1370 | 4051 | 1025 | 12418 | 491 | 4796 | 417 | 46 | 178 | 1120 |

Table 15 legend IL-12 and TNF-α assays: The murine monocyte cell line J774 (1×10⁵ cells/ml for IL-12 or 1×10⁶ cells/ml for TNF-α), were cultured with or without the indicated inhibitors at the concentrations shown for 2 hr and then stimulated with the CpG oligodeoxynucleotide (ODN) 1826 (TCCATGACGTTCCTGACGTT SEQ ID NO:10) at 2 μM or LPS (10 μg/ml) for 4 hr (TNF-α) or 24 hr (IL-12) at which time the supernatant was harvested. ELISA for IL-12 or TNF-α (pg/ml) was performed on the supernatants essentially as described (A. K. Krieg, A.-K. Yi, S. Matson, T. J. Waldschmidt, G. A. Bishop, R. Teasdale, G. Koretzky and D. Klinman, *Nature* 374, 546 (1995); Yi, A.-K., D. M. Kilnman, T. L. Martin, S. Matson and A. M. Krieg, *J. Immunol.*, 157, 5394–5402 (1996); Krieg, A. M., *J. Lab. Clin. Med.*, 128, 128–133 (1996). Cells cultured with ODN that lacked CpG motifs did not induce cytokine secretion. Similar specific inhibition of CpG responses was seen with IL-6 assays, and in experiments using primary spleen cells or the B cell lines CH12.LX and WEHI-231.2.5 μg/ml of chloroquine is equivalent to <5 μM. Other inhibitors of NF-κB activation including PDTC and calpain inhibitors I and II gave similar results to the inhibitors shown. The results shown are representative of those obtained in ten different experiments.

Excessive immune activation by CpG motifs may contribute to the pathogenesis of the autoimmune disease systemic lupus erythematosus, which is associated with elevated levels of circulating hypomethylated CpG DNA. Chloroquine and related antimalarial compounds are effective therapeutic agents for the treatment of systemic lupus erythematosus and some other autoimmune diseases, although their mechanism of action has been obscure. Our demonstration of the ability of extremely low concentrations of chloroquine to specifically inhibit CpG-mediated leukocyte activation suggests a possible new mechanism for its beneficial effect. It is noteworthy that lupus recurrences frequently are thought to be triggered by microbial infection. Levels of bDNA present in infected tissues can be sufficient to induce a local inflammatory response. Together with the likely role of CpG DNA as a mediator of the sepsis syndrome and other diseases our studies suggest possible new therapeutic applications for the antimalarial drugs that act as inhibitors of endosomal acidification.

CpG-induced ROS generation could be an incidental consequence of cell activation, or a signal that mediates this activation. The ROS scavenger N-acetyl-L-cysteine (NAC) blocks CpG-induced NFκB activation, cytokine production, and B cell proliferation, suggesting a casual role for ROS generation in these pathways. These data are compatible with previous evidence supporting a role for ROS in the activation of NFκB. WEHI-231 B cells ($5 \times 10^5$ cells/ml) were precultured for 30 minutes with or without chloroquine (5 μg/ml [<10 μM]) or gliotoxin (0.2 μg/ml). Cell aliquots were then cultured as above for 10 minutes in RPMI medium with or without a CpG ODN (1826) or non-CpG ODN (1911) at 1 μM or phorbol myristate acetate (PMA) plus ionomycin (iono). Cells were then stained with dihydrorhodamine-123 and analyzed for intracellular ROS production by flow cytometry as described (A. K. Krieg, A.-K. Yi, S. Matson, T. J. Waldschmidt, G. A. Bishop, R. Teasdale, G. Koretzky and D. Klinman, *Nature* 374, 546 (1995); Yi, A.-K., D. M. Klinman, T. L. Martin, S. Matson and A. M. Krieg, *J. Immunol.*, 157, 5394–5402 (1996); Krieg, A. M, *J. Lab. Clin. Med.*, 128, 128–133 (1996)). J1774 cells, a monocytic line, showed similar pH-dependent CpG induced ROS responses. In contrast, CpG DNA did not induce the generation of extracellular ROS, nor any detectable neutrophil ROS. The concentrations of chloroquine (and those used with the other inhibitors of endosomal acidification) prevented acidification of the internalized CpG DNA using fluorescein conjugated ODN as described by Tonkinson, et al., (*Nucl. Acids Res.* 22, 4268 (1994); A. M. Krieg, In: *Delivery Strategies for Antisense Oligonucleotide Therapeutics*. Editor, S. Akhtar, CRC Press, Inc., pp. 177(1995)). At higher concentrations than those required to inhibit endosomal acidification, nonspecific inhibitory effects were observed. Each experiment was performed at least three times with similar results.

While NFκB is known to be an important regulator of gene expression, it's role in the transcriptional response to CpG DNA was uncertain. To determine whether this NFκB activation was required for the CpG mediated induction of gene expression cells were activated with CpG DNA in the presence or absence of pyrrolidine dithiocarbamate (PDTC), an inhibitor of IκB phosphorylation. These inhibitors of NFκB activation completely blocked the CpG-induced expression of protooncogene and cytokine mRNA and protein, demonstrating the essential role of NFκB as a mediator of these events. None of the inhibitors reduced cell viability under the experimental conditions used in these studies. A J774, a murine monocyte cell line, was cultured in the presence of calf thymus (CT), *E. coli* (EC), or methylated *E. coli* (mEC) DNA (methylated with CpG methylase as described) at 5 μg/ml or a CpG oligodeoxynucleotide (ODN 1826; Table 15) or a non-CpG ODN (ODN 1745; TCCATGAGCTTCCTGAGTCT, SEQ. ID. NO: 8) at 0.75 μM for 1 hr, following which the cells were lysed and nuclear extracts prepared. A double stranded ODN containing a consensus NFκB site was 5' radiolabeled and used as a probe for EMSA essentially as described (J. D. Dignam, R. M. Lebovitz and R. G. Roeder, *Nucleic Acids Res.* 11, 1475 (1983); M. Briskin, M. Damore, R. Law, G. Lee, P. W. Kincade, C. H. Sibley, M. Kuehl and R. Wall, *Mol. Cell. Biol.* 10, 422 (1990)). The position of the p50/p65 heterodimer was determined by supershifting with specific Ab to p65 and p50 (Santa Cruz Biotechnology, Santa Cruz, Calif.). Chloroquine inhibition of CpG-induced but not LPS-induced NFκB activation was established using J774 cells. The cells were precultured for 2 hr in the presence or absence of chloroquine (20 μg/ml) and then stimulated as above for 1 hr with either EC DNA, CpG ODN, non-CpG ODN or LPS (1 μg/ml). Similar chloroquine sensitive CpG-induced activation of NFκB was seen in a B cell line, WEHI-231 and primary spleen cells. These experiments were performed three times over a range of chloroquine concentrations form 2.5 to 20 μg/ml with similar results.

It was also established that CpG-stimulated mRNA expression requires endosomal acidification and NFκB activation in B cells and monocytes. J774 cells ($2 \times 10^6$ cells/ml) were cultured for 2 hr in the presence or absence of chloroquine (2.5 μg/ml [<5 μM]) or N-tosyl-L-phenylalanine chlorometryl ketone (TPCK: 50 μM), a serine/threonine protease inhibitor that prevents IκB proteolysis and thus blocks NFκB activation. Cells were then stimulated with the addition of *E. coli* DNA (EC: 50 μg/ml), calf thymus DNA (CT: 50 μg/ml), LPS (10 μg/ml), CpG ODN (1826; 1 μM), or control non CpG ODN (1911; 1 μM) for 3 hr. WEHI-231 B cells ($5 \times 10^5$ cells/ml) were cultured in the presence or absence of gliotoxin (0.1 μg/ml) or bisgliotoxin (0.1 μg/ml) for 2 hrs and then stimulated with a CpG ODN (1826), or control non-CpG ODN (1911; TCCAGGACTTTCCTCAGGTT, SEQ. ID. NO. 97) at 0.5 μM for 8 hr. In both cases, cells were harvested and RNA was prepared using RNAzol following the manufacturer's protocol. Multi-probe RNASE protection assay was performed as described (A.-K. Yi, P. Hornbeck, D. E. Lafrenz and A. M. Krieg, *J. Immunol.*, 157, 4918–4925 (1996). Comparable amounts of RNA were loaded into each lane by using ribosomal mRNA as a loading control (L32). These experiments were performed three times with similar results.

The results indicate that leukocytes respond to CpG DNA through a novel pathway involving the pH-dependent generation of intracellular ROS. The pH dependent step may be the transport or processing of the CpG DNA, the ROS generation, or some other event. ROS are widely thought to be second messengers in signaling pathways in diverse cell types, but have not previously been shown to mediate a stimulatory signal in B cells.

Presumably, there is a protein in or near the endosomes that specifically recognizes DNA containing CpG motifs and leads to the generation of reactive oxygen species. To detect any protein in the cell cytoplasm that may specifically bind CpG DNA, electrophoretic mobility shift assays (EMSA) were used with 5' radioactively labeled oligonucleotides with or without CpG motifs. A band was found that appears to represent a protein binding specifically to single stranded oligonucleotides that have CpG motifs, but not to oligonucleotides that lack CpG motifs or to oligonucleotides in which the CpG motif has been methylated. This binding activity is blocked if excess of oligonucleotides that contain the NFκB binding site was added. This suggests that an NFκB or related protein is a component of a protein or protein complex that binds the stimulatory CpG oligonucleotides.

No activation of CREB/ATF proteins was found at time points where NFκB was strongly activated. These data therefore do not provide proof the NFκB proteins actually bind to the CpG nucleic acids, but rather that the proteins are required in some way for the CpG activity. It is possible that a CREB/ATF or related protein may interact in some way with NFκB proteins or other proteins thus explaining the remarkable similarity in the binding motifs for CREB proteins and the optimal CpG motif. It remains possible that the oligos bind to a CREB/ATF or related protein, and that this leads to NFκB activation.

Alternatively, it is very possible that the CpG nucleic acids may bind to one of the TRAF proteins that bind to the cytoplasmic region of CD40 and mediate NFkB activation when CD40 is cross-linked. Examples of such TRAF proteins include TRAF-2 and TRAF-5.

Method for Making Immunostimulatory Nucleic Acids

For use in the instant invention, nucleic acids can be synthesized de novo using any of a number of procedures well known in the art. For example, the b-cyanoethyl phosphoramidite method (S. L. Beaucage and M. H.

Caruthers, (1981) *Tet. Let.* 22:1859); nucleoside H-phosphonate method (Garegg et al., (1986) *Tet. Let.* 27:4051–4054; Froehler et al., (1986) *Nucl. Acid. Res* 14:5399–5407; Garegg eg al., (1986) *Tet. Let.* 27:4055–4058, Gaffney et al., (1988) *Tet. Let.* 29:2619–2622). These chemistries can be performed by a variety of automated oligonucleotide synthesizers available in the market. Alternatively, oligonucleotides can be prepared from existing nucleic acid sequences (e.g. genomic or cDNA) using known techniques, such as those employing restriction enzymes, exonucleases or endonucleases.

For use in vivo, nucleic acids are preferably relatively resistant to degradation (e.g. via endo- and exo- nucleases). Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made e.g as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. And Peyman, A. (1990) *Chem. Rev.* 90:544; Goodchild, J. (1990) *Bioconjugate Chem.* 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (e.g. B-cell, monocytic cell and natural killer (NK) cell) surfaces and/or increased cellular uptake by target cells to form a "nucleic acid delivery complex". Nucleic acids can be ionically, or covalently associated with appropriate molecules using techniques which are well known in the art. A variety of coupling or crosslinking agents can be sued e.g. Protein A, carbodiimide, and N-succinimidyl-3-(2-pyridyldithio) propionate (SPDP). Nucleic acids can alternatively be encapsulated in liposomes or virosomes using well-known techniques.

Therapeutic Uses of Immunostimulatory Nucleic Acid Molecules

Based on their immunostimulatory properties, nucleic acid molecules containing at least one unmethylated CpG dinucleotide can be administered to a subject in vivo to treat an "immune system deficiency". Alternatively, nucleic acid molecules containing at least one unmethylated CpG dinucleotide can be contacted with lymphocytes (e.g. B cells, monocytic cells or NK cells) obtained from a subject having an immune system deficiency ex vivo and activated lymphocytes can then be re-implanted in the subject.

As reported herein, in response to unmethylated CpG containing nucleic acid molecules, an increased number of spleen cells secrete IL-6, IL-12, IFNγ, IFN-α, IFN-β, IL-1, IL-3, IL-10, TNF-α, TNF-β, GM-CSF, RANTES, and probably others. The increased IL-6 expression was found to occur in B cells, CD4$^+$T cells and monocytic cells.

Immunostimulatory nucleic acid molecules can also be administered to a subject in conjunction with a vaccine to boost a subject's immune system and thereby effect a better response from the vaccine. Preferably the immunostimulatory nucleic acid molecule is administered slightly before or at the same time as the vaccine. A conventional adjuvant may optionally be administered in conjunction with the vaccine, which is minimally comprised of an antigen, as the conventional adjuvant may further improve the vaccination by enhancing antigen absorption.

When the vaccine is a DNA vaccine at least two components determine its efficacy. First, the antigen encoded by the vaccine determines the specificity of the immune response. Second, if the backbone of the plasmid contains CpG motifs, its functions as an adjuvant for the vaccine. Thus, CpG DNA acts as an effective "danger signal" and causes the immune system to respond vigorously to new antigens in the area. This mode of action presumably results primarily from the stimulatory local effects of CpG DNA on dendritic cells and other "professional" antigen presenting cells, as well as from the co-stimulatory effects on B cells.

Immunostimulatory oligonucleotides and unmethylated CpG containing vaccines, which directly activate lymphocytes and co-stimulate an antigen-specific response, are fundamentally different from conventional adjuvants (e.g aluminum precipates), which are inert when injected alone and are thought to work through absorbing the antigen and thereby presenting it more effectively to immune cells. Further conventional adjuvants only work for certain antigens, only induce an antibody (humoral) immune response (Th2), and are very poor at inducing cellular immune responses (Th1). For many pathogens, the humoral response contributes little to protection, and can even be detrimental.

In addition, an immunostimulatory oligonucleotide can be administered prior to along with or after administration of a chemotherapy or immunotherapy to increase the responsiveness of the malignant cells to subsequent chemotherapy or immunotherapy or to speed the recovery of the bone marrow through induction of restorative cytokines such as GM-CSF. CpG nucleic acids also increase natural killer cell lytic activity and antibody dependent cellular cytotoxicity (ADCC). Induction of NK activity and ADCC may likewise be beneficial in cancer immunotherapy, alone or in conjunction with other treatments.

Another use of the described immunostimulatory nucleic acid molecules is in desensitization therapy for allergies, which are generally caused by IgE antibody generation against harmless allergens. The cytokines that are induced by unmethylated CpG nucleic acids are predominantly of a class called "Th1" which is most marked; by a cellular immune response and is associated with Il-12 and IFN-γ. The other major type of immune response is termed a Th2 immune response, which is associated with more of an antibody immune response and with the production of IL-4, Il-5 and IL-10. In general, it appears that allergic diseases are mediated by Th2 type immune responses and autoimmune diseases by Th1 immune response. Based on the ability of the immunostimulatory nucleic acid molecules to shift the immune response in a subject from a Th2 (which is associated with production of IgE antibodies and allergy) to a Th1 response (which is protective against allergic reactions), an effective dose of an immunostimulatory nucleic acid (or a vector containing a nucleic acid) alone or in conjunction with an allergen can be administered to a subject to treat or prevent an allergy.

Nucleic acids containing unmethylated CpG motifs may also have significant therapeutic utility in the treatment of asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines.

As described in detail in the following Example 12, oligonucleotides containing an unmethylated CpG motif (I, e,. TCCATGA<u>CG</u>TTCCTGA<u>CG</u>TT; SEQ ID NO. 10) but not a control oligonucleotide (TCCATGAGCTTCCTGAGTCT; SEQ ID NO. 8) prevented the development of an inflammatory cellular infiltrate and eosinophilia in a murine model of asthma. Furthermore, the suppression of eosinophilic inflammation was associated with a suppression of a Th2 response and induction of a Th1 response.

For use in therapy, an effective amount of an appropriate immunostimulatory nucleic acid molecule alone or formulated as a delivery complex can be administered to a subject by any mode allowing the oligonucleotide to be taken up by the appropriate target cells (e.g., B-cells and monocytic cells). Preferred routes of administration include oral and transdermal (e.g., via a patch). Examples of other routes of administration include injection (subcutaneous, intravenous, parenteral, intraperitoneal, intrathecal, etc.). The injection can be in a bolus or a continuous infusion.

A nucleic acid alone or as a nucleic acid delivery complex can be administered in conjunction with a pharmaceutically acceptable carrier. As used herein, the phrase "pharmaceutically acceptable carrier" is intended to include substances that can be coadministered with a nucleic acid or a nucleic acid delivery complex and allows the nucleic acid to perform its indicated function. Examples of such carriers include solutions, solvents, dispersion media, delay agents, emulsions and the like. The use of such media for pharmaceutically active substances are well known in the art. Any other conventional carrier suitable for use with the nucleic acids falls within the scope of the instant invention.

The term "effective amount" of a nucleic acid molecule refers to the amount necessary or sufficient to realize a desired biologic effect. For example, an effective amount of a nucleic acid containing at least one unmethylated CpG for treating an immune system deficiency could be that amount necessary to eliminate a tumor, cancer, or bacterial, viral or fungal infection. An effective amount for use as a vaccine adjuvant could be the amount useful for boosting a subjects immune response to a vaccine. An "effective amount" for treating asthma can be that amount; useful for redirecting a Th2 type of immune response that is associated with asthma to a Th1 type of response. The effective amount for any particular application can vary depending on such factors as the disease or condition being treated, the particular nucleic acid being administered (e.g the number of unmethylated CpG motifs or their location in the nucleic acid), the size of the subject, or the severity of the disease or condition. One of ordinary skill in the art can empirically determine the effective amount of a particular oligonucleotide without necessitating undue experimentation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Effects of ODNs on B Cell Total RNA Synthesis and Cell Cycle

B cells were purified from spleens obtained from 6–12 week old specific pathogen free DBA/2 or BXSB mice (bred in the University of Iowa animal care facility; no substantial strain differences were noted) that were depleted of T cells with anti-Thy-1.2 and complement and centrifugation over lymphocyte M(Cedarlane Laboratories, Homby, Ontario, Canada) ("B cells"). B cells contained fewer than 1% CD4' or CD8$^+$ cells. 8×10$^4$B cells were dispensed in triplicate into 96 well microtiter plates in 100 μl RPMI containing 10% FBS (heat inactivated to 65° C. for 30 min.), 50 μM 2-mercaptoethanol, 100 U/ml penicillin, 100 ug/ml streptomycin, and 2 mM L-glutamate. 20 μM ODN were added at the start of culture for 20 h at 37° C., cells pulsed with 1 μCi of $^3$H uridine, and harvested and counted 4 hr later. Ig secreting B cells were enumerated using the ALISA spot assay after culture of whole spleen cells with ODN at 20 μM for 48 hr. Data, reported in Table 1, represents the stimulation index compared to cell cultured without ODN. $^3$H thymidine incorporation assays showed similar results, but with some nonspecific inhibition by thymidine released from degraded ODN (Matson. S and A. M. Krieg (1992) Nonspecific suppression of $^3$H-thymidine incorporation by control oligonucleotides. *Antisense Research and Development* 2:325).

Example 2

Effects of ODN on Production of IgM from B Cells

Single cell suspensions form the spleens of freshly killed mice were treated with anti-Thyl, anti-CD4, and anti-CD8 and complement by the method of Leibson et al., *J. Exp. Med.* 154:1681 (1981)). Resting B cells (<02% T cell contamination) were isolated from the 63–70% band of a discontinuous Percoll gradient by the procedure of DeFranco et al, *J. Exp. Med.* 155:1523 (1982). These were cultured as described above in 30 μg/ml LPS for 48 hr. The number of B cells actively secreting IgM was maximal at this time point, as determined by ELIspot assay (Klinman, D. M. et al. *J. Immunol* 144:506 (1990)). In that assay, B cells were incubated for 6 hrs on anti-Ig coated microtiter plates. The Ig they produced (>99% IgM) was detected using phosphatase-labeled anti-Ig (Southern Biotechnology Associated, Birmingham, Ala.). The antibodies produced by individual B cells were visualized by addition of BCIP (Sigma Chemical Co., St. Louis Mo.) which forms an insoluble blue precipitate in the presence of phosphatase. The dilution of cells producing 20–40 spots/well was used to determine the total number of antibody-secreting B cells/sample. All assays were performed in triplicate (data reported in Table 1). In some experiments, culture supernatants were assayed for IgM by ELISA, and showed similar increased in response to CpG-ODN.

Example 3

B Cell Stimulation by Bacterial DNA

DBA/2 B cells were cultured with no DNA or 50 μg/ml of a (Micrococcus lysodeikticus; b) NZB/N mouse spleen; and c) NSF/N mouse spleen genomic DNAs for 48 hours, then pulsed with $^3$H thymidine for 4 hours prior to cell harvest. Duplicate DNA samples were digested with DNASE I for 30 minutes at 37° C. prior to addition to cell cultures. *E coli* DNA also induced an 8.8 fold increase in the number of IgM secreting B cells by 48 hours using the ELISA spot assay.

DBA/2 B cells were cultured with either no additive, 50 μg/ml LPS or the ODN 1; 1a; 4; or 4a at 20 uM. Cells were cultured and harvested at 4, 8, 24 and 48 hours. BXSB cells were cultured as in Example 1 with 5, 10, 20, 40 or 80 μM of ODN 1; 1a; 4; or 4a or LPS. In this experiment, wells with no ODN had 3833 cpm. Each experiment was performed at least three times with similar results. Standard deviations of the triplicate wells were <5%.

Example 4

Effects of ODN on Natural Killer (NK) Activity $10 \times 10^6$ C57BL/6 spleen cells were cultured in two ml RPMI (supplemented as described for Example 1) with or without 40 μM CpG or non-CpG ODN for forty-eight hours. Cells were washed, and then used as effector cells in a short term $^{51}$Cr release assay with YAC-1 and 2C11, two NK sensitive target cell lines (Ballas, Z. K. et al. (1993) j. IMMUNOL. 150:17). Effector cells were added at various concentrations to $10^4$ $^{51}$Cr-labeled target cells in V-bottom microtiter plates in 0.2 ml, and incubated in 5% $CO_2$ for 4 hr. At 37° C. Plates were then centrifuged, and an aliquot of the supernatant counted for radioactivity. Percent specific lysis was determined by calculating the ratio of the $^{51}$Cr released in the presence of effector cells minus the $^{51}$Cr released when the target cells are cultured alone, over the total counts released after cell lysis in 2% acetic acid minus the $^{51}$Cr cpm released when the cells are cultured alone.

Example 5

In vivo Studies with CVG Phosphorothioate ODN

Mice were weighted and injected 1P with 0.25 ml of sterile PBS or the indicated phosphorothioate ODN dissolved in PBS. Twenty four hours later, spleen cells were harvested, washed, and stained for flow cytometry using phycoerythrin conjugated 6B2 to gate on B cells in conjunction with biotin conjugated anti Ly-6A/E or anti-Ia$^d$ (Pharmingen, San Diego, Calif.) or anti-Bla-1 (Hardy, R. R. et al., J. Exp. Med 159:1169 (1984). Two mice were studied for each condition and analyzed individually.

Example 6

Titration of Phosphorothioate ODN for B Cell Stimulation

B cells were cultured with phosphorothioate ODN with the sequence of control ODN 1a or the CpG ODN 1d and 3Db and then either pulsed after 20 hr with $^3$H uridine or after 44 hr with $^3$H thymidine before harvesting and determining cpm.

Example 7

Rescue of B Cells from Apoptosis

WEHI-231 cells ($5 \times 10^4$/well) were cultured for 1 hr. At 37° C. in the presence or absence of LPS or the control ODN 1a or the CpG ODN 1d and 3Db before addition of anti-IgM (1 μ/ml). Cells were cultured for a further 20 hr. Before a 4 hr. Pulse with 2 μCi/well $^3$H thymidine. In this experiment, cells with no ODN or anti-IgM gave $90.4 \times 10^3$ cpm of $^3$H thymidine incorporation by addition of anti-IgM. The phosphodiester ODN shown in Table 1 gave similar protection, though some nonspecific suppression due to ODN degradation. Each experiment was repeated at least 3 times with similar results.

Example 8

In vivo Induction of Murine IL-6

DBA/2 female mice (2 mos. old) were injected IP with 500 g CpG or control phosphorothioate ODN. At various time points after injection, the mice were bled. Two mice were studied for each time point. IL-6 was measured by Elisa, and IL-6 concentration was calculated by comparison to a standard curve generate using recombinant IL-6. The sensitivity of the assay was 10 pg/ml. Levels were undetectable after 8 hrs.

Example 9

Systemic Induction of Murine IL-6 Transcription

Mice and cell lines. DBA/2, BALB/c, and C3H/HeJ mice at 5–10 wk of age were used as a source of lymphocytes. All mice were obtained from The Jackson Laboratory (Bar Harbor, Me.), and bred and maintained under specific pathogen-free conditions in the University of Iowa Animal Care Unit. The mouse B cell line CH12.LX was kindly provided by Dr. G. Bishop (University of Iowa, Iowa City).

Cell preparation. Mice were killed by cervical dislocation. Single cell suspensions were prepared aseptically from the spleens from mice. T cell depleted mouse splenocytes were prepared by using anti-Thy-1.2 and complement and centrifugation over lymphocyte M (Cedarlane Laboratories, Hornby, Ontario, Canada) as described (Krieg, A. M. et al., (1989) A role for endogenous retroviral sequences in the regulation of lymphocyte activation. J. Immunol 143:2448).

ODN and DNA. Phosphodiester oligonucleotides (O—ODN) and the backbone modified phosphorothioate oligonucleotides (S—ODN) were obtained from the DNA Core facility at the University of Iowa or from Operon Technologies (Alameda, Calif.). E. coli DNA (Strain B) and calf thymus DNA were purchased from Sigma (St. Louis, Mo.). All DNA and ODN were purified by extraction with phenol:chloroform:isoamyl alcohol (25:24:1) and/or ethanol precipitation. E. coli and calf thymus DNA were single stranded prior to use by boiling for 10 min. followed by cooling on ice for 5 min. For some experiments, E. coli and calf thymus DNA were digested with DNase 1(2U/ug of DNA) at 37° C. for 2 hr in 1×SSC with 5 mM MgC12. To methylate the cytosine in CpG dinucleotide in E. coli DNA, E. coli DNA was treated with CpG methylase (M. SssI; 2U/μg of DNA) in NEBuffer 2 supplemented with 160 μM S-adenosyl methionine and incubated overnight at 37° C. Methylated DNA was purified as above. Efficiency of methylation was confirmed by Hpa II digestion followed by analysis by gel electrophoresis. All enzymes were purchased from New England Biolabs (Beverly, Mass.). LPS level in ODN was less than 12.5 ng/mg and E. coli and calf thymus DNA contained less than 2.5 ng of LPS/mg of DNA by Limulus assay.

Cell Culture. All cells were cultured at 37° C. in a 5% $CO_2$ humidifier incubator maintained in RPMI-1640 supplemented with 10% (v/v) heat inactivated fetal calf serum (FCS), 1.5 mM L-glutamine, 50 μ/ml), CpG or non-CpG phosphodiester ODN (O—ODN) (20 μM), phosphorothioate ODN (S—ODN) (0.5 μM), or E. coli or calf thymus DNA (50 μg/ml) at 37° C. for 24 hr. (for IL-6 production) or 5 days (for IgM production). Concentrations of stimulants were chosen based on preliminary studies with titrations. In some cases, cells were treated with CpG O—ODN along with various concentrations (1–10 μg/ml) of neutralizing rat IgGl antibody against murine IL-6 (hybridoma MP5-20F3) or control rat IgGl mAB to E. coli b-galactosidase (hybridoma GL 113; ATCC, Rockville, Md.) (20) for 5 days. At the end of incubation, culture supernatant fractions were analyzed by ELISA as below.

In vivo induction of IL-6 and IgM BALB/c mice were injected intravenously (iv) with PBS, calf thymus DNA (200

μg/100 μl PBS/mouse), E. coli DNA (200 μg/100 μl PBS/mouse), or CpG or non-CpG S—ODN (200 μg/100 μl PBS/mouse). Mice (two/group) were bled by retroorbital puncture and sacrificed by cervical dislocation at various time points. Liver, spleen, thymus, and bone marrow were removed by RNA was prepared from those organs using RNAzol B (Tel-Test, Friendswood, Tex.) according to the manufactures protocol.

ELISA. Flat-bottomed Immun 1 plates (Dynatech Laboratories, Inc., Chantilly, Va.) were coated with 100 μl/well of anti-mouse IL-6 mAb (MP5-20F3) (2 μg/ml) or anti-mouse IgM μ-chain specific (5 μg/ml; Sigma, St. Louis, Mo.) in carbonate-bicarbonate, pH 9.6 buffer (15 nM $Na_2CO_3$, 35 mM $NaHCO_3$) overnight at 4° C. The plates were then washed with TPBS (0.5 mM $MgCl_2 \cdot 6H_2O$, 2.68 mM KCl, 1.47 mM $KH_2PO_4$, 0.14 M NaCl, 6.6 mM $K_2HPO_4$, 0.5% Tween 20) and blocked with 10% FCS and TPBS for 2 hr at room temperature and then washed again. Culture supernatants, mouse sera, recombinant mouse IL-6 (Pharmigen, San Diego, Calif.) or purified mouse IgM (Calbiochem, San Diego, Calif.) were appropriately diluted in 10% FCS and incubated in triplicate wells for 6 hr at room temperature. The plates were washed and 100 μl/well of biotinylated rat anti-mouse IL-6 monoclonal antibodies (MP5-32C11, Pharmingen, San Diego, Calif.) (1 μg/ml in 10% FCS) or biotinylated anti-mouse Ig (Sigma, St. Louis, Mo.) were added and incubated for 45 min. at room temperature following washes with TPBS. Horseradish peroxidase (HRP) conjugated avidin (Bio-rad Laboratories, Hercules, Calif.) at 1:4000 dilution in 10% FCS (100 μl/well) was added and incubated at room temperature for 30 min. The plates were washed and developed with o-phenylenediamine dihydrochloride (OPD; Sigma, St. Louis Mo.) 0.05 M phosphate-citrate buffer, pH 5.0, for 30 min. The reaction was stopped with 0.67 N $H_2SO_4$ and plates were read on a microplate reader (Cambridge Technology, Inc., Watertown, Mass.) at 490–600 nm. The results are shown in FIGS. 1 and 2.

Figure 3:
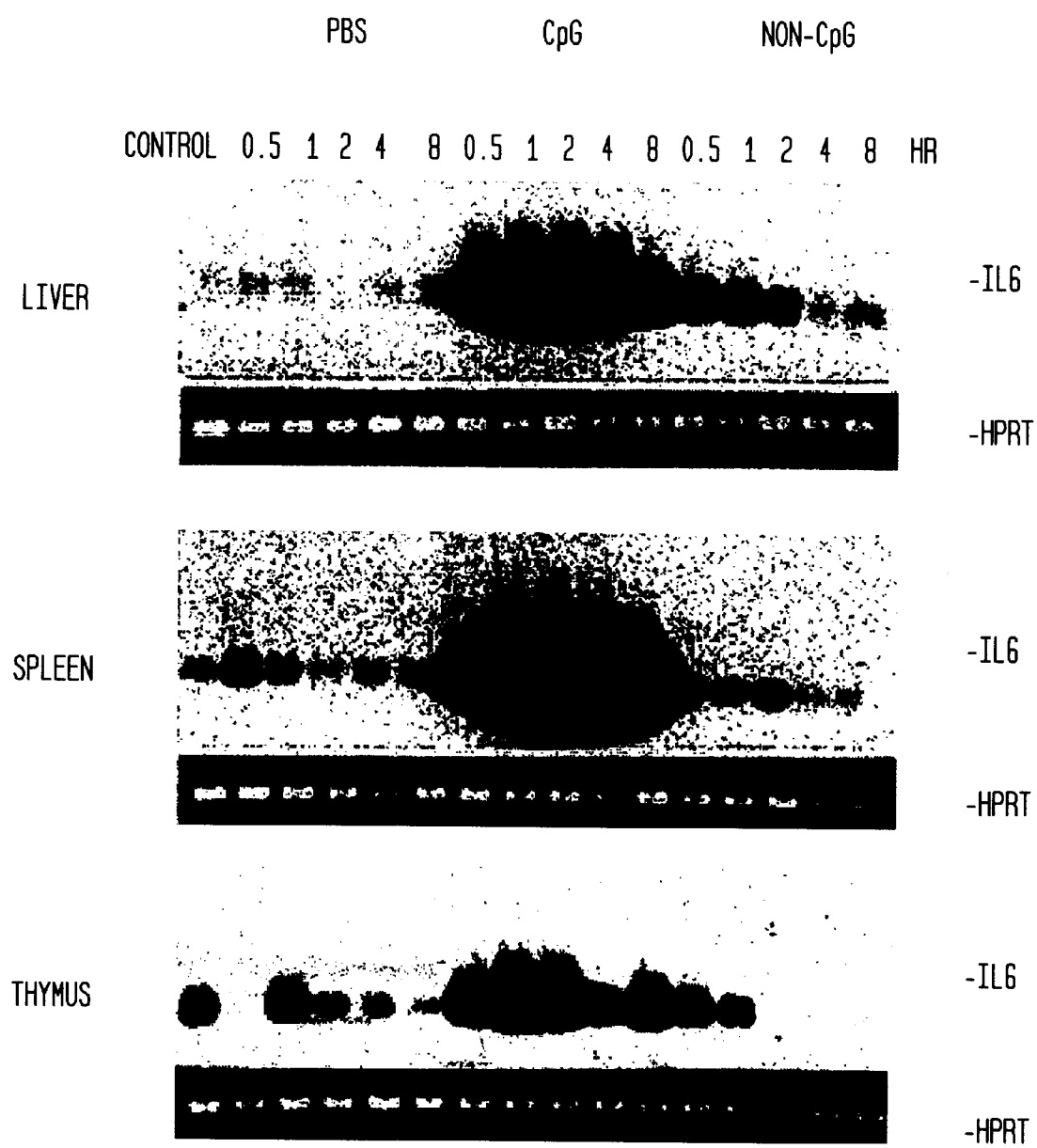
FIG. 3 is an autoradiograph showing IL-6 mRNA expression as determined by reverse transcription polymerase chain reaction in liver, spleen, and thymus at various time periods after in vivo stimulation of BALB/c mice (two mice/group) injected iv with 100 μl of PBS, 200 μl of CpG phosphorothioate ODN 5' TCCATGACGTTCCTGATGCT 3' (SEQ ID NO: 7) or non-CpG phosphorothioate ODN 5' TCCATGAGCTTCCTGAGTCT 3' (SEQ ID NO: 8).

RT-PCR A sense primer, an antisense primer, and an internal oligonucleotide probe for IL-6 were synthesized using published sequences (Montgomery, R. A. and M. S. Dallman (1991), Analysis for cytokine gene expression during fetal thymic ontogeny using the polymerase chain reaction (J. Immunol.) 147:554). cDNA synthesis and IL-6 PCR was done essentially as described by Montgomery and Dallman (Montgomery, R. A. And M. S. Dallman (1991), Analysis of cytokine gene expression during fetal thymic ontogeny using the polymerase chain reaction (J. Immunol.) 147:554) using RT-PCR reagents from Perkin-Elmer Corp. (Hayward, Calif.). Samples were analyzed after 30 cycles of amplification by gel electrophoresis followed by unblot analysis (stoye, J. P. et al., (1991) DNA hybridization in dried gels with fragmented probes: an improvement over blotting techniques, Techniques3: 123). Briefly, the gel was hybridized at room temperature for 30 min. in denaturation buffer (0.05 M NaOH, 1.5M NaCl) followed by incubation for 30 min. In renaturation buffer (1.5 M NaCl, 1 M Tris, pH 8) and a 30 min. Wash in double distilled water. The gel was dried and prehybridized at 47° C. for 2 hr. Hybridization buffer (5×SSPE, 0.1% SDS) containing 10 μg/ml denatured salmon sperm DNA. The gel was hybridized with 2×10$^6$ cpm/ml g-[$^{32}$ P] ATP end-labeled internal oligonucleotide probe for IL-6 (5'CATTTCCGATTTCCCA3') SEQ ID. NO: 118) overnight at 47° C., washed 4 times (2×SSC, 0.2% SDS) at room temperature and autoradiographed. The results are shown in FIG. 3.

Cell Proliferation assay. DBA/2 mice spleen B cells (5×10$^4$ cells/100 μl/well) were treated with media, CpG or non-CpG S—ODN (0.5 μM) or O—ODN (20 μM) for 24 hr at 37° C. Cells were pulsed for the last four hr. With either [$^3$H] Thymidine or [$^3$H] Uridine (1 μCi/well). Amounts of [$^3$H] incorporated were measured using Liquid Scintillation Analyzer (Packard Instrument Co., Downers Grove, Ill.).

Transfections and CAT assays. WEHI-231 cells (10$^7$ cells) were electroporated with 20 μg of control or human IL-6 promoter-CAT construct (kindly provided by S. Manolagas, Univ. of Arkansas) (Pottratz, S. T. Et. al., (1994) 17B-estradiol inhibits expression of human interleukin-6 promotor-reporter constructs by a receptor-dependent mechanism. J. Clin. Invest. 93:944) at 250 mV and 960 μF. Cells were stimulated with various concentrations of CpG or non-CpG ODN after electroporation. Chloramphenicol acetyltransferase (CAT) activity was measured by a solution assay (Seed, B. and J. Y. Sheen (1988) A single phase-extraction assay for chloramphenicol acetyl transferase activity. Gene 76:271) 16 hr. after transfection. The results are presented in FIG. 5.

Example 10

Oligodeoxynucleotide Modifications Determine the Magnitude of B Cell Stimulation by CpG Motifs ODN were synthesized on an Applied Biosystems Inc. (Foster City, Calif.) model 380A, 380B, or 394 DNA synthesizer using standard procedures (Beacage and Caruthers (1981) Deoxynucleoside phosphoramidites—A new class of key intermediates for deoxypolynucleotide synthesis. Tetrahedon Letters 22, 1859–1862.). Phosphodiester ODN were synthesized using standard beta-cyanoethyl phosphoramidite chemistry. Phosphorothioate linkages were introduced by oxidizing the phosphite linkage with elemental sulfur instead of the standard iodine oxidation. The four common nucleoside phosphoramidites were purchased from Applied Biosystems. All phosphodiester and thioate containing ODN were protected by treatment with concentrated ammonia at 55° C. for 12 hours. The ODN were purified by gel exclusion chromatography and lyophilized to dryness prior to use. Phosphorodithioate linkages were introduced by using deoxynucleoside S-(b-benzoylmercaptoethyl) pyrrolidino thiophosphoramidites (Wiesler, W. T. et al.,(1993) In Methods in Molecular Biology: Protocols for Oligonucleotides and Analogs—Synthesis and Properties, Agrawal, S. (Ed.), Humana Press, 191–206.). Dithioate containing ODN were deprotected by treatment with concentrated ammonia at 55° C. for 12 hours followed by reverse phase HPLC purification.

In order to synthesize oligomers containing methylphosphonothioates or methylphosphonates as well as phosphodiesters at any desired internucleotide linkage, two different synthetic cycles were used. The major synthetic differences in two cycles are the coupling reagent where dialkylaminomethylnucleoside phosphines are used and the oxidation reagents in the case of methylphosphonothioates. In order to synthesize either derivative, the condensation time has been increased for the dialkylaminomethylnucleoside phosphines due to the slower kinetics of coupling (Jager and Engels, (1984) Synthesis of deoxynucleoside methylphosphonates via a phosphonamidite approach. Tetrahedron Letters 24, 1437–1440). After the coupling step has been completed, the methylphosphnodiester is treated with the suflfurizing reagent (5% elemental sulfur, 100 millimolar N,N-diamethylaminopyridine in carbon disulfide/pyridine/triethylamine), four consecutive times for 450 seconds each to produce methylphosphonothioates. To produce methylphosphonate linkages, the methylphosphinodiester is treated with standard oxidizing reagent (0.1 M iodine in tetrahydrofuran/2,6-lutidine/water).

The silica gel bound oligomer was treated with distilled pyridine/concentrated ammonia, 1:1, (v/v) for four days at 4 degrees centigrade. The supernatant was dried in vacuo, dissolved in water and chromatographed on a G50/50 Sephadex column.

As used herein, O—ODN refers to ODN which are phosphodiester; S—ODN are completely phosphorothioate modified; S—O=ODN are chimeric ODN in which the central linkages are phosphodiester, but the two 5' and five 3' linkages are phosphorothioate modified; $2_s$—O—ODN are chimeric ODN in which the central linkages are phosphodiester, but the two 5' and five 3' linkages are phosphorodithioate modified; and MP—O—ODN are chimeric ODN in which the central linkages are phosphodiester, but the two 5' and five 3' linkages are methylphosphonate modified. The ODN sequences studied (with CpG dinucleotides indicated by underlining) include:

3D (5" GAGAACGCTGGACCTTCCAT), (SEQ. ID. NO. 20);

3M (5' TCCATGTCGGTCCTGATGCT), (SEQ. ID. NO. 28);

5 (5' GGCGTTATTCCTGACTCGCC), (SEQ. ID. NO. 99); and 6 (5' CCTACGTTGTATGCGCCCAGCT), (SEQ. ID NO. 100).

These sequences are representative of literally hundreds of CpG and non-CpG ODN that have been tested in the course of these studies.

Mice. DBA/2, or BXSB mice obtained from The Jackson Laboratory (Bar Harbor, Me.), and maintained under specific pathogen-free conditions were used as a source of lymphocytes at 5–10 wk of age with essentially identical results.

Cell proliferation assay. For cell proliferation assays, mouse spleen cells ($5 \times 10^4$ cells/100 μl/well) were cultured at 37° C. in a 5% $CO_2$ humidified incubator in RPMI-1640 supplemented with 10% (v/v) heat inactivated fetal calf serum (heated to 65° C. for experiments with O—ODN, or 56° C. for experiments using only modified ODN), 1.5 μM L-glutamine, 50 μM 2-mercaptoethanol, 100 U/ml penicillin and 100 μg/ml streptomycin for 24 hr or 48 hr as indicated. 1 μCi of $^3H$ uridine or thymidine (as indicated) was added to each well, and the cells harvested after an additional 4 hours of culture. Filters were counted by scintillation counting. Standard deviations of the triplicate wells were <5%. The results are presented in FIGS. 6–8.

Example 11

Induction of NK Activity

Phosphodiester ODN were purchased form Operon Technologies (Alameda, Calif.). Phosphorothioate ODN were purchased from the DNA core facility, University of Iowa, or from The Midland Certified Reagent Company (Midland Tex.). E. coli (strain B) DNA and calf thymus DNA were purchased from Sigma (St. Louis, Mo.). All DNA and ODN were purified by extraction with phenol:chloroform:isoamyl alcohol (25:24: 1) and/or ethanol precipitation. The LPS level in ODN was less than 12.5 ng/mg and E. coli and calf thymus DNA contained less than 2.5 ng of LPS/mg of DNA by Limulus assay.

Virus-free, 4–6 week old, DBA/2, C57BL/6 (B6) and congenitally thymic BALB/C mice were obtained on contract through the Veterans Affairs from the National Cancer Institute (Bethesda, Md.). C57BL/6 SCID mice were bred in the SPF barrier facility at the University of Iowa Animal Care Unit.

Human peripheral monucluclear blood leukocytes (PBMC) were obtained as previously described (Ballas, Z. K. et al., (1990) J. Allergy Clin. Immunol. 85:453; Ballas, Z. K. And W. Rasmussen (1990) J. Immunol. 145:1039; Ballas, Z. K. and W. Rasmussen (1993) J. Immunol. 150;17). Human or murine cells were cultured at $5 \times 10^6$/well, at 37° C. in a 5% $CO_2$ humidified atmosphere in 24-well plates (Ballas, Z. K. Et al., (1990) J. Allergy Clin. Immunol. 85:453; Ballas, Z. K. And W. Rasmussen (1990) J. Immunol 145:1039; and Ballas, Z. K. and W. Rasmussen (1193) J. Immunol, 150:17), with medium alone or with CpG or non-CpG ODN at the indicated concentrations, or with E. coli or calf thymus (50 μg/ml) at 37° C. for 24 hr. All cultures were harvested at 18 hr. and the cells were used as effectors in a standard 4 hr. $^{51}Cr$-release assay against K562 (human) or YAC-1 (mouse) target cells as previously described. For calculation of lytic units (LU), 1 LU was defined as the number of cells needed to effect 30% specific lysis. Where indicated, neutralizing antibodies against IFN-β (Lee Biomolecular, San Diego, Calif.) or IL-12 (C15.1, C15.6, C17.8, and C17.15; provided by Dr. Giorgio Trinchieri, The Winstar Institute, Philadelphia, Pa.) or their isotype controls were added at the initiation of cultures to a concentration of 10 μg/ml. For anti-IL-12 additional, 10 μg of each of the 4 MAB (or isotype controls) were added simultaneously. Recombinant human IL-2 was used at a concentration of 100 U/ml.

Example 12

Prevention of the Development of an Inflammatory Cellular

Infiltrate and Eosinophilia in a Murine Model of Asthma

6–8 week old C56BL/6 mice (from The Jackson Laboratory, Bar Harbor, Me.) were immunized with 5,000 Schistosoma mansoni eggs by intraperitoneal (i.p.) injection on days 0 and 7. Schistosoma mansoni eggs contain an antigen (Schistosoma mansoni egg antigen (SEA)) that induces a Th2 immune response (e.g. production of IgE antibody). IgE antibody production is known to be an important cause of asthma.

The immunized mice were then treated with oligonucleotides (30 μg in 200 μl saline by i.p. injection), which either contained an unmethylated CpG motif (i e., TCCATGA CGTTCCTGACGTT; SEQ ID NO.10) or did the (i.e., control, TCCATGAGCTTCCTGAGTCT; SEQ ID NO. 8). Soluble SeEA (10 μg in 25 μl of saline) was administered by intranasal instillation on days 14 and 21. Saline was used as a control.

Mice were sacrificed at various times after airway challenge. Whole lung lavage was performed to harvest airway and alveolar inflammatory cells. Cytokine levels were measured from lavage fluid by ELISA. RNA was isolated from whole lung for Northern analysis and RT-PCR studies using CsCl gradients. Lungs were inflated and perfused with 4% paraformaldehyde for histologic examination.

Figure 9:
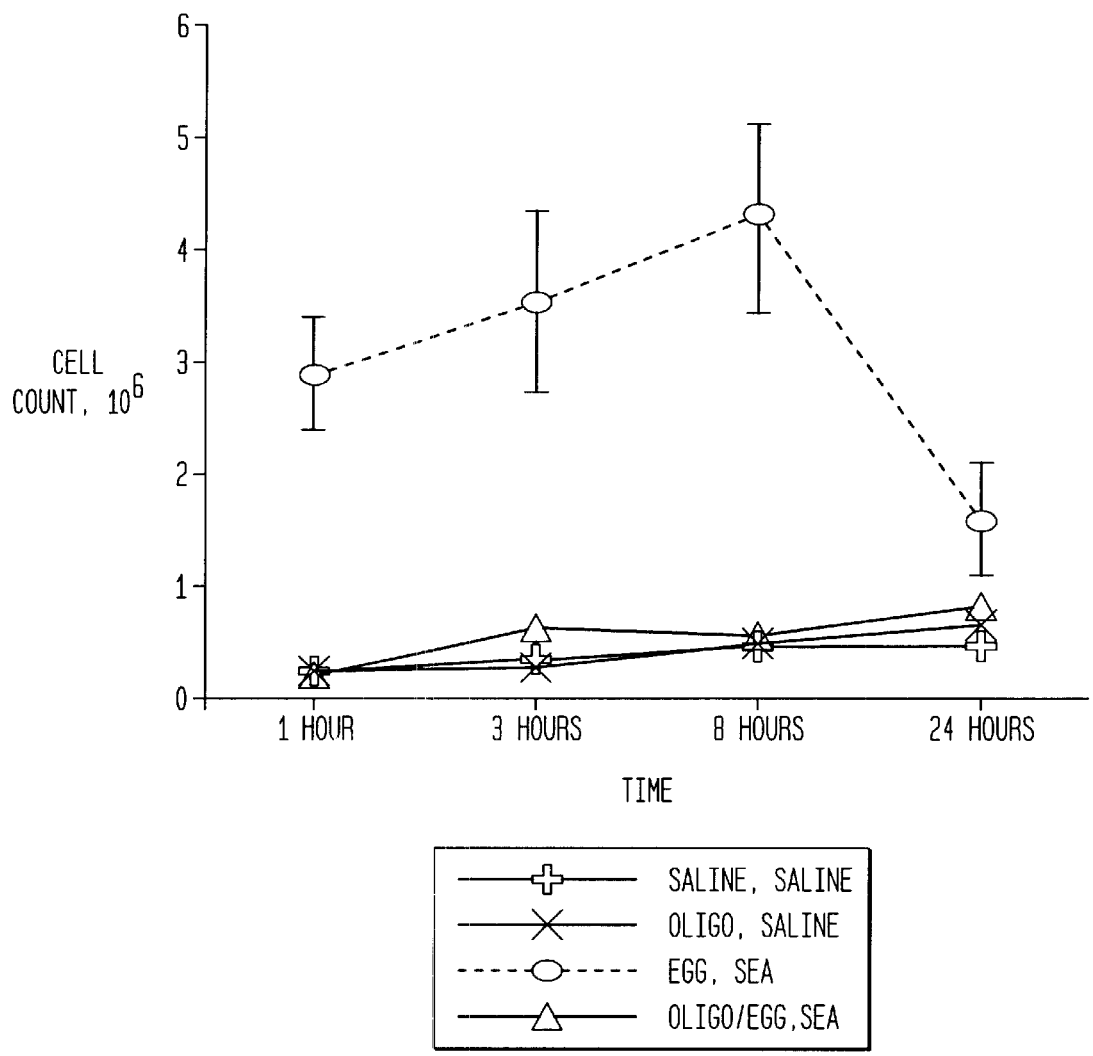
FIG. 9 is a graph plotting lung lavage cell count over time. The graph shows that when the mice are initially injected with *Schistosoma mansoni* eggs "egg", which induces a Th2 immune response, and subsequently inhale *Schistosoma*

FIG. 9 shows that when the mice are initially injected with the eggs i.p., and then inhale the egg antigen (open circle), many inflammatory cells are present in the lungs. However, when the mice are initially given a nucleic acid containing an unmethylated CpG motif along with the eggs, the inflammatory cells in the lung are not increased by subsequent inhalation of the egg antigen (open triangles).

FIG. 10 shows that the same results are obtained only when eosinophils present in the lung lavage are measured. Eosinophils are the type of inflammatory cell most closely associated with asthma.

FIG. 11 shows that when the mice are treated with a control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

FIG. 12 shows that very low doses of oligonucleotide (<10 μg) can give this protection.

FIG. 13 shows that the resultant inflammatory response correlates with the levels of the Th2 cytokine IL-4 in the lung.

FIG. 14 shows that administration of an oligonucleotide containing an unmethylated CpG motif can actually redirect the cytokine response of the lung to production of Il-12, indicating the Th1 type of immune response.

FIG. 15 shows that administration of an oligonucleotide containing an unmethylated CpG motif can also redirect the cytokine response of the lung to production of IFN-γ, indicating a Th1 type of immune response.

Example 13

CpG Oligonucleotides Induce Human PBMC to Secrete Cytokines

Human PBMC were prepared from whole blood by standard centrifugation over Ficoll hypaque. Cells ($5 \times 10^5$/ml) were cultured in 10% autologous serum in 95 well microtiter plates with CpG or control oligodeoxynucleotides (24 μg/ml for phosphodiester oligonucleotides; 6 g/ml for nuclease resistant phosphorothioate oligonucleotides) for 4 hr in the case of TNF-α or 24 hr. For the other cytokines before supernatant harvest and assay, measured by ELISA using Quantikine kits or reagents from R&D Systems (pg/ml) or cytokine ELISA kits from Biosource (for IL-12 assay). Assays were performed as per the manufacturer's instructions. Data are presented in Table 6 as the level of cytokine above that in wells with no added oligodeoxynucleotide.

Those skilled in the art will recognize, or be able to ascertain using no more than routine experimentation, many equivalents of the specific embodiments of the invention described herein. Such equivalents are intended to be encompassed by the following claims.

I claim:

1. A method for increasing the responsiveness of a cancer cell to a cancer therapy using an immunostimulatory nucleic acid as compared to the absence of the immunostimulatory nucleic acid, comprising:

administering to a subject having a cancer an effective amount for increasing the responsiveness of a cancer cell to a cancer therapy of an immunostimulatory nucleic acid, comprising:

$$5'X_1X_2CGX_3X_4 3'$$

wherein C is unmethylated, wherein $X_1X_2$ and $X_3X_4$ are nucleotides, and wherein the sequence is not palindromic.

2. The method of claim 1, further comprising administering a chemotherapeutic agent.

3. The method of claim 1, further comprising administering a cancer immunotherapeutic agent.

4. The method of claim 1, wherein the cancer is brain cancer.

5. The method of claim 1, wherein the cancer is lung cancer.

6. The method of claim 1, wherein the cancer is ovary cancer.

7. The method of claim 1, wherein the cancer is breast cancer.

8. The method of claim 1, wherein the cancer is prostate cancer.

9. The method of claim 1, wherein the cancer is colon cancer.

10. The method of claim 1, wherein the cancer is leukemia.

11. The method of claim 1, wherein the cancer is carcinoma.

12. The method of claim 1, wherein the cancer is sarcoma.

13. The method of claim 1, wherein at least one nucleotide has a phosphate backbone modification.

14. The method of claim 13, wherein the phosphate backbone modification is a phosphorothioate or phosphorodithioate modification.

15. The method of claim 14, wherein the nucleic acid backbone includes the phosphate backbone modification on the 5' inter-nucleotide linkages.

16. The method of claim 14, wherein the nucleic acid backbone includes the phosphate backbone modification on the 3' inter-nucleotide linkages.

17. The method of claim 1, wherein the oligonucleotide has 8 to 100 nucleotides.

18. The method of claim 1, wherein $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA.

19. The method of claim 1, wherein $X_1X_2$ are GpA and $X_3X_4$ are TpT.

20. The method of claim 1, wherein $X_1X_2$ are both purines and $X_3X_4$ are both pyrimidines.

21. The method of claim 1, wherein $X_1X_2$ are GpA and $X_3X_4$ are both pyrimidines.

22. The method of claim 1, wherein the oligonucleotide is 8 to 40 nucleotides in length.

23. The method of claim 1, wherein the oligonucleotide is isolated.

24. The method of claim 1, wherein the oligonucleotide is a synthetic oligonucleotide.

25. A method for enhancing recovery of bone marrow using an immunostimulatory nucleic acid as compared to the absence of the immunostimulatory nucleic acid in a subject undergoing or having undergone cancer therapy, comprising:

administering to a subject undergoing or having undergone cancer therapy which damages the bone marrow an effective amount for enhancing the recovery of bone marrow of an immunostimulatory nucleic acid, comprising:

$$5'X_1X_2CGX_3X_4 3'$$

wherein C is unmethylated, wherein $X_1X_2$ and $X_3X_4$ are nucleotides.

26. The method of claim 25, wherein at least one nucleotide has a phosphate backbone modification.

27. The method of claim 26, wherein the phosphate backbone modification is a phosphorothioate or phosphorodithioate modification.

28. The method of claim 25, wherein the oligonucleotide has 8 to 100 nucleotides.

29. The method of claim 25, wherein $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA.

30. In a method for stimulating an immune response in a subject having a cancer, the method of the type involving antigen dependent cellular cytotoxicity (ADCC), the improvement comprising:

administering to the subject an immunostimulatory nucleic acid, comprising:

$$5'X_1X_2CGX_3X_4 3'$$

wherein C is unmethylated, wherein $X_1X_2$ and $X_3X_4$ are nucleotides.

31. The method of claim 30, wherein at least one nucleotide has a phosphate backbone modification.

32. The method of claim 30, wherein the oligonucleotide has 8 to 100 nucleotides.

33. The method of claim 32, wherein the phosphate backbone modification is a phosphorothioate or phosphorodithioate modification.

34. The method of claim 32, wherein $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA.

35. The method of claim 30, wherein 5' $X_1X_2CGX_3X_4$ 3' is not palindromic.

36. A method for treating or preventing cancer, comprising:

administering to a subject having a cancer an effective amount for treating or preventing cancer of an immunostimulatory nucleic acid, comprising:

5'$X_1X_2CGX_3X_4$3' wherein C is unmethylated, wherein $X_1X_2$ and $X_3X_4$ are nucleotides, and wherein the sequence is not palindromic.

37. The method of claim 36, further comprising administering a chemotherapeutic agent.

38. The method of claim 36, further comprising administering a cancer immunotherapeutic agent.

39. The method of claim 36, wherein the cancer is brain cancer.

40. The method of claim 36, wherein the cancer is lung cancer.

41. The method of claim 36, wherein the cancer is ovarian cancer.

42. The method of claim 36, wherein the cancer is breast cancer.

43. The method of claim 36, wherein the cancer is prostate cancer.

44. The method of claim 36, wherein the cancer is colon cancer.

45. The method of claim 36, wherein the cancer is leukemia.

46. The method of claim 36, wherein the cancer is carcinoma.

47. The method of claim 36, wherein the cancer is sarcoma.

48. The method of claim 36, wherein at least one nucleotide has a phosphate backbone modification.

49. The method of claim 48, wherein the phosphate backbone modification is a phosphorothioate or phosphorodithioate modification.

50. The method of claim 49, wherein the nucleic acid backbone includes the phosphate backbone modification on the 5' inter-nucleotide linkages.

51. The method of claim 49, wherein the nucleic acid backbone includes the phosphate backbone modification on the 3' inter-nucleotide linkages.

52. The method of claim 36, wherein the oligonucleotide has 8 to 100 nucleotides.

53. The method of claim 36, wherein $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA.

54. The method of claim 36, wherein $X_1X_2$ are GpA and $X_3X_4$ are TpT.

55. The method of claim 36, wherein $X_1X_2$ are both purines and $X_3X_4$ are both pyrimidines.

56. The method of claim 36, wherein $X_1X_2$ are GpA and $X_3X_4$ are both pyrimidines.

57. The method of claim 36, wherein the oligonucleotide is 8 to 40 nucleotides in length.

* * * * *

UNITED STATES PATENT AND TRADEMARK OFFICE
CERTIFICATE OF CORRECTION

PATENT NO.      : 6,653,292 B1
APPLICATION NO. : 09/337619
DATED           : November 25, 2003
INVENTOR(S)     : Krieg et al.

It is certified that error appears in the above-identified patent and that said Letters Patent is hereby corrected as shown below:

On Title Page
[75]  Inventors: Arthur M. Krieg, Iowa City, IA (US); George
        Delete "Weiher" and insert "Weiner" Iowa City, IA (US)
        Add --Dennis Klinman, Potomac, MD(US); and Alfred D. Steinberg, Potomac, MD (US)--

Signed and Sealed this

Nineteenth Day of September, 2006

JON W. DUDAS
*Director of the United States Patent and Trademark Office*